US010221242B2

(12) United States Patent
Wong et al.

(10) Patent No.: US 10,221,242 B2
(45) Date of Patent: Mar. 5, 2019

(54) ANTIBODIES SPECIFIC FOR EPIDERMAL GROWTH FACTOR RECEPTOR VARIANT III AND THEIR USES

(71) Applicant: PFIZER INC., New York, NY (US)

(72) Inventors: Oi Kwan Wong, Belmont, CA (US); Joyce Ching Chou, Sunnyvale, CA (US); Barbra Johnson Sasu, San Francisco, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/402,807

(22) Filed: Jan. 10, 2017

(65) Prior Publication Data

US 2017/0210812 A1   Jul. 27, 2017

Related U.S. Application Data

(60) Provisional application No. 62/431,766, filed on Dec. 8, 2016, provisional application No. 62/281,543, filed on Jan. 21, 2016.

(51) Int. Cl.
| | |
|---|---|
| *A61K 39/395* | (2006.01) |
| *C07K 16/28* | (2006.01) |
| *C07K 16/30* | (2006.01) |
| *A61K 39/00* | (2006.01) |

(52) U.S. Cl.
CPC ...... *C07K 16/2863* (2013.01); *C07K 16/2803* (2013.01); *C07K 16/2809* (2013.01); *C07K 16/30* (2013.01); *C07K 16/3053* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/52* (2013.01); *C07K 2317/55* (2013.01); *C07K 2317/73* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 2012/0189630 A1 | 7/2012 | Bigner et al. | |
| 2014/0037628 A1 | 2/2014 | Morgan et al. | |
| 2017/0210811 A1 | 7/2017 | Wong et al. | |
| 2017/0275366 A1 | 9/2017 | Schiffer-Mannioui | |

FOREIGN PATENT DOCUMENTS

| | | |
|---|---|---|
| KR | 10-2013-0124521 A | 11/2013 |
| WO | 2008/045437 | 4/2008 |
| WO | 2012/079000 | 6/2012 |
| WO | 2012/138475 | 10/2012 |
| WO | 2013/185010 | 12/2013 |
| WO | 2014/011988 | 1/2014 |
| WO | WO2014/039523 | 3/2014 |
| WO | 2014/130657 | 8/2014 |
| WO | 2014/153002 | 9/2014 |
| WO | 2015/006482 | 1/2015 |
| WO | WO-2015/018527 A1 | 2/2015 |
| WO | 2015/092024 | 6/2015 |
| WO | 2016/016341 | 2/2016 |
| WO | 2017/021370 | 2/2017 |

OTHER PUBLICATIONS

B. Philip et al: "A highly compact epitope-based marker/suicide gene for easier and safer T-cell therapy", Blood, vol. 124, No. 8, Aug. 21, 2014.

Jianfeng Han et al: "CAR-Engineered NK Cells Targeting Wild-Type EGFR and EGFRvIII Enhance Killing of Glioblastoma and Patient-Derived Glioblastoma Stem Cells", Scientific Reports, vol. 5, Jul. 9, 2015.

Bryan D. Choi et al: "A novel bispecific antibody recruits T cells to eradicate tumors in the "immunologically privileged" central nervous system", Oncoimmunology, vol. 2, No. 4, Apr. 27, 2013 (Apr. 27, 2013), p. e23639.

B. D. Choi et al: "Systemic administration of a bispecific antibody targeting EGFRvIII successfully treats intracerebral glioma", Proceedings of the National Academy of Sciences, vol. 110, No. 1, Dec. 17, 2012 (Dec. 17, 2012), pp. 270-275.

Chan-Juan Shen et al: "Chimeric antigen receptor containing ICOS signaling domain mediates specific and efficient antitumor effect of T cells against EGFRvIII expressing glioma", Journal of Hematology & Oncology, Biomed Central LTD, London UK, vol. 6, No. 1, May 9, 2013 (May 9, 2013), p. 33.

Ian M Zitron et al: "Targeting and killing of glioblastoma with activated T cells armed with bispecific antibodies", BMC Cancer, Biomed Central, London, GB, vol. 13, No. 1, Feb. 22, 2013 (Feb. 22, 2013), p. 83.

Laurent Poirot, et al., 521. Multiplex Genome Editing of TCR alpha/CD52 Genes as a Platform for "Off the Shelf" Adoptive T-Cell Immunotherapies; 17th Annual Meeting of the American Society of the Gene and Cell Therapy (ASGCT), vol. 22, Suppl. 1, May 1, 2014; pp. S201-S202.

(Continued)

*Primary Examiner* — Laura B Goddard
*Assistant Examiner* — Meera Natarajan
(74) *Attorney, Agent, or Firm* — Cooley LLP

(57) ABSTRACT

The present invention provides antibodies that specifically bind to EGFRvIII (Epidermal Growth Factor Receptor Variant III). The invention further provides bispecific antibodies that bind to EGFRvIII and another antigen (e.g., CD3) as well as antibody conjugates (e.g., antibody-drug-conjugates). The invention further relates to antibody encoding nucleic acids, and methods of obtaining such antibodies (monospecific and bispecific) and antibody conjugates. The invention further relates to therapeutic methods for use of these antibodies and antibody conjugates for the treatment of EGFRvIII-mediated pathologies, including cancer such as glioblastoma.

25 Claims, 6 Drawing Sheets

Specification includes a Sequence Listing.

(56) References Cited

OTHER PUBLICATIONS

Laurent Poirot, et al., T-Cell Engineering for "off the Shelf" Adoptive Immunotherapy, Blood Journal, 122, Nov. 2013.

Cecile Schiffer Mannioui, et al. Treatment of B cells maligancies with anit-CD19 CAR+, TCR-, CD52- allogenic T cells, Journal for Immunotherapy of Cancer, Biomed Central LTD, vol. 1, No. Suppl 1, Nov. 7, 2013, p. P34.

Edwards, B.M. et al (2003). "The Remarkable Flexibility of the Human Antibody Repertoire; Isolation of Over One Thousand Different Antibodies to a Single Protein," BLyS J. Mol. Biol, 334:103-118.

Final Office Action dated Sep. 14, 2018, for U.S. Appl. No. 15/402,760, filed Jan. 10, 2017, 18 pages.

Lloyd et al., Modelling the human immune response: performance of a 1011 human antibody repertoire against a broad panel of therapeutically relevant antigens Protein Engineering, Design & Selection vol. 22 No. 3 pp. 159-168, 2009.

Bendig, M.M. et al. (1995). "Humanization of rodent monoclonal antibodies by CDR grafting a companion to methods," Methods: A companion to methods in enzymology, pp. 83-93.

Colman, P.M. (1994). "Effects of amino acid sequence changes on antibody-antigen interactions," Res. Immunol. 145:33-36.

International Search Report dated Sep. 16, 2015, for PCT Application No. PCT/EP2015/067439, filed on Jul. 29, 2015, 6 pages.

International Search Report dated Apr. 5, 2017, for PCT Application No. PCT/IB2017/050108, filed on Jan. 10, 2017, 5 pages.

International Search Report dated May 2, 2017, for PCT Application No. PCT/IB2017/050109, filed on Jan. 10, 2017, 5 pages.

Johnson, L.A. et al. (2015). "Rational development and characterization of humanized anti-EGFR variant III chimeric antigen receptor T cells for glioblastoma," Sci. Transl. Med. 7:275(ra22), 16 total pages.

Kimchi-Sarfaty, C. et al. (2007). "A "silent" polymorphism in the MDR1 gene changes substrate specificity," Science 315:525-528.

Morgan, R.A. et al. (2012). "Recognition of glioma stem cells by genetically modified T cells targeting EGFRvIII and development of adoptive cell therapy for glioma," Human Gene Ther. 23:1043-1053.

Non-Final Office Action dated Mar. 1, 2018, for U.S. Appl. No. 15/402,760, filed Jan. 10, 2017, 28 pages.

Rudikoff, S. et al. (1982). "Single amino acid substitution altering antigen-binding specificity," PNAS 79:1979-1983.

Written Opinion of the International Searching Authority dated Sep. 16, 2015, for PCT Application No. PCT/EP2015/067439, filed on Jul. 29, 2015, 7 pages.

Written Opinion of the International Searching Authority dated Apr. 5, 2017, for PCT Application No. PCT/IB2017/050108, filed on Jan. 10, 2017, 7 pages.

Written Opinion of the International Searching Authority dated May 2, 2017, for PCT Application No. PCT/IB2017/050109, filed on Jan. 10, 2017, 7 pages.

Notice of Allowance dated Nov. 29, 2018, for U.S. Appl. No. 15/402,760, filed Jan. 10, 2017, 15 pages.

LN229-EGFRvIII

LN229

SEQUENCE LISTING

```
<160> NUMBER OF SEQ ID NOS: 292

<210> SEQ ID NO 1
<211> LENGTH: 115
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Asp Tyr
            20                  25                  30

Thr Leu His Trp Val Lys Gln Ser His Val Lys Ser Leu Glu Trp Ile
        35                  40                  45

Gly Gly Ile Asp Pro Ile Asn Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Glu Ala Met Asp Ser Trp Gly Gln Gly Thr Ser Val Thr
            100                 105                 110

Val Ser Ser
        115

<210> SEQ ID NO 2
<211> LENGTH: 112
<212> TYPE: PRT
<213> ORGANISM: Artificial Sequence
<220> FEATURE:
<223> OTHER INFORMATION: Synthetic Construct

<400> SEQUENCE: 2

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Phe Tyr Tyr Cys Val Gln Asp
                85                  90                  95

Thr His Phe Pro Leu Thr Phe Gly Ala Gly Thr Lys Leu Glu Leu Lys
            100                 105                 110

<210> SEQ ID NO 3
<211> LENGTH: 115
<212> TYPE: PRT
<213> ORGANISM: Artificial Sequence
```

<220> FEATURE:
<223> OTHER INFORMATION: Synthetic Construct

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Leu His Trp Val Arg Gln Ala Pro Gly Gln Gly Leu Glu Trp Met
        35                  40                  45

Gly Gly Ile Asn Pro Ile Asn Gly Gly Thr Thr Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Ala Met Asp Ser Trp Gly Gln Gly Thr Leu Val Thr
            100                 105                 110

Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: Synthetic Construct

<400> SEQUENCE: 4

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Asp
                85                  90                  95

Thr His Phe Pro Leu Thr Phe Gly Gly Gly Thr Lys Val Glu Ile Lys
            100                 105                 110

<210> SEQ ID NO 5
<211> LENGTH: 115
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Leu His Trp Val Arg Gln Ala Pro Gly Gln Gly Leu Glu Trp Met
        35                  40                  45

```
Gly Gly Ile Trp Pro Ile Thr Gly Gly Thr Thr Tyr Asn Gln Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Glu Ala Gln Gly Ser Trp Gly Gln Gly Thr Leu Val Thr
                100                 105                 110

Val Ser Ser
        115
```

<210> SEQ ID NO 6
<211> LENGTH: 112
<212> TYPE: PRT
<213> ORGANISM: Artificial Sequence
<220> FEATURE:
<223> OTHER INFORMATION: Synthetic Construct

<400> SEQUENCE: 6

```
Asp Val Val Met Thr Gln Ser Pro Leu Ser Leu Pro Val Thr Leu Gly
  1               5                  10                  15

Gln Pro Ala Ser Ile Ser Cys Lys Ser Ser Gln Ser Leu Leu Tyr Ser
                 20                  25                  30

Asn Gly Lys Thr Tyr Leu Asn Trp Phe Gln Gln Arg Pro Gly Gln Ser
             35                  40                  45

Pro Arg Arg Leu Ile Tyr Gln Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Asp
                 85                  90                  95

Thr His Phe Pro Leu Thr Phe Gly Gly Gly Thr Lys Val Glu Ile Lys
                100                 105                 110
```

<210> SEQ ID NO 7
<211> LENGTH: 115
<212> TYPE: PRT
<213> ORGANISM: Artificial Sequence
<220> FEATURE:
<223> OTHER INFORMATION: Synthetic Construct

<400> SEQUENCE: 7

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                 20                  25                  30

Thr Leu His Trp Val Arg Gln Ala Pro Gly Gln Gly Leu Glu Trp Met
             35                  40                  45

Gly Gly Ile Trp Pro Ile Thr Gly Gly Thr Thr Tyr Asn Gln Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Glu Ala Glu Gly Ser Trp Gly Gln Gly Thr Leu Val Thr
                100                 105                 110

Val Ser Ser
        115
```

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

```
Asp Val Val Met Thr Gln Ser Pro Leu Ser Leu Pro Val Thr Leu Gly
1               5                   10                  15

Gln Pro Ala Ser Ile Ser Cys Lys Ser Gln Ser Leu Leu Tyr Ser
            20                  25                  30

Asn Asp Lys Thr Tyr Thr Asn Trp Phe Gln Gln Arg Pro Gly Gln Ser
        35                  40                  45

Pro Arg Arg Leu Ile Tyr Glu Val Ser Lys Leu Asp Val Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Asp
                85                  90                  95

Thr His Phe Pro Leu Thr Phe Gly Gly Gly Thr Lys Val Glu Ile Lys
            100                 105                 110
```

<210> SEQ ID NO 9
<211> LENGTH: 121
<212> TYPE: PRT
<213> ORGANISM: Artificial Sequence
<220> FEATURE:
<223> OTHER INFORMATION: Synthetic Construct

<400> SEQUENCE: 9

```
Gln Val Thr Leu Lys Glu Ser Gly Pro Val Leu Leu Lys Pro Thr Glu
1               5                   10                  15

Thr Leu Thr Leu Thr Cys Thr Val Ser Gly Phe Ser Leu Ser Asn Pro
            20                  25                  30

Arg Met Gly Val Ser Trp Ile Arg Gln Pro Pro Gly Lys Ala Leu Glu
        35                  40                  45

Trp Phe Ala His Ile Phe Ser Thr Asp Glu Lys Ser Leu Lys Leu Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Ala Pro Val Asp Ser Ala Thr Tyr Tyr
                85                  90                  95

Cys Ala Arg Asp Ser Ser Asn Tyr Glu Gly Tyr Phe Asp Phe Trp Gly
            100                 105                 110

Gln Gly Thr Leu Val Thr Val Ser Ser
        115                 120
```

<210> SEQ ID NO 10
<211> LENGTH: 107
<212> TYPE: PRT
<213> ORGANISM: Artificial Sequence
<220> FEATURE:
<223> OTHER INFORMATION: Synthetic Construct

<400> SEQUENCE: 10

```
Glu Val Val Leu Thr Gln Ser Pro Ala Thr Leu Ser Val Ser Pro Gly
1               5                   10                  15
```

Glu Arg Ala Thr Leu Ser Cys Arg Ala Ser Gln Ser Val Arg Ser Asn
            20                  25                  30

Leu Ala Trp Tyr Gln Gln Lys Ser Gly Gln Ala Pro Arg Leu Leu Ile
        35                  40                  45

Tyr Gly Ser Thr Ile Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asp Trp Pro Phe
                85                  90                  95

Thr Phe Gly Pro Gly Thr Lys Val Asp Ile Lys
            100                 105

<210> SEQ ID NO 11
<211> LENGTH: 121
<212> TYPE: PRT
<213> ORGANISM: Artificial Sequence
<220> FEATURE:
<223> OTHER INFORMATION: Synthetic Construct

<400> SEQUENCE: 11

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Thr Asp Glu Lys Ser Ile Arg Arg Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Phe
                85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: Synthetic Construct

<400> SEQUENCE: 12

Glu Val Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Asn
            20                  25                  30

Phe Ala Trp Tyr Gln Gln Arg Pro Gly Gln Ala Pro Arg Leu Leu Leu
        35                  40                  45

Tyr Gly Ala Thr Thr Arg Ala Thr Gly Leu Pro Gly Arg Phe Ser Gly
    50                  55                  60

Ser Gly Ser Gly Thr Glu Asn Ile Leu Thr Ile Ser Ser Leu Gln Ser
65                  70                  75                  80

Glu Asp Phe Ala Ile Tyr Phe Cys Gln Gln Tyr Lys Asp Trp Pro Phe
                85                  90                  95

```
Thr Phe Gly Pro Gly Ser Lys Val Asp Ile Lys
            100                 105
```

<210> SEQ ID NO 13
<211> LENGTH: 121
<212> TYPE: PRT
<213> ORGANISM: Artificial Sequence
<220> FEATURE:
<223> OTHER INFORMATION: Synthetic Construct
<400> SEQUENCE: 13

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Gly His Ile Phe Ser Thr Asp Glu Lys Ser Tyr Ser Thr Ser
    50                  55                  60

Leu Arg Gly Arg Ile Thr Ile Ser Lys Asp Thr Ser Arg Gly Leu Val
65                  70                  75                  80

Val Leu Thr Leu Thr Asn Met Asp Pro Val Asp Thr Ala Thr Tyr Tyr
                85                  90                  95

Cys Ala Arg Asp Ser Ser Asn Tyr Glu Gly Tyr Phe Asp Phe Trp Gly
            100                 105                 110

Pro Gly Phe Leu Val Thr Val Ser Ser
        115                 120
```

<210> SEQ ID NO 14
<211> LENGTH: 107
<212> TYPE: PRT
<213> ORGANISM: Artificial Sequence
<220> FEATURE:
<223> OTHER INFORMATION: Synthetic Construct
<400> SEQUENCE: 14

```
Glu Ile Val Met Thr Gln Ser Pro Ala Thr Leu Ser Val Ser Pro Gly
1               5                   10                  15

Glu Arg Ala Thr Leu Ser Cys Arg Val Ser Gln Ser Ile Gly Ala Asn
            20                  25                  30

Leu Ala Trp Tyr Gln Gln Lys Phe Gly Gln Ala Pro Arg Leu Leu Ile
        35                  40                  45

Tyr Gly Ala Ser Thr Arg Ala Thr Gly Ile Pro Val Arg Phe Ser Gly
    50                  55                  60

Gly Gly Ser Gly Thr Glu Phe Thr Leu Thr Ile Ser Ser Leu Gln Ser
65                  70                  75                  80

Glu Asp Phe Ala Ile Tyr Ser Cys Gln Gln Tyr Ile Tyr Trp Pro Phe
                85                  90                  95

Thr Phe Gly Pro Gly Thr Thr Val Asp Ile Lys
            100                 105
```

<210> SEQ ID NO 15
<211> LENGTH: 121
<212> TYPE: PRT
<213> ORGANISM: Artificial Sequence
<220> FEATURE:
<223> OTHER INFORMATION: Synthetic Construct
<400> SEQUENCE: 15

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
                20                  25                  30

Arg Met Gly Val Ser Trp Ile Arg Gln Pro Pro Gly Lys Ala Leu Glu
            35                  40                  45

Trp Phe Ala His Ile Phe Ser Thr Asp Glu Lys Ser Phe Arg Thr Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Tyr Trp Gly
            100                 105                 110

Gln Gly Ile Leu Val Thr Val Ser Ser
            115                 120
```

<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Asn Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Val Pro Ala Arg Phe Ser Gly
    50                  55                  60

Ser Asp Ser Gly Thr Glu Phe Ser Leu Thr Ile Ser Ser Leu Gln Ser
65                  70                  75                  80

Glu Asp Phe Ala Val Tyr Phe Cys Gln Gln Tyr Lys Asp Trp Pro Phe
                85                  90                  95

Thr Phe Gly Pro Gly Thr Lys Val Glu Ile Lys
            100                 105
```

<210> SEQ ID NO 17
<211> LENGTH: 122
<212> TYPE: PRT
<213> ORGANISM: Artificial Sequence
<220> FEATURE:
<223> OTHER INFORMATION: Synthetic Construct

<400> SEQUENCE: 17

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Val
                20                  25                  30

Arg Met Gly Val Ser Trp Ile Arg Gln Pro Pro Gly Lys Ala Leu Glu
            35                  40                  45

Trp Phe Ala His Ile Phe Ser Ser Asp Glu Lys Ser Ile Arg Arg Ser
    50                  55                  60

Leu Arg Ser Arg Leu Thr Leu Ser Lys Asp Thr Ser Lys Ser Gln Val
65                  70                  75                  80
```

```
Val Leu Thr Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Phe Trp Gly
            100                 105                 110

Gln Gly Thr Leu Val Thr Val Ser Ser Asn
        115                 120

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

Asp Met Val Val Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asp
            20                  25                  30

Leu Ala Trp Tyr Gln Gln Pro Pro Gly Gln Ser Pro Arg Leu Leu Ile
        35                  40                  45

Tyr Gly Ala Ser Thr Arg Ala Thr Gly Val Pro Ala Arg Phe Ser Gly
50                  55                  60

Ser Gly Ser Gly Thr Asp Phe Thr Leu Thr Ile Thr Ser Leu Glu Ser
65                  70                  75                  80

Glu Asp Phe Ala Val Tyr Tyr Cys Gln Gln Tyr Asn Asp Trp Pro Phe
                85                  90                  95

Thr Phe Gly Pro Gly Thr Lys Val Asp Ile Lys
            100                 105

<210> SEQ ID NO 19
<211> LENGTH: 121
<212> TYPE: PRT
<213> ORGANISM: Artificial Sequence
<220> FEATURE:
<223> OTHER INFORMATION: Synthetic Construct

<400> SEQUENCE: 19

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Val
            20                  25                  30

Arg Met Gly Val Ser Trp Ile Arg Gln Pro Pro Gly Lys Ala Leu Glu
        35                  40                  45

Trp Phe Ala His Ile Phe Ser Ser Asp Glu Lys Ser Ile Arg Arg Ser
50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 20
<211> LENGTH: 107
<212> TYPE: PRT
```

```
<213> ORGANISM: Artificial Sequence
<220> FEATURE:
<223> OTHER INFORMATION: Synthetic Construct

<400> SEQUENCE: 20

Glu Met Glu Val Thr Gln Ser Pro Ala Thr Leu Ser Val Ser Pro Gly
1               5                   10                  15

Glu Arg Ala Thr Leu Ser Cys Arg Ala Ser Gln Asn Ile Gly Ser Asp
            20                  25                  30

Leu Ala Trp Tyr Gln Gln Ser Gly Gln Ala Pro Arg Leu Leu Ile
        35                  40                  45

Ser Gly Ala Ser Thr Arg Ala Thr Gly Val Pro Thr Arg Phe Ser Gly
65              70                  75                  80

Ser Gly Ser Gly Thr Asp Phe Thr Leu Thr Ile Thr Ser Leu Gln Ser
65              70                  75                  80

Glu Asp Phe Ala Val Tyr Tyr Cys Gln Gln Tyr Asn Asp Trp Pro Phe
                85                  90                  95

Thr Phe Gly Pro Gly Thr Lys Val Asp Ile Lys
            100                 105

<210> SEQ ID NO 21
<211> LENGTH: 121
<212> TYPE: PRT
<213> ORGANISM: Artificial Sequence
<220> FEATURE:
<223> OTHER INFORMATION: Synthetic Construct

<400> SEQUENCE: 21

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Thr Asp Glu Lys Ser Ile Arg Arg Ser
    50                  55                  60

Leu Arg Ser Arg Leu Thr Leu Ser Lys Asp Thr Ser Lys Ser Gln Val
65              70                  75                  80

Val Leu Ile Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 22
<211> LENGTH: 107
<212> TYPE: PRT
<213> ORGANISM: Artificial Sequence
<220> FEATURE:
<223> OTHER INFORMATION: Synthetic Construct

<400> SEQUENCE: 22

Glu Val Val Met Thr Gln Ser Pro Pro Asn Leu Ser Val Ser Pro Gly
1               5                   10                  15

Glu Arg Ala Thr Leu Ser Cys Arg Ala Ser Gln Ser Val Thr Ser Asn
            20                  25                  30

Phe Ala Trp Tyr Gln Gln Arg Pro Gly Gln Ser Pro Arg Leu Leu Leu
        35                  40                  45
```

```
Tyr Gly Ala Ser Thr Arg Ala Thr Gly Val Pro Gly Arg Phe Ser Gly
         50                  55                  60

Ser Gly Ser Gly Thr Glu Asn Ile Leu Thr Ile Ser Ser Leu Gln Ser
 65                  70                  75                  80

Glu Asp Phe Ala Val Tyr Phe Cys Gln Gln Tyr Lys Asp Trp Pro Phe
                 85                  90                  95

Thr Phe Gly Pro Gly Ser Lys Val Asp Ile Lys
            100                 105
```

<210> SEQ ID NO 23
<211> LENGTH: 121
<212> TYPE: PRT
<213> ORGANISM: Artificial Sequence
<220> FEATURE:
<223> OTHER INFORMATION: Synthetic Construct

<400> SEQUENCE: 23

```
Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Asn Ala
                 20                  25                  30

Arg Met Gly Val Ser Trp Ile Arg Gln Pro Pro Gly Lys Ala Leu Glu
             35                  40                  45

Trp Leu Ala His Ile Phe Ser Thr Asp Glu Lys Ser Ile Arg Arg Ser
 50                  55                  60

Leu Arg Ser Arg Leu Thr Leu Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
            115                 120
```

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

```
Glu Val Val Met Thr Gln Ser Pro Ala Thr Leu Ser Val Ser Pro Gly
 1               5                  10                  15

Glu Arg Ala Thr Leu Ser Cys Arg Ala Ser Gln Gly Val Ser Ser Asn
                 20                  25                  30

Phe Ala Trp Tyr Gln Gln Arg Pro Gly Gln Ser Pro Arg Leu Leu Leu
             35                  40                  45

Tyr Gly Ala Ser Thr Arg Ala Thr Gly Val Pro Gly Arg Phe Ser Gly
 50                  55                  60

Ser Gly Ser Gly Thr Glu Asn Ile Leu Thr Ile Ser Ser Leu Gln Ser
 65                  70                  75                  80

Glu Asp Phe Ala Ile Tyr Phe Cys Gln Gln Tyr Lys Asp Trp Pro Phe
                 85                  90                  95

Thr Phe Gly Pro Gly Ser Lys Val Asp Ile Lys
            100                 105
```

<210> SEQ ID NO 25
<211> LENGTH: 121
<212> TYPE: PRT
<213> ORGANISM: Artificial Sequence
<220> FEATURE:
<223> OTHER INFORMATION: Synthetic Construct

<400> SEQUENCE: 25

```
Gln Val Thr Leu Glu Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Pro Glu
        35                  40                  45

Trp Phe Ala His Ile Phe Ser Thr Asp Glu Lys Ser Leu Arg Leu Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Asp Ser Ser Asn Tyr Glu Gly Tyr Phe Asp Tyr Trp Gly
            100                 105                 110

Gln Gly Thr Leu Val Thr Val Ser Ser
        115                 120
```

<210> SEQ ID NO 26
<211> LENGTH: 107
<212> TYPE: PRT
<213> ORGANISM: Artificial Sequence
<220> FEATURE:
<223> OTHER INFORMATION: Synthetic Construct

<400> SEQUENCE: 26

```
Glu Val Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Arg Asn
            20                  25                  30

Leu Ala Trp Tyr Gln Gln Lys Pro Gly Gln Ala Pro Arg Leu Leu Ile
        35                  40                  45

Phe Gly Thr Ser Thr Arg Ala Thr Gly Ile Pro Ala Arg Phe Ser Gly
    50                  55                  60

Ser Gly Ser Gly Thr Glu Phe Thr Leu Thr Ile Asp Ser Leu Gln Ser
65                  70                  75                  80

Glu His Ser Gly Leu Tyr Tyr Cys Gln Gln Tyr Asn Asp Trp Pro Phe
                85                  90                  95

Thr Phe Gly Pro Gly Thr Lys Val Asp Ile Lys
            100                 105
```

<210> SEQ ID NO 27
<211> LENGTH: 121
<212> TYPE: PRT
<213> ORGANISM: Artificial Sequence
<220> FEATURE:
<223> OTHER INFORMATION: Synthetic Construct

<400> SEQUENCE: 27

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30
```

```
Lys Met Gly Val Ser Trp Ile Arg Gln Pro Pro Gly Lys Ala Leu Glu
            35                  40                  45

Trp Leu Ala His Ile Phe Ser Thr Asp Glu Lys Ser Ile Arg Arg Ser
 50                  55                  60

Leu Arg Ser Arg Leu Thr Met Ser Lys Asp Thr Ser Lys Ser Gln Val
 65                  70                  75                  80

Val Leu Thr Met Thr Asn Met Asp Pro Val Asp Thr Ala Thr Tyr Tyr
                    85                  90                  95

Cys Val Arg Asp Ser Ser Asn Tyr Glu Gly Tyr Phe Asp Tyr Trp Gly
                100                 105                 110

Gln Gly Thr Leu Val Thr Val Ser Ser
            115                 120

<210> SEQ ID NO 28
<211> LENGTH: 107
<212> TYPE: PRT
<213> ORGANISM: Artificial Sequence
<220> FEATURE:
<223> OTHER INFORMATION: Synthetic Construct

<400> SEQUENCE: 28

Glu Val Leu Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Thr Asn
                20                  25                  30

Phe Ala Trp Tyr Gln Gln Arg Pro Gly Gln Ala Pro Arg Leu Leu Leu
            35                  40                  45

Phe Gly Ala Ser Thr Arg Ala Thr Gly Ile Pro Gly Arg Phe Ser Gly
 50                  55                  60

Ser Gly Ser Gly Thr Glu Asn Ile Leu Thr Ile Ser Ser Leu Gln Ser
 65                  70                  75                  80

Glu Asp Phe Ala Ile Tyr Phe Cys Gln Gln Tyr Lys Asp Trp Pro Phe
                 85                  90                  95

Thr Phe Gly Pro Gly Ser Lys Val Glu Ile Lys
                100                 105

<210> SEQ ID NO 29
<211> LENGTH: 107
<212> TYPE: PRT
<213> ORGANISM: Artificial Sequence
<220> FEATURE:
<223> OTHER INFORMATION: Synthetic Construct

<400> SEQUENCE: 29

Asp Val Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Asn Ser Asn
                20                  25                  30

Leu Ala Trp Tyr Gln Gln Asn Pro Gly Gln Ala Pro Arg Leu Leu Ile
            35                  40                  45

Phe Gly Ser Ser Thr Arg Ala Thr Gly Ile Pro Ala Ser Phe Ser Gly
 50                  55                  60

Ser Gly Ser Gly Thr Glu Phe Thr Leu Thr Ile Asn Ser Leu Gln Ser
 65                  70                  75                  80

Glu His Ser Ala Val Tyr Tyr Cys Gln Gln Tyr Asn Asp Trp Pro Phe
                 85                  90                  95

Thr Phe Gly Pro Gly Thr Lys Val Asp Ile Lys
```

<210> SEQ ID NO 30
<211> LENGTH: 121
<212> TYPE: PRT
<213> ORGANISM: Artificial Sequence
<220> FEATURE:
<223> OTHER INFORMATION: Synthetic Construct

<400> SEQUENCE: 30

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Pro
            20                  25                  30

Arg Met Gly Val Ser Trp Ile Arg Gln Pro Pro Gly Lys Ala Leu Glu
        35                  40                  45

Trp Leu Gly His Ile Phe Ser Ser Asp Glu Lys Ser Tyr Arg Leu Ser
    50                  55                  60

Leu Arg Ser Arg Leu Ser Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Asp Ser Ser Asn Tyr Gly Tyr Phe Asp Tyr Trp Gly
            100                 105                 110

Gln Gly Thr Leu Val Thr Val Ser Ser
        115                 120
```

<210> SEQ ID NO 31
<211> LENGTH: 107
<212> TYPE: PRT
<213> ORGANISM: Artificial Sequence
<220> FEATURE:
<223> OTHER INFORMATION: Synthetic Construct

<400> SEQUENCE: 31

```
Glu Val Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ile Asn Asn
            20                  25                  30

Leu Ala Trp Tyr Gln Gln Lys Pro Gly Gln Ala Pro Arg Leu Leu Ile
        35                  40                  45

Tyr Gly Thr Ser Thr Arg Ala Thr Asp Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Asp Tyr Asn Asn Trp Pro Phe
                85                  90                  95

Thr Phe Gly Pro Gly Thr Lys Val Asp Ile Lys
            100                 105
```

<210> SEQ ID NO 32
<211> LENGTH: 121
<212> TYPE: PRT
<213> ORGANISM: Artificial Sequence
<220> FEATURE:
<223> OTHER INFORMATION: Synthetic Construct

<400> SEQUENCE: 32

```
Gln Val Thr Leu Lys Glu Ser Gly Pro Val Leu Val Lys Pro Ile Glu
1               5                   10                  15
```

```
Thr Leu Thr Leu Thr Cys Thr Val Cys Gly Phe Ser Leu Ser Asn Pro
            20                  25                  30

Arg Met Gly Val Ser Trp Ile Arg Gln Pro Pro Gly Lys Ala Leu Glu
            35                  40                  45

Trp Leu Gly His Ile Phe Ser Ser Asp Glu Lys Ser Tyr Arg Leu Phe
 50                  55                  60

Leu Arg Ser Arg Leu Ser Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                85                  90                  95

Cys Ala Arg Asp Ser Ser Asp Tyr Glu Gly Tyr Phe Asp Tyr Trp Gly
            100                 105                 110

Gln Gly Thr Leu Val Thr Val Ser Ser
            115                 120

<210> SEQ ID NO 33
<211> LENGTH: 107
<212> TYPE: PRT
<213> ORGANISM: Artificial Sequence
<220> FEATURE:
<223> OTHER INFORMATION: Synthetic Construct

<400> SEQUENCE: 33

Glu Ile Val Met Thr Gln Ser Pro Ala Thr Leu Ser Val Ser Pro Gly
 1               5                  10                  15

Glu Arg Thr Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Ser Gly Val Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Ser Cys Gln Glu Tyr Asn Asn Trp Pro Phe
                85                  90                  95

Thr Phe Gly Gln Gly Thr Lys Val Glu Ile Lys
            100                 105

<210> SEQ ID NO 34
<211> LENGTH: 121
<212> TYPE: PRT
<213> ORGANISM: Artificial Sequence
<220> FEATURE:
<223> OTHER INFORMATION: Synthetic Construct

<400> SEQUENCE: 34

Gln Val Thr Leu Lys Glu Ser Gly Pro Val Leu Val Lys Pro Ile Glu
 1               5                  10                  15

Thr Leu Thr Leu Thr Cys Thr Val Cys Gly Phe Ser Leu Ser Asn Pro
            20                  25                  30

Arg Met Gly Val Ser Trp Ile Arg Gln Pro Pro Gly Lys Ala Leu Glu
            35                  40                  45

Trp Leu Gly His Ile Phe Ser Ser Asp Glu Lys Ser Tyr Arg Leu Phe
 50                  55                  60

Leu Arg Ser Arg Leu Ser Ile Ser Lys Asp Thr Ser Lys Ser Gln Val
 65                  70                  75                  80

Val Leu Thr Met Thr Asn Met Asp Pro Val Asp Thr Ala Thr Tyr Tyr
```

```
                    85                  90                  95
Cys Ala Arg Asp Ser Ser Asp Tyr Glu Gly Tyr Phe Asp Tyr Trp Gly
                100                 105                 110
Gln Gly Thr Leu Val Thr Val Ser Ser
        115                 120

<210> SEQ ID NO 35
<211> LENGTH: 121
<212> TYPE: PRT
<213> ORGANISM: Artificial Sequence
<220> FEATURE:
<223> OTHER INFORMATION: Synthetic Construct

<400> SEQUENCE: 35

Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Asn Pro
                20                  25                  30
Arg Met Gly Val Ser Trp Leu Arg Gln Pro Pro Gly Lys Ala Leu Glu
            35                  40                  45
Trp Phe Ala His Ile Phe Ser Thr Asp Glu Lys Ser Tyr Ser Pro Ser
    50                  55                  60
Leu Arg Gly Arg Leu Thr Val Ser Lys Asp Thr Ser Lys Ser Gln Val
65                  70                  75                  80
Val Leu Thr Leu Thr Asn Met Asp Pro Val Asp Thr Ala Thr Tyr Tyr
                85                  90                  95
Cys Ala Arg Asp Ser Ser Asn Tyr Glu Gly Tyr Phe Asp Tyr Trp Gly
                100                 105                 110
Gln Gly Thr Leu Val Thr Val Ser Ser
        115                 120

<210> SEQ ID NO 36
<211> LENGTH: 107
<212> TYPE: PRT
<213> ORGANISM: Artificial Sequence
<220> FEATURE:
<223> OTHER INFORMATION: Synthetic Construct

<400> SEQUENCE: 36

Lys Ile Val Met Thr Gln Ser Pro Ala Thr Leu Ser Val Ser Pro Gly
1               5                   10                  15
Glu Arg Ala Thr Leu Ser Cys Arg Ala Asn Gln Ile Val Ser Ser Asn
                20                  25                  30
Leu Ala Trp Tyr Gln Gln Lys Pro Gly Gln Ala Pro Arg Leu Leu Val
            35                  40                  45
Phe Gly Thr Ser Thr Arg Ala Thr Gly Ile Pro Ile Arg Phe Ser Gly
    50                  55                  60
Ser Gly Ser Gly Thr Glu Phe Thr Leu Thr Val Ser Ser Leu Gln Ser
65                  70                  75                  80
Glu Asp Phe Ala Val Tyr Val Cys Gln Gln Tyr Asn Asp Trp Pro Phe
                85                  90                  95
Thr Phe Gly Pro Gly Thr Lys Val Asp Ile Lys
                100                 105

<210> SEQ ID NO 37
<211> LENGTH: 118
<212> TYPE: PRT
<213> ORGANISM: Artificial Sequence
<220> FEATURE:
```

<223> OTHER INFORMATION: Synthetic Construct

<400> SEQUENCE: 37

Glu Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Asp Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Val Val
    50                  55                  60

Pro Leu Asn Gly Arg Phe Ile Ile Ser Arg Asp Asp Ser Arg Asn Thr
65                  70                  75                  80

Leu Tyr Leu Gln Leu Asn Asn Leu Lys Thr Glu Asp Thr Ala Val Tyr
                85                  90                  95

Tyr Cys Thr Thr Val Pro Gly Ser Tyr Gly Tyr Trp Gly Gln Gly Thr
            100                 105                 110

Leu Val Thr Val Ser Ser
        115

<210> SEQ ID NO 38
<211> LENGTH: 112
<212> TYPE: PRT
<213> ORGANISM: Artificial Sequence
<220> FEATURE:
<223> OTHER INFORMATION: Synthetic Construct

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Asn
            20                  25                  30

Lys Arg Asn Asn Tyr Leu Asp Trp Phe Leu Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Gln Gln Thr Pro Ile Thr Phe Gly Gln Gly Thr Arg Leu Glu Ile Lys
            100                 105                 110

<210> SEQ ID NO 39
<211> LENGTH: 120
<212> TYPE: PRT
<213> ORGANISM: Artificial Sequence
<220> FEATURE:
<223> OTHER INFORMATION: Synthetic Construct

<400> SEQUENCE: 39

Glu Val Asn Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Tyr Ala
            20                  25                  30

Trp Met Ser Trp Val Arg Gln Ala Pro Gly Lys Gly Leu Glu Trp Val
        35                  40                  45

Gly Arg Ile Lys Ser Ile Ala Asp Gly Gly Ala Thr Asp Tyr Ala Ala

```
                50                  55                  60
Pro Val Arg Asn Arg Phe Thr Ile Ser Arg Asp Asp Ser Arg Asn Thr
 65                  70                  75                  80

Leu Tyr Leu Glu Met His Ser Leu Lys Thr Glu Asp Thr Ala Val Tyr
                 85                  90                  95

Tyr Cys Thr Thr Ile Pro Gly Asn Asp Ala Phe Asp Met Trp Gly Gln
                100                 105                 110

Gly Thr Met Val Thr Val Ser Ser
            115                 120

<210> SEQ ID NO 40
<211> LENGTH: 112
<212> TYPE: PRT
<213> ORGANISM: Artificial Sequence
<220> FEATURE:
<223> OTHER INFORMATION: Synthetic Construct

<400> SEQUENCE: 40

Asp Ile Val Leu Thr Gln Ser Pro Leu Ser Leu Ser Val Thr Pro Gly
  1               5                  10                  15

Glu Pro Ala Ser Ile Ser Cys Arg Ser Ser Gln Ser Leu Leu Tyr Ser
                 20                  25                  30

Asn Gly Lys Asn Tyr Leu Asp Trp Phe Leu His Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Ile Asp Phe Ile Leu Lys Ile
 65                  70                  75                  80

Ser Arg Val Glu Ala Glu Asp Val Gly Val Tyr Tyr Cys Met Gln Ala
                 85                  90                  95

Gln Gln Thr Pro Ile Thr Phe Gly Gln Gly Thr Arg Leu Glu Ile Lys
                100                 105                 110

<210> SEQ ID NO 41
<211> LENGTH: 119
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Glu Ser Trp Gly Val Leu Val Lys Pro Gly Gly
  1               5                  10                  15

Ser Leu Arg Leu Ser Cys Ala Ala Ser Gly Phe Ile Phe Asn Asn Ala
                 20                  25                  30

Trp Met Ser Trp Val Arg Gln Ala Pro Gly Lys Gly Leu Glu Trp Ile
             35                  40                  45

Gly Arg Ile Lys Ser Lys Ser Asp Gly Gly Thr Thr Asp Tyr Ala Ala
         50                  55                  60

Pro Val Lys Asp Arg Phe Thr Ile Ser Arg Asp Asp Ser Lys Asp Thr
 65                  70                  75                  80

Leu Tyr Leu Gln Met Asn Gly Leu Lys Thr Glu Asp Thr Ala Val Tyr
                 85                  90                  95

Phe Cys Thr Thr Ala Pro Gly Gly Pro Phe Asp Tyr Trp Gly Gln Gly
                100                 105                 110

Thr Leu Val Thr Val Ser Ser
            115
```

```
<210> SEQ ID NO 42
<211> LENGTH: 112
<212> TYPE: PRT
<213> ORGANISM: Artificial Sequence
<220> FEATURE:
<223> OTHER INFORMATION: Synthetic Construct

<400> SEQUENCE: 42

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asp Gly Phe Asn Tyr Leu Asp Trp Phe Leu Gln Lys Pro Gly Gln Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Asp Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 43
<211> LENGTH: 120
<212> TYPE: PRT
<213> ORGANISM: Artificial Sequence
<220> FEATURE:
<223> OTHER INFORMATION: Synthetic Construct

<400> SEQUENCE: 43

Glu Val Asn Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Tyr Ala
            20                  25                  30

Trp Met Ser Trp Val Arg Gln Ala Pro Gly Lys Gly Leu Glu Trp Val
        35                  40                  45

Gly Arg Ile Lys Ser Ile Thr Asp Gly Gly Val Ile Asp Tyr Ala Ala
    50                  55                  60

Pro Val Arg Asn Arg Cys Thr Ile Ser Arg Asp Asp Ser Arg Asn Thr
65                  70                  75                  80

Leu Tyr Leu Glu Met His Ser Leu Lys Thr Glu Asp Thr Ala Val Tyr
                85                  90                  95

Tyr Cys Thr Thr Ile Pro Gly Asn Asp Asp Phe Asp Met Trp Gly Gln
            100                 105                 110

Gly Arg Met Val Thr Val Ser Ser
        115                 120

<210> SEQ ID NO 44
<211> LENGTH: 120
<212> TYPE: PRT
<213> ORGANISM: Artificial Sequence
<220> FEATURE:
<223> OTHER INFORMATION: Synthetic Construct

<400> SEQUENCE: 44

Glu Val Asn Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Tyr Ala
```

```
            20                  25                  30
Trp Met Ser Trp Val Arg Gln Ala Pro Gly Lys Gly Leu Glu Trp Val
        35                  40                  45

Gly Arg Ile Lys Ser Ile Asn Asp Gly Gly Ala Thr Asp Tyr Ala Ser
    50                  55                  60

Pro Val Arg Asn Arg Phe Thr Ile Ser Arg Asp Asp Ser Arg Asn Met
65                  70                  75                  80

Leu Tyr Leu Glu Met His Ser Leu Lys Thr Glu Asp Thr Ala Val Tyr
                85                  90                  95

Tyr Cys Thr Thr Ile Pro Gly Asn Asp Ala Phe Asp Met Trp Gly Gln
            100                 105                 110

Gly Thr Leu Val Thr Val Ser Ser
            115                 120
```

<210> SEQ ID NO 45
<211> LENGTH: 112
<212> TYPE: PRT
<213> ORGANISM: Artificial Sequence
<220> FEATURE:
<223> OTHER INFORMATION: Synthetic Construct

<400> SEQUENCE: 45

```
Asp Ile Val Leu Thr Gln Ser Pro Leu Ser Leu Ser Val Thr Pro Gly
1               5                   10                  15

Glu Pro Ala Ser Ile Ser Cys Arg Ser Thr Gln Ser Leu Leu Tyr Ser
            20                  25                  30

Asn Gly Lys Asn Tyr Leu Asp Trp Phe Leu His Lys Pro Gly Gln Ser
        35                  40                  45

Pro Gln Leu Leu Ile Phe Leu Gly Ser Ile Arg Ala Ser Gly Val Pro
    50                  55                  60

Asp Arg Phe Ser Gly Ser Gly Ser Gly Ile Asp Phe Ile Leu Lys Ile
65                  70                  75                  80

Ser Arg Val Glu Ala Glu Asp Val Gly Val Tyr Tyr Cys Met Gln Ala
                85                  90                  95

Gln Gln Thr Pro Ile Thr Phe Gly Gln Gly Thr Arg Leu Glu Ile Lys
            100                 105                 110
```

<210> SEQ ID NO 46
<211> LENGTH: 119
<212> TYPE: PRT
<213> ORGANISM: Artificial Sequence
<220> FEATURE:
<223> OTHER INFORMATION: Synthetic Construct

<400> SEQUENCE: 46

```
Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Thr Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Ile Asp Gly Gly Thr Thr Asp Tyr Ala Ala
    50                  55                  60

Pro Val Lys Gly Arg Phe Ile Ile Ser Arg Asp Asp Ser Lys Asn Thr
65                  70                  75                  80

Leu Ser Leu Gln Met Asn Ser Leu Lys Thr Glu Asp Thr Ala Met Tyr
                85                  90                  95
```

```
Tyr Cys Thr Thr Ala Pro Gly Gly Pro Phe Asp Tyr Trp Gly Gln Gly
            100                 105                 110

Ser Leu Val Thr Val Ser Ser
        115
```

<210> SEQ ID NO 47
<211> LENGTH: 112
<212> TYPE: PRT
<213> ORGANISM: Artificial Sequence
<220> FEATURE:
<223> OTHER INFORMATION: Synthetic Construct

<400> SEQUENCE: 47

```
Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asp Arg Arg Asn Tyr Leu Asp Trp Phe Leu Gln Lys Pro Gly Gln Ser
        35                  40                  45

Pro His Leu Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ile Pro Ile Thr Phe Gly Gln Gly Thr Arg Leu Glu Ile Lys
            100                 105                 110
```

<210> SEQ ID NO 48
<211> LENGTH: 126
<212> TYPE: PRT
<213> ORGANISM: Artificial Sequence
<220> FEATURE:
<223> OTHER INFORMATION: Synthetic Construct

<400> SEQUENCE: 48

```
Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Asn
            20                  25                  30

Ala Ile Ser Trp Val Arg Gln Ala Pro Gly Gln Gly Leu Glu Trp Met
        35                  40                  45

Gly Val Ile Ile Pro Ile Phe Gly Thr Ala Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Thr Tyr His Glu Tyr Ala Gly Gly Tyr Tyr Gly Gly Ala
            100                 105                 110

Met Asp Pro Trp Gly Gln Gly Thr Leu Val Thr Val Ser Ser
        115                 120                 125
```

<210> SEQ ID NO 49
<211> LENGTH: 112
<212> TYPE: PRT
<213> ORGANISM: Artificial Sequence
<220> FEATURE:
<223> OTHER INFORMATION: Synthetic Construct

```
<400> SEQUENCE: 49

Glu Leu Gln Ser Val Leu Thr Gln Pro Pro Ser Ala Ser Gly Thr Pro
1               5                   10                  15

Gly Gln Arg Val Thr Ile Ser Cys Ser Gly Ser Ser Ser Asn Ile Gly
            20                  25                  30

Ser Asn Tyr Val Tyr Trp Tyr Gln Gln Leu Pro Gly Thr Ala Pro Lys
        35                  40                  45

Ile Leu Ile Tyr Arg Asn Asn Gln Arg Pro Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Arg Ser Glu Asp Glu Ala Asp Tyr Tyr Cys Ala Ala Trp Asp Asp
                85                  90                  95

Asn Leu Ser Gly Trp Val Phe Gly Thr Gly Thr Lys Leu Thr Val Leu
            100                 105                 110

<210> SEQ ID NO 50
<211> LENGTH: 123
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Asp Ile Ser Gly Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Tyr Gly Gly Val Tyr Pro Met Asp Ile
            100                 105                 110

Trp Gly Gln Gly Thr Leu Val Thr Val Ser Ser
        115                 120

<210> SEQ ID NO 51
<211> LENGTH: 107
<212> TYPE: PRT
<213> ORGANISM: Artificial Sequence
<220> FEATURE:
<223> OTHER INFORMATION: Synthetic Construct

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys
            100                 105

<210> SEQ ID NO 52
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 52

Gln Val Thr Leu Lys Glu Ser Gly Pro Val Leu Leu Lys Pro Thr Glu
 1               5                  10                  15

Thr Leu Thr Leu Thr Cys Thr Val Ser Gly Phe Ser Leu Ser Asn Pro
                 20                  25                  30

Arg Met Gly Val Ser Trp Ile Arg Gln Pro Pro Gly Lys Ala Leu Glu
             35                  40                  45

Trp Phe Ala His Ile Phe Ser Thr Asp Glu Lys Ser Leu Lys Leu Ser
 50                  55                  60

Leu Arg Ser Arg Leu Thr Leu Ser Lys Asp Thr Ser Lys Ser Gln Val
 65                  70                  75                  80

Val Leu Thr Met Thr Asn Met Ala Pro Val Asp Ser Ala Thr Tyr Tyr
                 85                  90                  95

Cys Ala Arg Xaa Xaa Ser Asn Tyr Glu Gly Tyr Phe Asp Phe Trp Gly
            100                 105                 110

Gln Gly Thr Leu Val Thr Val Ser Ser
        115                 120

<210> SEQ ID NO 53
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 53

Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Asn Ala
                 20                  25                  30

Arg Met Gly Val Ser Trp Ile Arg Gln Pro Pro Gly Lys Ala Leu Glu
             35                  40                  45

Trp Leu Ala His Ile Phe Ser Thr Asp Glu Lys Ser Ile Arg Arg Ser
 50                  55                  60

Leu Arg Ser Arg Leu Thr Leu Ser Lys Asp Thr Ser Lys Ser Gln Val
 65                  70                  75                  80

Val Leu Thr Met Thr Asn Met Asp Pro Val Asp Thr Ala Thr Tyr Phe
                 85                  90                  95
```

Cys Ala Arg Xaa Xaa Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 54
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 54

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Gly His Ile Phe Ser Thr Asp Glu Lys Ser Tyr Ser Thr Ser
    50                  55                  60

Leu Arg Gly Arg Ile Thr Ile Ser Lys Asp Thr Ser Arg Gly Leu Val
65                  70                  75                  80

Val Leu Thr Leu Thr Asn Met Asp Pro Val Asp Thr Ala Thr Tyr Tyr
                85                  90                  95

Cys Ala Arg Xaa Xaa Ser Asn Tyr Glu Gly Tyr Phe Asp Phe Trp Gly
            100                 105                 110

Pro Gly Phe Leu Val Thr Val Ser Ser
        115                 120

<210> SEQ ID NO 55
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 55

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Met Gly Val Ser Trp Ile Arg Gln Pro Pro Gly Lys Ala Leu Glu
        35                  40                  45

Trp Phe Ala His Ile Phe Ser Thr Asp Glu Lys Ser Phe Arg Thr Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Ser Asn Tyr Glu Gly Tyr Phe Asp Tyr Trp Gly
            100                 105                 110

Gln Gly Ile Leu Val Thr Val Ser Ser
        115                 120

<210> SEQ ID NO 56
<211> LENGTH: 122
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 56

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Val
            20                  25                  30

Arg Met Gly Val Ser Trp Ile Arg Gln Pro Pro Gly Lys Ala Leu Glu
        35                  40                  45

Trp Phe Ala His Ile Phe Ser Ser Asp Glu Lys Ser Ile Arg Arg Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Ser Asn Tyr Glu Gly Tyr Phe Asp Phe Trp Gly
            100                 105                 110

Gln Gly Thr Leu Val Thr Val Ser Ser Asn
        115                 120

<210> SEQ ID NO 57
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 57

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Val
            20                  25                  30

Arg Met Gly Val Ser Trp Ile Arg Gln Pro Pro Gly Lys Ala Leu Glu
        35                  40                  45

Trp Phe Ala His Ile Phe Ser Ser Asp Glu Lys Ser Ile Arg Arg Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Ser Asn Tyr Glu Gly Tyr Phe Asp Tyr Trp Gly
            100                 105                 110

Gln Gly Thr Leu Val Thr Val Ser Ser
        115                 120

```
<210> SEQ ID NO 58
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 58

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Thr Asp Glu Lys Ser Ile Arg Arg Ser
    50                  55                  60

Leu Arg Ser Arg Leu Thr Leu Ser Lys Asp Thr Ser Lys Ser Gln Val
65                  70                  75                  80

Val Leu Ile Met Thr Asn Met Asp Pro Val Asp Thr Ala Thr Tyr Tyr
                85                  90                  95

Cys Ala Arg Xaa Xaa Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 59
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 59

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Thr Asp Glu Lys Ser Ile Arg Arg Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 60
<211> LENGTH: 121
```

<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 60

```
Gln Val Thr Leu Glu Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Pro Glu
        35                  40                  45

Trp Phe Ala His Ile Phe Ser Thr Asp Glu Lys Ser Leu Arg Leu Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Ser Asn Tyr Glu Gly Tyr Phe Asp Tyr Trp Gly
            100                 105                 110

Gln Gly Thr Leu Val Thr Val Ser Ser
        115                 120
```

<210> SEQ ID NO 61
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 61

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Lys Met Gly Val Ser Trp Ile Arg Gln Pro Pro Gly Lys Ala Leu Glu
        35                  40                  45

Trp Leu Ala His Ile Phe Ser Thr Asp Glu Lys Ser Ile Arg Arg Ser
    50                  55                  60

Leu Arg Ser Arg Leu Thr Met Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Xaa Xaa Ser Asn Tyr Glu Gly Tyr Phe Asp Tyr Trp Gly
            100                 105                 110

Gln Gly Thr Leu Val Thr Val Ser Ser
        115                 120
```

<210> SEQ ID NO 62
<211> LENGTH: 6
<212> TYPE: PRT
<213> ORGANISM: Artificial Sequence
<220> FEATURE:

<223> OTHER INFORMATION: Synthetic Construct

<400> SEQUENCE: 62

Thr Asp Tyr Thr Leu His
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic Construct

<400> SEQUENCE: 63

Gly Tyr Thr Phe Thr Asp
1               5

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Gly Tyr Thr Phe Thr Asp Tyr Thr Leu His
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Synthetic Construct

<400> SEQUENCE: 65

Gly Ile Asp Pro Ile Asn Gly Gly Thr Thr Tyr Asn Gln Lys Phe Lys
1               5                   10                  15

Gly

<210> SEQ ID NO 66
<211> LENGTH: 11
<212> TYPE: PRT
<213> ORGANISM: Artificial Sequence
<220> FEATURE:
<223> OTHER INFORMATION: Synthetic Construct

<400> SEQUENCE: 66

Gly Ile Asp Pro Ile Asn Gly Gly Thr Thr Tyr
1               5                   10

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct

<400> SEQUENCE: 67

Gly Glu Ala Met Asp Ser
1               5

<210> SEQ ID NO 68
<211> LENGTH: 17
<212> TYPE: PRT
<213> ORGANISM: Artificial Sequence

```
<220> FEATURE:
<223> OTHER INFORMATION: Synthetic Construct

<400> SEQUENCE: 68

Gly Ile Asn Pro Ile Asn Gly Gly Thr Thr Tyr Asn Gln Lys Phe Lys
1               5                   10                  15

Gly

<210> SEQ ID NO 69
<211> LENGTH: 11
<212> TYPE: PRT
<213> ORGANISM: Artificial Sequence
<220> FEATURE:
<223> OTHER INFORMATION: Synthetic Construct

<400> SEQUENCE: 69

Gly Ile Asn Pro Ile Asn Gly Gly Thr Thr Tyr
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Synthetic Construct

<400> SEQUENCE: 70

Gly Ile Trp Pro Ile Thr Gly Gly Thr Thr Tyr Asn Gln Lys Phe Lys
1               5                   10                  15

Gly

<210> SEQ ID NO 71
<211> LENGTH: 11
<212> TYPE: PRT
<213> ORGANISM: Artificial Sequence
<220> FEATURE:
<223> OTHER INFORMATION: Synthetic Construct

<400> SEQUENCE: 71

Gly Ile Trp Pro Ile Thr Gly Gly Thr Thr Tyr
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic Construct

<400> SEQUENCE: 72

Gly Ile Trp Pro Ile Thr Gly Gly Thr Thr Tyr
1               5                   10

<210> SEQ ID NO 73
<211> LENGTH: 6
<212> TYPE: PRT
<213> ORGANISM: Artificial Sequence
<220> FEATURE:
<223> OTHER INFORMATION: Synthetic Construct

<400> SEQUENCE: 73

Gly Glu Ala Gln Gly Ser
1               5

<210> SEQ ID NO 74
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 74

Ser Asn Pro Arg Met Gly Val Ser
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct

<400> SEQUENCE: 75

Gly Phe Ser Leu Ser Asn Pro Arg
1               5

<210> SEQ ID NO 76
<211> LENGTH: 12
<212> TYPE: PRT
<213> ORGANISM: Artificial Sequence
<220> FEATURE:
<223> OTHER INFORMATION: Synthetic Construct

<400> SEQUENCE: 76

Gly Phe Ser Leu Ser Asn Pro Arg Met Gly Val Ser
1               5                   10

<210> SEQ ID NO 77
<211> LENGTH: 16
<212> TYPE: PRT
<213> ORGANISM: Artificial Sequence
<220> FEATURE:
<223> OTHER INFORMATION: Synthetic Construct

<400> SEQUENCE: 77

His Ile Phe Ser Thr Asp Glu Lys Ser Leu Lys Leu Ser Leu Arg Ser
1               5                   10                  15

<210> SEQ ID NO 78
<211> LENGTH: 10
<212> TYPE: PRT
<213> ORGANISM: Artificial Sequence
<220> FEATURE:
<223> OTHER INFORMATION: Synthetic Construct

<400> SEQUENCE: 78

His Ile Phe Ser Thr Asp Glu Lys Ser Leu
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

Asp Ser Ser Asn Tyr Glu Gly Tyr Phe Asp Phe
1               5                   10

<210> SEQ ID NO 80
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 80

Ser Asn Ala Arg Met Gly Val Ser
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct

<400> SEQUENCE: 81

Gly Phe Ser Leu Ser Asn Ala Arg
1               5

<210> SEQ ID NO 82
<211> LENGTH: 12
<212> TYPE: PRT
<213> ORGANISM: Artificial Sequence
<220> FEATURE:
<223> OTHER INFORMATION: Synthetic Construct

<400> SEQUENCE: 82

Gly Phe Ser Leu Ser Asn Ala Arg Met Gly Val Ser
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Synthetic Construct

<400> SEQUENCE: 83

His Ile Phe Ser Thr Asp Glu Lys Ser Ile Arg Arg Ser Leu Arg Ser
1               5                   10                  15

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct

<400> SEQUENCE: 84

His Ile Phe Ser Thr Asp Glu Lys Ser Ile
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic Construct

<400> SEQUENCE: 85

Asp Ser Ser Asn Tyr Glu Gly Tyr Phe Asp Tyr
1               5                   10

<210> SEQ ID NO 86
<211> LENGTH: 16
<212> TYPE: PRT
```

<213> ORGANISM: Artificial Sequence
<220> FEATURE:
<223> OTHER INFORMATION: Synthetic Construct

<400> SEQUENCE: 86

His Ile Phe Ser Thr Asp Glu Lys Ser Tyr Ser Thr Ser Leu Arg Gly
1               5                   10                  15

<210> SEQ ID NO 87
<211> LENGTH: 10
<212> TYPE: PRT
<213> ORGANISM: Artificial Sequence
<220> FEATURE:
<223> OTHER INFORMATION: Synthetic Construct

<400> SEQUENCE: 87

His Ile Phe Ser Thr Asp Glu Lys Ser Tyr
1               5                   10

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct

<400> SEQUENCE: 88

Asn Asn Ala Arg Met Gly Val Ser
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic Construct

<400> SEQUENCE: 89

Gly Phe Ser Leu Asn Asn Ala Arg
1               5

<210> SEQ ID NO 90
<211> LENGTH: 12
<212> TYPE: PRT
<213> ORGANISM: Artificial Sequence
<220> FEATURE:
<223> OTHER INFORMATION: Synthetic Construct

<400> SEQUENCE: 90

Gly Phe Ser Leu Asn Asn Ala Arg Met Gly Val Ser
1               5                   10

<210> SEQ ID NO 91
<211> LENGTH: 16
<212> TYPE: PRT
<213> ORGANISM: Artificial Sequence
<220> FEATURE:
<223> OTHER INFORMATION: Synthetic Construct

<400> SEQUENCE: 91

His Ile Phe Ser Thr Asp Glu Lys Ser Phe Arg Thr Ser Leu Arg Ser
1               5                   10                  15

<210> SEQ ID NO 92
<211> LENGTH: 10
<212> TYPE: PRT
<213> ORGANISM: Artificial Sequence

```
<220> FEATURE:
<223> OTHER INFORMATION: Synthetic Construct

<400> SEQUENCE: 92

His Ile Phe Ser Thr Asp Glu Lys Ser Phe
1               5                   10

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct

<400> SEQUENCE: 93

Ser Asn Val Arg Met Gly Val Ser
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Gly Phe Ser Leu Ser Asn Val Arg
1               5

<210> SEQ ID NO 95
<211> LENGTH: 12
<212> TYPE: PRT
<213> ORGANISM: Artificial Sequence
<220> FEATURE:
<223> OTHER INFORMATION: Synthetic Construct

<400> SEQUENCE: 95

Gly Phe Ser Leu Ser Asn Val Arg Met Gly Val Ser
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Synthetic Construct

<400> SEQUENCE: 96

His Ile Phe Ser Ser Asp Glu Lys Ser Ile Arg Arg Ser Leu Arg Ser
1               5                   10                  15

<210> SEQ ID NO 97
<211> LENGTH: 10
<212> TYPE: PRT
<213> ORGANISM: Artificial Sequence
<220> FEATURE:
<223> OTHER INFORMATION: Synthetic Construct

<400> SEQUENCE: 97

His Ile Phe Ser Ser Asp Glu Lys Ser Ile
1               5                   10

<210> SEQ ID NO 98
<211> LENGTH: 16
<212> TYPE: PRT
<213> ORGANISM: Artificial Sequence
<220> FEATURE:
```

<223> OTHER INFORMATION: Synthetic Construct

<400> SEQUENCE: 98

His Ile Phe Ser Thr Asp Glu Lys Ser Leu Arg Leu Ser Leu Arg Ser
1               5                   10                  15

<210> SEQ ID NO 99
<211> LENGTH: 8
<212> TYPE: PRT
<213> ORGANISM: Artificial Sequence
<220> FEATURE:
<223> OTHER INFORMATION: Synthetic Construct

<400> SEQUENCE: 99

Ser Asn Ala Lys Met Gly Val Ser
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Construct

<400> SEQUENCE: 100

Gly Phe Ser Leu Ser Asn Ala Lys
1               5

<210> SEQ ID NO 101
<211> LENGTH: 12
<212> TYPE: PRT
<213> ORGANISM: Artificial Sequence
<220> FEATURE:
<223> OTHER INFORMATION: Synthetic Construct

<400> SEQUENCE: 101

Gly Phe Ser Leu Ser Asn Ala Lys Met Gly Val Ser
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Synthetic Construct

<400> SEQUENCE: 102

His Ile Phe Ser Ser Asp Glu Lys Ser Tyr Arg Leu Ser Leu Arg Ser
1               5                   10                  15

<210> SEQ ID NO 103
<211> LENGTH: 10
<212> TYPE: PRT
<213> ORGANISM: Artificial Sequence
<220> FEATURE:
<223> OTHER INFORMATION: Synthetic Construct

<400> SEQUENCE: 103

His Ile Phe Ser Ser Asp Glu Lys Ser Tyr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic Construct

```
<400> SEQUENCE: 104

Asp Ser Ser Asn Tyr Gly Gly Tyr Phe Asp Tyr
1               5                   10

<210> SEQ ID NO 105
<211> LENGTH: 16
<212> TYPE: PRT
<213> ORGANISM: Artificial Sequence
<220> FEATURE:
<223> OTHER INFORMATION: Synthetic Construct

<400> SEQUENCE: 105

His Ile Phe Ser Ser Asp Glu Lys Ser Tyr Arg Leu Phe Leu Arg Ser
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Synthetic Construct

<400> SEQUENCE: 106

His Ile Phe Ser Thr Asp Glu Lys Ser Tyr Ser Pro Ser Leu Arg Gly
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Synthetic Construct

<400> SEQUENCE: 107

Asp Ser Ser Asp Tyr Glu Gly Tyr Phe Asp Tyr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic Construct

<400> SEQUENCE: 108

Asp Ser Ser Asn Tyr Glu Glu Tyr Phe Asp Tyr
1               5                   10

<210> SEQ ID NO 109
<211> LENGTH: 6
<212> TYPE: PRT
<213> ORGANISM: Artificial Sequence
<220> FEATURE:
<223> OTHER INFORMATION: Synthetic Construct

<400> SEQUENCE: 109

Ser Asp Ala Trp Met Ser
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 110

Gly Phe Thr Phe Ser Asp
1               5

<210> SEQ ID NO 111
<211> LENGTH: 10
<212> TYPE: PRT
<213> ORGANISM: Artificial Sequence
<220> FEATURE:
<223> OTHER INFORMATION: Synthetic Construct

<400> SEQUENCE: 111

Gly Phe Thr Phe Ser Asp Ala Trp Met Ser
1               5                   10

<210> SEQ ID NO 112
<211> LENGTH: 19
<212> TYPE: PRT
<213> ORGANISM: Artificial Sequence
<220> FEATURE:
<223> OTHER INFORMATION: Synthetic Construct

<400> SEQUENCE: 112

Arg Ile Lys Ser Lys Thr Asp Gly Gly Thr Thr Asp Tyr Val Val Pro
1               5                   10                  15
Leu Asn Gly

<210> SEQ ID NO 113
<211> LENGTH: 13
<212> TYPE: PRT
<213> ORGANISM: Artificial Sequence
<220> FEATURE:
<223> OTHER INFORMATION: Synthetic Construct

<400> SEQUENCE: 113

Arg Ile Lys Ser Lys Thr Asp Gly Gly Thr Thr Asp Tyr
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Synthetic Construct

<400> SEQUENCE: 114

Val Pro Gly Ser Tyr Gly Tyr
1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic Construct

<400> SEQUENCE: 115

Ser Tyr Ala Trp Met Ser
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 116

Gly Phe Thr Phe Ser Tyr
1               5

<210> SEQ ID NO 117
<211> LENGTH: 10
<212> TYPE: PRT
<213> ORGANISM: Artificial Sequence
<220> FEATURE:
<223> OTHER INFORMATION: Synthetic Construct

<400> SEQUENCE: 117

Gly Phe Thr Phe Ser Tyr Ala Trp Met Ser
1               5                   10

<210> SEQ ID NO 118
<211> LENGTH: 19
<212> TYPE: PRT
<213> ORGANISM: Artificial Sequence
<220> FEATURE:
<223> OTHER INFORMATION: Synthetic Construct

<400> SEQUENCE: 118

Arg Ile Lys Ser Ile Ala Asp Gly Gly Ala Thr Asp Tyr Ala Ala Pro
1               5                   10                  15

Val Arg Asn

<210> SEQ ID NO 119
<211> LENGTH: 13
<212> TYPE: PRT
<213> ORGANISM: Artificial Sequence
<220> FEATURE:
<223> OTHER INFORMATION: Synthetic Construct

<400> SEQUENCE: 119

Arg Ile Lys Ser Ile Ala Asp Gly Gly Ala Thr Asp Tyr
1               5                   10

<210> SEQ ID NO 120
<211> LENGTH: 9
<212> TYPE: PRT
<213> ORGANISM: Artificial Sequence
<220> FEATURE:
<223> OTHER INFORMATION: Synthetic Construct

<400> SEQUENCE: 120

Ile Pro Gly Asn Asp Ala Phe Asp Met
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic Construct

<400> SEQUENCE: 121

Asn Asn Ala Trp Met Ser
1               5

<210> SEQ ID NO 122
<211> LENGTH: 6
<212> TYPE: PRT
<213> ORGANISM: Artificial Sequence
<220> FEATURE:
```

```
<223> OTHER INFORMATION: Synthetic Construct

<400> SEQUENCE: 122

Gly Phe Ile Phe Asn Asn
1               5

<210> SEQ ID NO 123
<211> LENGTH: 10
<212> TYPE: PRT
<213> ORGANISM: Artificial Sequence
<220> FEATURE:
<223> OTHER INFORMATION: Synthetic Construct

<400> SEQUENCE: 123

Gly Phe Ile Phe Asn Asn Ala Trp Met Ser
1               5                   10

<210> SEQ ID NO 124
<211> LENGTH: 19
<212> TYPE: PRT
<213> ORGANISM: Artificial Sequence
<220> FEATURE:
<223> OTHER INFORMATION: Synthetic Construct

<400> SEQUENCE: 124

Arg Ile Lys Ser Lys Ser Asp Gly Gly Thr Thr Asp Tyr Ala Ala Pro
1               5                   10                  15

Val Lys Asp

<210> SEQ ID NO 125
<211> LENGTH: 13
<212> TYPE: PRT
<213> ORGANISM: Artificial Sequence
<220> FEATURE:
<223> OTHER INFORMATION: Synthetic Construct

<400> SEQUENCE: 125

Arg Ile Lys Ser Lys Ser Asp Gly Gly Thr Thr Asp Tyr
1               5                   10

<210> SEQ ID NO 126
<211> LENGTH: 8
<212> TYPE: PRT
<213> ORGANISM: Artificial Sequence
<220> FEATURE:
<223> OTHER INFORMATION: Synthetic Construct

<400> SEQUENCE: 126

Ala Pro Gly Gly Pro Phe Asp Tyr
1               5

<210> SEQ ID NO 127
<211> LENGTH: 19
<212> TYPE: PRT
<213> ORGANISM: Artificial Sequence
<220> FEATURE:
<223> OTHER INFORMATION: Synthetic Construct

<400> SEQUENCE: 127

Arg Ile Lys Ser Ile Thr Asp Gly Gly Val Ile Asp Tyr Ala Ala Pro
1               5                   10                  15

Val Arg Asn

<210> SEQ ID NO 128
<211> LENGTH: 13
```

```
<212> TYPE: PRT
<213> ORGANISM: Artificial Sequence
<220> FEATURE:
<223> OTHER INFORMATION: Synthetic Construct

<400> SEQUENCE: 128

Arg Ile Lys Ser Ile Thr Asp Gly Gly Val Ile Asp Tyr
1               5                   10

<210> SEQ ID NO 129
<211> LENGTH: 9
<212> TYPE: PRT
<213> ORGANISM: Artificial Sequence
<220> FEATURE:
<223> OTHER INFORMATION: Synthetic Construct

<400> SEQUENCE: 129

Ile Pro Gly Asn Asp Asp Phe Asp Met
1               5

<210> SEQ ID NO 130
<211> LENGTH: 19
<212> TYPE: PRT
<213> ORGANISM: Artificial Sequence
<220> FEATURE:
<223> OTHER INFORMATION: Synthetic Construct

<400> SEQUENCE: 130

Arg Ile Lys Ser Ile Asn Asp Gly Gly Ala Thr Asp Tyr Ala Ser Pro
1               5                   10                  15

Val Arg Asn

<210> SEQ ID NO 131
<211> LENGTH: 13
<212> TYPE: PRT
<213> ORGANISM: Artificial Sequence
<220> FEATURE:
<223> OTHER INFORMATION: Synthetic Construct

<400> SEQUENCE: 131

Arg Ile Lys Ser Ile Asn Asp Gly Gly Ala Thr Asp Tyr
1               5                   10

<210> SEQ ID NO 132
<211> LENGTH: 6
<212> TYPE: PRT
<213> ORGANISM: Artificial Sequence
<220> FEATURE:
<223> OTHER INFORMATION: Synthetic Construct

<400> SEQUENCE: 132

Thr Asn Ala Trp Met Ser
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic Construct

<400> SEQUENCE: 133

Gly Phe Thr Phe Thr Asn
1               5

<210> SEQ ID NO 134
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 134

Gly Phe Thr Phe Thr Asn Ala Trp Met Ser
1               5                   10

<210> SEQ ID NO 135
<211> LENGTH: 19
<212> TYPE: PRT
<213> ORGANISM: Artificial Sequence
<220> FEATURE:
<223> OTHER INFORMATION: Synthetic Construct

<400> SEQUENCE: 135

Arg Ile Lys Ser Lys Ile Asp Gly Gly Thr Thr Asp Tyr Ala Ala Pro
1               5                   10                  15

Val Lys Gly

<210> SEQ ID NO 136
<211> LENGTH: 13
<212> TYPE: PRT
<213> ORGANISM: Artificial Sequence
<220> FEATURE:
<223> OTHER INFORMATION: Synthetic Construct

<400> SEQUENCE: 136

Arg Ile Lys Ser Lys Ile Asp Gly Gly Thr Thr Asp Tyr
1               5                   10

<210> SEQ ID NO 137
<211> LENGTH: 6
<212> TYPE: PRT
<213> ORGANISM: Artificial Sequence
<220> FEATURE:
<223> OTHER INFORMATION: Synthetic Consturct

<400> SEQUENCE: 137

Ser Ser Asn Ala Ile Ser
1               5

<210> SEQ ID NO 138
<211> LENGTH: 6
<212> TYPE: PRT
<213> ORGANISM: Artificial Sequence
<220> FEATURE:
<223> OTHER INFORMATION: Synthetic Consturct

<400> SEQUENCE: 138

Gly Asp Thr Phe Ser Ser
1               5

<210> SEQ ID NO 139
<211> LENGTH: 10
<212> TYPE: PRT
<213> ORGANISM: Artificial Sequence
<220> FEATURE:
<223> OTHER INFORMATION: Synthetic Consturct

<400> SEQUENCE: 139

Gly Asp Thr Phe Ser Ser Asn Ala Ile Ser
1               5                   10
```

```
<210> SEQ ID NO 140
<211> LENGTH: 17
<212> TYPE: PRT
<213> ORGANISM: Artificial Sequence
<220> FEATURE:
<223> OTHER INFORMATION: Synthetic Consturct

<400> SEQUENCE: 140

Val Ile Ile Pro Ile Phe Gly Thr Ala Asp Tyr Ala Gln Lys Phe Gln
1               5                   10                  15

Gly

<210> SEQ ID NO 141
<211> LENGTH: 11
<212> TYPE: PRT
<213> ORGANISM: Artificial Sequence
<220> FEATURE:
<223> OTHER INFORMATION: Synthetic Consturct

<400> SEQUENCE: 141

Val Ile Ile Pro Ile Phe Gly Thr Ala Asp Tyr
1               5                   10

<210> SEQ ID NO 142
<211> LENGTH: 17
<212> TYPE: PRT
<213> ORGANISM: Artificial Sequence
<220> FEATURE:
<223> OTHER INFORMATION: Synthetic Consturct

<400> SEQUENCE: 142

His Thr Tyr His Glu Tyr Ala Gly Gly Tyr Tyr Gly Gly Ala Met Asp
1               5                   10                  15

Pro

<210> SEQ ID NO 143
<211> LENGTH: 6
<212> TYPE: PRT
<213> ORGANISM: Artificial Sequence
<220> FEATURE:
<223> OTHER INFORMATION: Synthetic Consturct

<400> SEQUENCE: 143

Ser Asn Tyr Ala Met Ser
1               5

<210> SEQ ID NO 144
<211> LENGTH: 6
<212> TYPE: PRT
<213> ORGANISM: Artificial Sequence
<220> FEATURE:
<223> OTHER INFORMATION: Synthetic Construct

<400> SEQUENCE: 144

Gly Phe Thr Phe Ser Asn
1               5

<210> SEQ ID NO 145
<211> LENGTH: 10
<212> TYPE: PRT
<213> ORGANISM: Artificial Sequence
<220> FEATURE:
<223> OTHER INFORMATION: Synthetic Construct

<400> SEQUENCE: 145

Gly Phe Thr Phe Ser Asn Tyr Ala Met Ser
```

```
<210> SEQ ID NO 146
<211> LENGTH: 17
<212> TYPE: PRT
<213> ORGANISM: Artificial Sequence
<220> FEATURE:
<223> OTHER INFORMATION: Synthetic Construct

<400> SEQUENCE: 146

Asp Ile Ser Gly Gly Gly Gly Arg Thr Tyr Tyr Ala Asp Ser Val Lys
1               5                   10                  15
Gly

<210> SEQ ID NO 147
<211> LENGTH: 11
<212> TYPE: PRT
<213> ORGANISM: Artificial Sequence
<220> FEATURE:
<223> OTHER INFORMATION: Synthetic Construct

<400> SEQUENCE: 147

Asp Ile Ser Gly Gly Gly Gly Arg Thr Tyr Tyr
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Synthetic Construct

<400> SEQUENCE: 148

Ala Gly Leu Leu Tyr Gly Gly Gly Val Tyr Pro Met Asp Ile
1               5                   10

<210> SEQ ID NO 149
<211> LENGTH: 16
<212> TYPE: PRT
<213> ORGANISM: Artificial Sequence
<220> FEATURE:
<223> OTHER INFORMATION: Synthetic Construct

<400> SEQUENCE: 149

Lys Ser Ser Gln Ser Leu Leu Tyr Ser Asn Gly Lys Thr Tyr Leu Asn
1               5                   10                  15

<210> SEQ ID NO 150
<211> LENGTH: 7
<212> TYPE: PRT
<213> ORGANISM: Artificial Sequence
<220> FEATURE:
<223> OTHER INFORMATION: Synthetic Construct

<400> SEQUENCE: 150

Leu Val Ser Lys Leu Asp Ser
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic Construct

<400> SEQUENCE: 151
```

Val Gln Asp Thr His Phe Pro Leu Thr
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic Construct

<400> SEQUENCE: 152

Gln Val Ser Lys Leu Asp Ser
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Construct

<400> SEQUENCE: 153

Gly Gln Asp Thr His Phe Pro Leu Thr
1               5

<210> SEQ ID NO 154
<211> LENGTH: 16
<212> TYPE: PRT
<213> ORGANISM: Artificial Sequence
<220> FEATURE:
<223> OTHER INFORMATION: Synthetic Construct

<400> SEQUENCE: 154

Lys Ser Ser Gln Ser Leu Leu Tyr Ser Asn Asp Lys Thr Tyr Thr Asn
1               5                   10                  15

<210> SEQ ID NO 155
<211> LENGTH: 7
<212> TYPE: PRT
<213> ORGANISM: Artificial Sequence
<220> FEATURE:
<223> OTHER INFORMATION: Synthetic Construct

<400> SEQUENCE: 155

Glu Val Ser Lys Leu Asp Val
1               5

<210> SEQ ID NO 156
<211> LENGTH: 11
<212> TYPE: PRT
<213> ORGANISM: Artificial Sequence
<220> FEATURE:
<223> OTHER INFORMATION: Synthetic Construct

<400> SEQUENCE: 156

Arg Ala Ser Gln Ser Val Arg Ser Asn Leu Ala
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Synthetic Construct

<400> SEQUENCE: 157

Gly Ser Thr Ile Arg Ala Thr

```
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic Construct

<400> SEQUENCE: 158

Gln Gln Tyr Ser Asp Trp Pro Phe Thr
1               5

<210> SEQ ID NO 159
<211> LENGTH: 11
<212> TYPE: PRT
<213> ORGANISM: Artificial Sequence
<220> FEATURE:
<223> OTHER INFORMATION: Synthetic Construct

<400> SEQUENCE: 159

Arg Ala Ser Gln Ser Val Ser Ser Asn Phe Ala
1               5                   10

<210> SEQ ID NO 160
<211> LENGTH: 7
<212> TYPE: PRT
<213> ORGANISM: Artificial Sequence
<220> FEATURE:
<223> OTHER INFORMATION: Synthetic Construct

<400> SEQUENCE: 160

Gly Ala Thr Thr Arg Ala Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic Construct

<400> SEQUENCE: 161

Gln Gln Tyr Lys Asp Trp Pro Phe Thr
1               5

<210> SEQ ID NO 162
<211> LENGTH: 11
<212> TYPE: PRT
<213> ORGANISM: Artificial Sequence
<220> FEATURE:
<223> OTHER INFORMATION: Synthetic Construct

<400> SEQUENCE: 162

Arg Val Ser Gln Ser Ile Gly Ala Asn Leu Ala
1               5                   10

<210> SEQ ID NO 163
<211> LENGTH: 7
<212> TYPE: PRT
<213> ORGANISM: Artificial Sequence
<220> FEATURE:
<223> OTHER INFORMATION: Synthetic Construct

<400> SEQUENCE: 163

Gly Ala Ser Thr Arg Ala Thr
1               5
```

<210> SEQ ID NO 164
<211> LENGTH: 9
<212> TYPE: PRT
<213> ORGANISM: Artificial Sequence
<220> FEATURE:
<223> OTHER INFORMATION: Synthetic Construct

<400> SEQUENCE: 164

Gln Gln Tyr Ile Tyr Trp Pro Phe Thr
1               5

<210> SEQ ID NO 165
<211> LENGTH: 11
<212> TYPE: PRT
<213> ORGANISM: Artificial Sequence
<220> FEATURE:
<223> OTHER INFORMATION: Synthetic Construct

<400> SEQUENCE: 165

Arg Ala Ser Gln Ser Val Ser Asn Asn Leu Ala
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Synthetic Construct

<400> SEQUENCE: 166

Arg Ala Ser Gln Ser Val Gly Ser Asp Leu Ala
1               5                   10

<210> SEQ ID NO 167
<211> LENGTH: 9
<212> TYPE: PRT
<213> ORGANISM: Artificial Sequence
<220> FEATURE:
<223> OTHER INFORMATION: Synthetic Construct

<400> SEQUENCE: 167

Gln Gln Tyr Asn Asp Trp Pro Phe Thr
1               5

<210> SEQ ID NO 168
<211> LENGTH: 11
<212> TYPE: PRT
<213> ORGANISM: Artificial Sequence
<220> FEATURE:
<223> OTHER INFORMATION: Synthetic Construct

<400> SEQUENCE: 168

Arg Ala Ser Gln Asn Ile Gly Ser Asp Leu Ala
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Synthetic Construct

<400> SEQUENCE: 169

Arg Ala Ser Gln Ser Val Thr Ser Asn Phe Ala
1               5                   10

```
<210> SEQ ID NO 170
<211> LENGTH: 11
<212> TYPE: PRT
<213> ORGANISM: Artificial Sequence
<220> FEATURE:
<223> OTHER INFORMATION: Synthetic Construct

<400> SEQUENCE: 170

Arg Ala Ser Gln Gly Val Ser Ser Asn Phe Ala
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Synthetic Construct

<400> SEQUENCE: 171

Arg Ala Ser Gln Ser Val Asn Arg Asn Leu Ala
1               5                   10

<210> SEQ ID NO 172
<211> LENGTH: 7
<212> TYPE: PRT
<213> ORGANISM: Artificial Sequence
<220> FEATURE:
<223> OTHER INFORMATION: Synthetic Construct

<400> SEQUENCE: 172

Gly Thr Ser Thr Arg Ala Thr
1               5

<210> SEQ ID NO 173
<211> LENGTH: 11
<212> TYPE: PRT
<213> ORGANISM: Artificial Sequence
<220> FEATURE:
<223> OTHER INFORMATION: Synthetic Construct

<400> SEQUENCE: 173

Arg Ala Ser Gln Ser Val Ser Thr Asn Phe Ala
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Synthetic Construct

<400> SEQUENCE: 174

Arg Ala Ser Gln Ser Val Asn Ser Asn Leu Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Synthetic Construct

<400> SEQUENCE: 175

Gly Ser Ser Thr Arg Ala Thr
1               5
```

```
<210> SEQ ID NO 176
<211> LENGTH: 11
<212> TYPE: PRT
<213> ORGANISM: Artificial Sequence
<220> FEATURE:
<223> OTHER INFORMATION: Synthetic Construct

<400> SEQUENCE: 176

Arg Ala Ser Gln Ser Val Ile Asn Asn Leu Ala
1               5                   10

<210> SEQ ID NO 177
<211> LENGTH: 9
<212> TYPE: PRT
<213> ORGANISM: Artificial Sequence
<220> FEATURE:
<223> OTHER INFORMATION: Synthetic Construct

<400> SEQUENCE: 177

Gln Asp Tyr Asn Asn Trp Pro Phe Thr
1               5

<210> SEQ ID NO 178
<211> LENGTH: 11
<212> TYPE: PRT
<213> ORGANISM: Artificial Sequence
<220> FEATURE:
<223> OTHER INFORMATION: Synthetic Construct

<400> SEQUENCE: 178

Arg Ala Ser Gln Ser Val Gly Ser Asn Leu Ala
1               5                   10

<210> SEQ ID NO 179
<211> LENGTH: 8
<212> TYPE: PRT
<213> ORGANISM: Artificial Sequence
<220> FEATURE:
<223> OTHER INFORMATION: Synthetic Construct

<400> SEQUENCE: 179

Gly Ala Ser Thr Arg Ala Ser Gly
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic Construct

<400> SEQUENCE: 180

Gln Glu Tyr Asn Asn Trp Pro Phe Thr
1               5

<210> SEQ ID NO 181
<211> LENGTH: 11
<212> TYPE: PRT
<213> ORGANISM: Artificial Sequence
<220> FEATURE:
<223> OTHER INFORMATION: Synthetic Construct

<400> SEQUENCE: 181

Arg Ala Asn Gln Ile Val Ser Ser Asn Leu Ala
1               5                   10

<210> SEQ ID NO 182
```

```
<211> LENGTH: 16
<212> TYPE: PRT
<213> ORGANISM: Artificial Sequence
<220> FEATURE:
<223> OTHER INFORMATION: Synthetic Construct

<400> SEQUENCE: 182

Arg Ser Ser Gln Ser Leu Leu His Asn Lys Arg Asn Asn Tyr Leu Asp
1               5                   10                  15

<210> SEQ ID NO 183
<211> LENGTH: 7
<212> TYPE: PRT
<213> ORGANISM: Artificial Sequence
<220> FEATURE:
<223> OTHER INFORMATION: Synthetic Construct

<400> SEQUENCE: 183

Leu Ala Ser Asn Arg Ala Ser
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic Construct

<400> SEQUENCE: 184

Met Gln Ala Gln Gln Thr Pro Ile Thr
1               5

<210> SEQ ID NO 185
<211> LENGTH: 16
<212> TYPE: PRT
<213> ORGANISM: Artificial Sequence
<220> FEATURE:
<223> OTHER INFORMATION: Synthetic Construct

<400> SEQUENCE: 185

Arg Ser Ser Gln Ser Leu Leu Tyr Ser Asn Gly Lys Asn Tyr Leu Asp
1               5                   10                  15

<210> SEQ ID NO 186
<211> LENGTH: 7
<212> TYPE: PRT
<213> ORGANISM: Artificial Sequence
<220> FEATURE:
<223> OTHER INFORMATION: Synthetic Construct

<400> SEQUENCE: 186

Leu Gly Ser Asn Arg Ala Ser
1               5

<210> SEQ ID NO 187
<211> LENGTH: 16
<212> TYPE: PRT
<213> ORGANISM: Artificial Sequence
<220> FEATURE:
<223> OTHER INFORMATION: Synthetic Construct

<400> SEQUENCE: 187

Arg Ser Ser Gln Ser Leu Leu His Arg Asp Gly Phe Asn Tyr Leu Asp
1               5                   10                  15

<210> SEQ ID NO 188
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 188

Leu Ala Ser Ser Arg Ala Ser
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic Construct

<400> SEQUENCE: 189

Met Gln Ala Leu Gln Thr Pro Ile Thr
1               5

<210> SEQ ID NO 190
<211> LENGTH: 16
<212> TYPE: PRT
<213> ORGANISM: Artificial Sequence
<220> FEATURE:
<223> OTHER INFORMATION: Synthetic Construct

<400> SEQUENCE: 190

Arg Ser Thr Gln Ser Leu Leu Tyr Ser Asn Gly Lys Asn Tyr Leu Asp
1               5                   10                  15

<210> SEQ ID NO 191
<211> LENGTH: 7
<212> TYPE: PRT
<213> ORGANISM: Artificial Sequence
<220> FEATURE:
<223> OTHER INFORMATION: Synthetic Construct

<400> SEQUENCE: 191

Leu Gly Ser Ile Arg Ala Ser
1               5

<210> SEQ ID NO 192
<211> LENGTH: 16
<212> TYPE: PRT
<213> ORGANISM: Artificial Sequence
<220> FEATURE:
<223> OTHER INFORMATION: Synthetic Construct

<400> SEQUENCE: 192

Arg Ser Ser Gln Ser Leu Leu Tyr Ser Asp Arg Arg Asn Tyr Leu Asp
1               5                   10                  15

<210> SEQ ID NO 193
<211> LENGTH: 7
<212> TYPE: PRT
<213> ORGANISM: Artificial Sequence
<220> FEATURE:
<223> OTHER INFORMATION: Synthetic Construct

<400> SEQUENCE: 193

Leu Gly Ser Tyr Arg Ala Ser
1               5

<210> SEQ ID NO 194
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 194

Met Gln Ala Leu Gln Ile Pro Ile Thr
1               5

<210> SEQ ID NO 195
<211> LENGTH: 13
<212> TYPE: PRT
<213> ORGANISM: Artificial Sequence
<220> FEATURE:
<223> OTHER INFORMATION: Synthetic Construct

<400> SEQUENCE: 195

Ser Gly Ser Ser Ser Asn Ile Gly Ser Asn Tyr Val Tyr
1               5                   10

<210> SEQ ID NO 196
<211> LENGTH: 7
<212> TYPE: PRT
<213> ORGANISM: Artificial Sequence
<220> FEATURE:
<223> OTHER INFORMATION: Synthetic Construct

<400> SEQUENCE: 196

Arg Asn Asn Gln Arg Pro Ser
1               5

<210> SEQ ID NO 197
<211> LENGTH: 11
<212> TYPE: PRT
<213> ORGANISM: Artificial Sequence
<220> FEATURE:
<223> OTHER INFORMATION: Synthetic Construct

<400> SEQUENCE: 197

Ala Ala Trp Asp Asp Asn Leu Ser Gly Trp Val
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Synthetic Construct

<400> SEQUENCE: 198

Arg Ala Ser Gln Ser Ile Ser Ser Tyr Leu Asn
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Synthetic Construct

<400> SEQUENCE: 199

Ala Ala Ser Ser Leu Gln Ser
1               5

<210> SEQ ID NO 200
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 200

Gln Gln Ser Tyr Ser Thr Pro Leu Thr
1               5

<210> SEQ ID NO 201
<211> LENGTH: 943
<212> TYPE: PRT
<213> ORGANISM: Homo sapiens

<400> SEQUENCE: 201

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335
```

-continued

Asn Thr Leu Val Trp Lys Tyr Ala Asp Ala Gly His Val Cys His Leu
              340                 345                 350

Cys His Pro Asn Cys Thr Tyr Gly Cys Thr Gly Pro Gly Leu Glu Gly
          355                 360                 365

Cys Pro Thr Asn Gly Pro Lys Ile Pro Ser Ile Ala Thr Gly Met Val
      370                 375                 380

Gly Ala Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                  405                 410                 415

Gln Glu Arg Glu Leu Val Glu Pro Leu Thr Pro Ser Gly Glu Ala Pro
              420                 425                 430

Asn Gln Ala Leu Leu Arg Ile Leu Lys Glu Thr Glu Phe Lys Lys Ile
          435                 440                 445

Lys Val Leu Gly Ser Gly Ala Phe Gly Thr Val Tyr Lys Gly Leu Trp
      450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                  485                 490                 495

Tyr Val Met Ala Ser Val Asp Asn Pro His Val Cys Arg Leu Leu Gly
              500                 505                 510

Ile Cys Leu Thr Ser Thr Val Gln Leu Ile Thr Gln Leu Met Pro Phe
          515                 520                 525

Gly Cys Leu Leu Asp Tyr Val Arg Glu His Lys Asp Asn Ile Gly Ser
      530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                  565                 570                 575

Leu Val Lys Thr Pro Gln His Val Lys Ile Thr Asp Phe Gly Leu Ala
              580                 585                 590

Lys Leu Leu Gly Ala Glu Glu Lys Glu Tyr His Ala Glu Gly Gly Lys
          595                 600                 605

Val Pro Ile Lys Trp Met Ala Leu Glu Ser Ile Leu His Arg Ile Tyr
      610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                  645                 650                 655

Ser Ser Ile Leu Glu Lys Gly Glu Arg Leu Pro Gln Pro Ile Cys
              660                 665                 670

Thr Ile Asp Val Tyr Met Ile Met Val Lys Cys Trp Met Ile Asp Ala
          675                 680                 685

Asp Ser Arg Pro Lys Phe Arg Glu Leu Ile Ile Glu Phe Ser Lys Met
      690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                  725                 730                 735

Glu Glu Asp Met Asp Asp Val Val Asp Ala Asp Glu Tyr Leu Ile Pro
              740                 745                 750

Gln Gln Gly Phe Phe Ser Ser Pro Ser Thr Ser Arg Thr Pro Leu Leu

```
                755                 760                 765
Ser Ser Leu Ser Ala Thr Ser Asn Asn Ser Thr Val Ala Cys Ile Asp
    770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
            820                 825                 830

Arg Pro Ala Gly Ser Val Gln Asn Pro Val Tyr His Asn Gln Pro Leu
        835                 840                 845

Asn Pro Ala Pro Ser Arg Asp Pro His Tyr Gln Asp Pro His Ser Thr
    850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
                885                 890                 895

Gln Ile Ser Leu Asp Asn Pro Asp Tyr Gln Gln Asp Phe Phe Pro Lys
            900                 905                 910

Glu Ala Lys Pro Asn Gly Ile Phe Lys Gly Ser Thr Ala Glu Asn Ala
        915                 920                 925

Glu Tyr Leu Arg Val Ala Pro Gln Ser Ser Glu Phe Ile Gly Ala
    930                 935                 940

<210> SEQ ID NO 202
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 202

Gln Val Thr Leu Glu Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Pro Glu
        35                  40                  45

Trp Phe Ala His Ile Phe Ser Thr Asp Glu Lys Ser Leu Arg Leu Ser
    50                  55                  60

Leu Arg Ser Arg Leu Thr Leu Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Ser Asn Tyr Glu Gly Tyr Phe Asp Tyr Trp Gly
            100                 105                 110

Gln Gly Thr Leu Val Thr Val Ser Ser
        115                 120

<210> SEQ ID NO 203
<211> LENGTH: 121
<212> TYPE: PRT
<213> ORGANISM: Artificial Sequence
<220> FEATURE:
```

<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 203

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Asn Pro
            20                  25                  30
Arg Met Gly Val Ser Trp Ile Arg Gln Pro Pro Gly Lys Ala Leu Glu
        35                  40                  45
Trp Leu Gly His Ile Phe Ser Ser Asp Glu Lys Ser Tyr Arg Leu Ser
    50                  55                  60
Leu Arg Ser Arg Leu Ser Ile Ser Lys Asp Thr Ser Lys Ser Gln Val
65                  70                  75                  80
Val Leu Thr Met Thr Asn Met Asp Pro Val Asp Thr Ala Thr Tyr Tyr
                85                  90                  95
Cys Val Arg Xaa Xaa Ser Asn Tyr Gly Gly Tyr Phe Asp Tyr Trp Gly
            100                 105                 110
Gln Gly Thr Leu Val Thr Val Ser Ser
            115                 120
```

<210> SEQ ID NO 204
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 204

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Asn Pro
            20                  25                  30
Arg Met Gly Val Ser Trp Ile Arg Gln Pro Pro Gly Lys Ala Leu Glu
        35                  40                  45
Trp Leu Gly His Ile Phe Ser Ser Asp Glu Lys Ser Tyr Arg Leu Ser
    50                  55                  60
Leu Arg Ser Arg Leu Ser Ile Ser Lys Asp Thr Ser Lys Ser Gln Val
65                  70                  75                  80
Val Leu Thr Met Thr Asn Met Asp Pro Val Asp Thr Ala Thr Tyr Tyr
                85                  90                  95
Cys Val Arg Xaa Xaa Ser Asn Tyr Gly Gly Tyr Phe Asp Tyr Trp Gly
            100                 105                 110
Gln Gly Thr Leu Val Thr Val Ser Ser
            115                 120
```

<210> SEQ ID NO 205
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature

```
<222> LOCATION: (83)..(83)
<223> OTHER INFORMATION: Xaa can be any naturally occurring amino acid
<220> FEATURE:
<221> NAME/KEY: misc_feature
<222> LOCATION: (100)..(101)
<223> OTHER INFORMATION: Xaa can be any naturally occurring amino acid

<400> SEQUENCE: 205

Gln Val Thr Leu Lys Glu Ser Gly Pro Val Leu Val Lys Pro Thr Glu
1               5                   10                  15

Thr Leu Thr Leu Thr Cys Thr Val Phe Gly Phe Ser Leu Ser Asn Pro
            20                  25                  30

Arg Met Gly Val Ser Trp Ile Arg Gln Pro Pro Gly Lys Ala Pro Glu
        35                  40                  45

Trp Leu Gly His Ile Phe Ser Ser Asp Glu Lys Ser Tyr Arg Leu Ser
    50                  55                  60

Leu Arg Ser Arg Leu Ser Ile Ser Lys Asp Thr Ser Lys Ser Gln Val
65                  70                  75                  80

Val Phe Xaa Met Thr Asn Met Asp Pro Gly Asp Pro Ala Thr Tyr Tyr
                85                  90                  95

Cys Val Arg Xaa Xaa Ser Asn Tyr Glu Glu Tyr Phe Asp Tyr Trp Gly
            100                 105                 110

Gln Gly Thr Leu Val Thr Val Ser Ser
            115                 120

<210> SEQ ID NO 206
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (100)..(101)
<223> OTHER INFORMATION: Xaa can be any naturally occurring amino acid

<400> SEQUENCE: 206

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Pro
            20                  25                  30

Arg Met Gly Val Ser Trp Leu Arg Gln Pro Pro Gly Lys Ala Leu Glu
        35                  40                  45

Trp Phe Ala His Ile Phe Ser Thr Asp Glu Lys Ser Tyr Ser Pro Ser
    50                  55                  60

Leu Arg Gly Arg Leu Thr Val Ser Lys Asp Thr Ser Lys Ser Gln Val
65                  70                  75                  80

Val Leu Thr Leu Thr Asn Met Asp Pro Val Asp Thr Ala Thr Tyr Tyr
                85                  90                  95

Cys Ala Arg Xaa Xaa Ser Asn Tyr Glu Gly Tyr Phe Asp Tyr Trp Gly
            100                 105                 110

Gln Gly Thr Leu Val Thr Val Ser Ser
            115                 120

<210> SEQ ID NO 207
<211> LENGTH: 118
<212> TYPE: PRT
<213> ORGANISM: Artificial Sequence
<220> FEATURE:
<223> OTHER INFORMATION: Synthetic Construct
<220> FEATURE:
```

<221> NAME/KEY: misc_feature
<222> LOCATION: (56)..(57)
<223> OTHER INFORMATION: Xaa can be any naturally occurring amino acid

<400> SEQUENCE: 207

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Glu | Ala | Ser | Gly | Phe | Thr | Phe | Ser | Asp | Ala |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Arg | Ile | Lys | Ser | Lys | Thr | Xaa | Xaa | Gly | Thr | Thr | Asp | Tyr | Val | Val |
|---|---|---|---|---|---|---|---|---|---|---|---|---|---|---|---|
| 50 | | | | | 55 | | | | | 60 | | | | | |

| Pro | Leu | Asn | Gly | Arg | Phe | Ile | Ile | Ser | Arg | Asp | Asp | Ser | Arg | Asn | Thr |
|---|---|---|---|---|---|---|---|---|---|---|---|---|---|---|---|
| 65 | | | | | 70 | | | | | 75 | | | | | 80 |

| Leu | Tyr | Leu | Gln | Leu | Asn | Asn | Leu | Lys | Thr | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Thr | Thr | Val | Pro | Gly | Ser | Tyr | Gly | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser |
|---|---|---|---|---|---|
| | | | 115 | | |

<210> SEQ ID NO 208
<211> LENGTH: 120
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (56)..(57)
<223> OTHER INFORMATION: Xaa can be any naturally occurring amino acid

<400> SEQUENCE: 208

| Glu | Val | Asn | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Glu | Ala | Ser | Gly | Phe | Thr | Phe | Ser | Tyr | Ala |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Arg | Ile | Lys | Ser | Ile | Ala | Xaa | Xaa | Gly | Ala | Thr | Asp | Tyr | Ala | Ala |
|---|---|---|---|---|---|---|---|---|---|---|---|---|---|---|---|
| 50 | | | | | 55 | | | | | 60 | | | | | |

| Pro | Val | Arg | Asn | Arg | Phe | Thr | Ile | Ser | Arg | Asp | Asp | Ser | Arg | Asn | Thr |
|---|---|---|---|---|---|---|---|---|---|---|---|---|---|---|---|
| 65 | | | | | 70 | | | | | 75 | | | | | 80 |

| Leu | Tyr | Leu | Glu | Met | His | Ser | Leu | Lys | Thr | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Thr | Thr | Ile | Pro | Gly | Asn | Asp | Ala | Phe | Asp | Met | Trp | Gly | Gln |
|---|---|---|---|---|---|---|---|---|---|---|---|---|---|---|---|
| | | | 100 | | | | | 105 | | | | | 110 | | |

| Gly | Thr | Met | Val | Thr | Val | Ser | Ser |
|---|---|---|---|---|---|---|---|
| | | | 115 | | | | 120 |

<210> SEQ ID NO 209
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (56)..(57)
<223> OTHER INFORMATION: Xaa can be any naturally occurring amino acid

<400> SEQUENCE: 209

Glu Val Gln Leu Val Glu Ser Trp Gly Val Leu Val Lys Pro Gly Gly
1               5                   10                  15

Ser Leu Arg Leu Ser Cys Ala Ala Ser Gly Phe Ile Phe Asn Asn Ala
            20                  25                  30

Trp Met Ser Trp Val Arg Gln Ala Pro Gly Lys Gly Leu Glu Trp Ile
        35                  40                  45

Gly Arg Ile Lys Ser Lys Ser Xaa Xaa Gly Thr Thr Asp Tyr Ala Ala
    50                  55                  60

Pro Val Lys Asp Arg Phe Thr Ile Ser Arg Asp Asp Ser Lys Asp Thr
65                  70                  75                  80

Leu Tyr Leu Gln Met Asn Gly Leu Lys Thr Glu Asp Thr Ala Val Tyr
                85                  90                  95

Phe Cys Thr Thr Ala Pro Gly Gly Pro Phe Asp Tyr Trp Gly Gln Gly
            100                 105                 110

Thr Leu Val Thr Val Ser Ser
        115

<210> SEQ ID NO 210
<211> LENGTH: 120
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (56)..(57)
<223> OTHER INFORMATION: Xaa can be any naturally occurring amino acid

<400> SEQUENCE: 210

Glu Val Asn Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Tyr Ala
            20                  25                  30

Trp Met Ser Trp Val Arg Gln Ala Pro Gly Lys Gly Leu Glu Trp Val
        35                  40                  45

Gly Arg Ile Lys Ser Ile Thr Xaa Xaa Gly Val Ile Asp Tyr Ala Ala
    50                  55                  60

Pro Val Arg Asn Arg Cys Thr Ile Ser Arg Asp Asp Ser Arg Asn Thr
65                  70                  75                  80

Leu Tyr Leu Glu Met His Ser Leu Lys Thr Glu Asp Thr Ala Val Tyr
                85                  90                  95

Tyr Cys Thr Thr Ile Pro Gly Asn Asp Asp Phe Asp Met Trp Gly Gln
            100                 105                 110

Gly Arg Met Val Thr Val Ser Ser
        115                 120

<210> SEQ ID NO 211
<211> LENGTH: 112
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (33)..(34)
<223> OTHER INFORMATION: Xaa can be any naturally occurring amino acid

<400> SEQUENCE: 211

```
Asp Ile Val Leu Thr Gln Ser Pro Leu Ser Leu Ser Val Thr Pro Gly
1               5                   10                  15

Glu Pro Ala Ser Ile Ser Cys Arg Ser Ser Gln Ser Leu Leu Tyr Ser
            20                  25                  30

Xaa Xaa Lys Asn Tyr Leu Asp Trp Phe Leu His Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Ile Asp Phe Ile Leu Lys Ile
65                  70                  75                  80

Ser Arg Val Glu Ala Glu Asp Val Gly Val Tyr Tyr Cys Met Gln Ala
                85                  90                  95

Gln Gln Thr Pro Ile Thr Phe Gly Gln Gly Thr Arg Leu Glu Ile Lys
            100                 105                 110
```

<210> SEQ ID NO 212
<211> LENGTH: 112
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (33)..(34)
<223> OTHER INFORMATION: Xaa can be any naturally occurring amino acid

<400> SEQUENCE: 212

```
Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Xaa Xaa Phe Asn Tyr Leu Asp Trp Phe Leu Gln Lys Pro Gly Gln Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Asp Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110
```

<210> SEQ ID NO 213
<211> LENGTH: 112
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (33)..(34)
<223> OTHER INFORMATION: Xaa can be any naturally occurring amino acid

<400> SEQUENCE: 213

```
Asp Ile Val Leu Thr Gln Ser Pro Leu Ser Leu Ser Val Thr Pro Gly
1               5                   10                  15

Glu Pro Ala Ser Ile Ser Cys Arg Ser Ser Gln Ser Leu Leu Tyr Ser
            20                  25                  30

Xaa Xaa Lys Asn Tyr Leu Asp Trp Phe Leu His Lys Pro Gly Gln Ser
        35                  40                  45
```

Pro Gln Leu Leu Ile Tyr Leu Gly Ser Asn Arg Ala Ser Gly Val Pro
        50                  55                  60

Asp Arg Phe Ser Gly Ser Gly Ser Gly Ile Asp Phe Ile Leu Lys Ile
65                  70                  75                  80

Ser Arg Val Glu Ala Glu Asp Val Gly Val Tyr Tyr Cys Met Gln Ala
                85                  90                  95

Gln Gln Thr Pro Ile Thr Phe Gly Gln Gly Thr Arg Leu Glu Ile Lys
            100                 105                 110

<210> SEQ ID NO 214
<211> LENGTH: 120
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (56)..(57)
<223> OTHER INFORMATION: Xaa can be any naturally occurring amino acid

<400> SEQUENCE: 214

Glu Val Asn Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Tyr Ala
                20                  25                  30

Trp Met Ser Trp Val Arg Gln Ala Pro Gly Lys Gly Leu Glu Trp Val
            35                  40                  45

Gly Arg Ile Lys Ser Ile Asn Xaa Xaa Gly Ala Thr Asp Tyr Ala Ser
        50                  55                  60

Pro Val Arg Asn Arg Phe Thr Ile Ser Arg Asp Asp Ser Arg Asn Met
65                  70                  75                  80

Leu Tyr Leu Glu Met His Ser Leu Lys Thr Glu Asp Thr Ala Val Tyr
                85                  90                  95

Tyr Cys Thr Thr Ile Pro Gly Asn Asp Ala Phe Asp Met Trp Gly Gln
            100                 105                 110

Gly Thr Leu Val Thr Val Ser Ser
        115                 120

<210> SEQ ID NO 215
<211> LENGTH: 112
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (33)..(34)
<223> OTHER INFORMATION: Xaa can be any naturally occurring amino acid

<400> SEQUENCE: 215

Asp Ile Val Leu Thr Gln Ser Pro Leu Ser Leu Ser Val Thr Pro Gly
1               5                   10                  15

Glu Pro Ala Ser Ile Ser Cys Arg Ser Thr Gln Ser Leu Leu Tyr Ser
                20                  25                  30

Xaa Xaa Lys Asn Tyr Leu Asp Trp Phe Leu His Lys Pro Gly Gln Ser
            35                  40                  45

Pro Gln Leu Leu Ile Phe Leu Gly Ser Ile Arg Ala Ser Gly Val Pro
        50                  55                  60

Asp Arg Phe Ser Gly Ser Gly Ser Gly Ile Asp Phe Ile Leu Lys Ile
65                  70                  75                  80

```
Ser Arg Val Glu Ala Glu Asp Val Gly Val Tyr Tyr Cys Met Gln Ala
                 85                  90                  95

Gln Gln Thr Pro Ile Thr Phe Gly Gln Gly Thr Arg Leu Glu Ile Lys
            100                 105                 110

<210> SEQ ID NO 216
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (56)..(57)
<223> OTHER INFORMATION: Xaa can be any naturally occurring amino acid

<400> SEQUENCE: 216

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Thr Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Ile Xaa Xaa Gly Thr Thr Asp Tyr Ala Ala
    50                  55                  60

Pro Val Lys Gly Arg Phe Ile Ile Ser Arg Asp Asp Ser Lys Asn Thr
65                  70                  75                  80

Leu Ser Leu Gln Met Asn Ser Leu Lys Thr Glu Asp Thr Ala Met Tyr
                85                  90                  95

Tyr Cys Thr Thr Ala Pro Gly Gly Pro Phe Asp Tyr Trp Gly Gln Gly
            100                 105                 110

Ser Leu Val Thr Val Ser Ser
        115

<210> SEQ ID NO 217
<211> LENGTH: 126
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (114)..(115)
<223> OTHER INFORMATION: Xaa can be any naturally occurring amino acid

<400> SEQUENCE: 217

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Asn
            20                  25                  30

Ala Ile Ser Trp Val Arg Gln Ala Pro Gly Gln Gly Leu Glu Trp Met
        35                  40                  45

Gly Val Ile Ile Pro Ile Phe Gly Thr Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Thr Tyr His Glu Tyr Ala Gly Tyr Tyr Gly Gly Ala
            100                 105                 110
```

```
Met Xaa Xaa Trp Gly Gln Gly Thr Leu Val Thr Val Ser Ser
        115                 120                 125
```

<210> SEQ ID NO 218
<211> LENGTH: 122
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (62)..(63)
<223> OTHER INFORMATION: Xaa can be any naturally occurring amino acid

<400> SEQUENCE: 218

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Asp Ile Ser Gly Gly Gly Arg Thr Tyr Tyr Ala Xaa Xaa Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Tyr Gly Gly Gly Val Tyr Pro Met Asp Ile
            100                 105                 110

Trp Gly Gln Gly Thr Leu Val Thr Val Ser
        115                 120
```

<210> SEQ ID NO 219
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid

<400> SEQUENCE: 219

```
Xaa Xaa Ser Asn Tyr Glu Gly Tyr Phe Asp Phe
1               5                   10
```

<210> SEQ ID NO 220
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid

<400> SEQUENCE: 220

```
Xaa Xaa Ser Asn Tyr Glu Gly Tyr Phe Asp Tyr
1               5                   10
```

<210> SEQ ID NO 221
<211> LENGTH: 11
<212> TYPE: PRT

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid

<400> SEQUENCE: 221

Xaa Xaa Ser Asn Tyr Gly Gly Tyr Phe Asp Tyr
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid

<400> SEQUENCE: 222

Xaa Xaa Ser Asp Tyr Glu Gly Tyr Phe Asp Tyr
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid

<400> SEQUENCE: 223

Xaa Xaa Ser Asn Tyr Glu Glu Tyr Phe Asp Tyr
1               5                   10

<210> SEQ ID NO 224
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 224

Arg Ile Lys Ser Lys Thr Xaa Xaa Gly Thr Thr Asp Tyr Val Val Pro
1               5                   10                  15

Leu Asn Gly

<210> SEQ ID NO 225
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 225
```

```
Arg Ile Lys Ser Lys Thr Xaa Xaa Gly Thr Thr Asp Tyr
1               5                   10
```

<210> SEQ ID NO 226
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 226

```
Arg Ile Lys Ser Ile Ala Xaa Xaa Gly Ala Thr Asp Tyr Ala Ala Pro
1               5                   10                  15

Val Arg Asn
```

<210> SEQ ID NO 227
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 227

```
Arg Ile Lys Ser Ile Ala Xaa Xaa Gly Ala Thr Asp Tyr
1               5                   10
```

<210> SEQ ID NO 228
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 228

```
Arg Ile Lys Ser Lys Ser Xaa Xaa Gly Thr Thr Asp Tyr Ala Ala Pro
1               5                   10                  15

Val Lys Asp
```

<210> SEQ ID NO 229
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 229

```
Arg Ile Lys Ser Lys Ser Xaa Xaa Gly Thr Thr Asp Tyr
1               5                   10
```

<210> SEQ ID NO 230
<211> LENGTH: 19

<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 230

Arg Ile Lys Ser Ile Thr Xaa Xaa Gly Val Ile Asp Tyr Ala Ala Pro
1               5                   10                  15

Val Arg Asn

<210> SEQ ID NO 231
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 231

Arg Ile Lys Ser Ile Thr Xaa Xaa Gly Val Ile Asp Tyr
1               5                   10

<210> SEQ ID NO 232
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 232

Arg Ile Lys Ser Ile Asn Xaa Xaa Gly Ala Thr Asp Tyr Ala Ser Pro
1               5                   10                  15

Val Arg Asn

<210> SEQ ID NO 233
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 233

Arg Ile Lys Ser Ile Asn Xaa Xaa Gly Ala Thr Asp Tyr
1               5                   10

<210> SEQ ID NO 234
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)

<223> OTHER INFORMATION: Xaa can be any naturally occurring amino acid

<400> SEQUENCE: 234

Arg Ile Lys Ser Lys Ile Xaa Xaa Gly Thr Thr Asp Tyr Ala Ala Pro
1               5                   10                  15

Val Lys Gly

<210> SEQ ID NO 235
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 235

Arg Ile Lys Ser Lys Ile Xaa Xaa Gly Thr Thr Asp Tyr
1               5                   10

<210> SEQ ID NO 236
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(17)
<223> OTHER INFORMATION: Xaa can be any naturally occurring amino acid

<400> SEQUENCE: 236

His Thr Tyr His Glu Tyr Ala Gly Gly Tyr Tyr Gly Gly Ala Met Xaa
1               5                   10                  15

Xaa

<210> SEQ ID NO 237
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(14)
<223> OTHER INFORMATION: Xaa can be any naturally occurring amino acid

<400> SEQUENCE: 237

Asp Ile Ser Gly Gly Gly Gly Arg Thr Tyr Tyr Ala Xaa Xaa Val Lys
1               5                   10                  15

Gly

<210> SEQ ID NO 238
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(11)
<223> OTHER INFORMATION: Xaa can be any naturally occurring amino acid

<400> SEQUENCE: 238

Arg Ser Ser Gln Ser Leu Leu Tyr Ser Xaa Xaa Lys Asn Tyr Leu Asp

<210> SEQ ID NO 239
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(11)
<223> OTHER INFORMATION: Xaa can be any naturally occurring amino acid

<400> SEQUENCE: 239

Arg Ser Ser Gln Ser Leu Leu His Arg Xaa Xaa Phe Asn Tyr Leu Asp
1               5                   10                  15

<210> SEQ ID NO 240
<211> LENGTH: 121
<212> TYPE: PRT
<213> ORGANISM: Artificial Sequence
<220> FEATURE:
<223> OTHER INFORMATION: Synthetic Construct

<400> SEQUENCE: 240

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp His Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120

<210> SEQ ID NO 241
<211> LENGTH: 112
<212> TYPE: PRT
<213> ORGANISM: Artificial Sequence
<220> FEATURE:
<223> OTHER INFORMATION: Synthetic Construct

<400> SEQUENCE: 241

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Val
            20                  25                  30

Arg Ser Arg Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln

```
              85                  90                  95
Ser Tyr Asp Leu Phe Thr Phe Gly Ser Gly Thr Lys Leu Glu Ile Lys
            100                 105                 110

<210> SEQ ID NO 242
<211> LENGTH: 363
<212> TYPE: DNA
<213> ORGANISM: Artificial Sequence
<220> FEATURE:
<223> OTHER INFORMATION: Synthetic Construct

<400> SEQUENCE: 242
gaagtccaac ttgtcgaatc gggaggaggc cttgtgcaac ccggtggatc cctgaggctg      60
tcatgcgcgg cctcgggctt caccttttcc gattactaca tgacctgggt cagacaggcc     120
cctggaaagg ggttggaatg ggtggcattc atccggaata gagcccgcgg atacacttcc     180
gaccacaacc ccagcgtgaa ggggcggttc accattagcc gcgacaacgc caagaactcc     240
ctctacctcc aaatgaacag cctgcgggcg gaggataccg ctgtgtacta ctgcgcccgc     300
gaccggccgt cctactatgt gctggactac tggggccagg gtactacggt caccgtctcc     360
tca                                                                  363

<210> SEQ ID NO 243
<211> LENGTH: 336
<212> TYPE: DNA
<213> ORGANISM: Artificial Sequence
<220> FEATURE:
<223> OTHER INFORMATION: Synthetic Construct

<400> SEQUENCE: 243
gacattgtga tgactcaatc ccccgactcc ctggctgtgt ccctcggcga acgcgcaact      60
atcaactgta aaagcagcca gtccctgttc aacgtccggt cgaggaagaa ctacctggcc     120
tggtatcagc agaaacctgg gcagccgccg aagcttctga tctcatgggc ctcaactcgg     180
gaaagcggag tgccagatag attctccgga tctggctccg gaaccgactt caccctgacg     240
atttcgagct tgcaagcgga ggatgtggcc gtgtactact gcaagcagtc ctacgacctc     300
ttcacctttg gttcgggcac caagctggag atcaaa                              336

<210> SEQ ID NO 244
<211> LENGTH: 6
<212> TYPE: PRT
<213> ORGANISM: Artificial Sequence
<220> FEATURE:
<223> OTHER INFORMATION: Synthetic Construct

<400> SEQUENCE: 244

Ser Asp Tyr Tyr Met Thr
1               5

<210> SEQ ID NO 245
<211> LENGTH: 10
<212> TYPE: PRT
<213> ORGANISM: Artificial Sequence
<220> FEATURE:
<223> OTHER INFORMATION: Synthetic Construct

<400> SEQUENCE: 245

Gly Phe Thr Phe Ser Asp Tyr Tyr Met Thr
1               5                  10

<210> SEQ ID NO 246
```

```
<211> LENGTH: 13
<212> TYPE: PRT
<213> ORGANISM: Artificial Sequence
<220> FEATURE:
<223> OTHER INFORMATION: Synthetic Construct

<400> SEQUENCE: 246

Phe Ile Arg Asn Arg Ala Arg Gly Tyr Thr Ser Asp His
1               5                   10

<210> SEQ ID NO 247
<211> LENGTH: 19
<212> TYPE: PRT
<213> ORGANISM: Artificial Sequence
<220> FEATURE:
<223> OTHER INFORMATION: Synthetic Construct

<400> SEQUENCE: 247

Phe Ile Arg Asn Arg Ala Arg Gly Tyr Thr Ser Asp His Asn Pro Ser
1               5                   10                  15

Val Lys Gly

<210> SEQ ID NO 248
<211> LENGTH: 10
<212> TYPE: PRT
<213> ORGANISM: Artificial Sequence
<220> FEATURE:
<223> OTHER INFORMATION: Synthetic Construct

<400> SEQUENCE: 248

Asp Arg Pro Ser Tyr Tyr Val Leu Asp Tyr
1               5                   10

<210> SEQ ID NO 249
<211> LENGTH: 17
<212> TYPE: PRT
<213> ORGANISM: Artificial Sequence
<220> FEATURE:
<223> OTHER INFORMATION: Synthetic Construct

<400> SEQUENCE: 249

Lys Ser Ser Gln Ser Leu Phe Asn Val Arg Ser Arg Lys Asn Tyr Leu
1               5                   10                  15

Ala

<210> SEQ ID NO 250
<211> LENGTH: 7
<212> TYPE: PRT
<213> ORGANISM: Artificial Sequence
<220> FEATURE:
<223> OTHER INFORMATION: Synthetic Construct

<400> SEQUENCE: 250

Trp Ala Ser Thr Arg Glu Ser
1               5

<210> SEQ ID NO 251
<211> LENGTH: 8
<212> TYPE: PRT
<213> ORGANISM: Artificial Sequence
<220> FEATURE:
<223> OTHER INFORMATION: Synthetic Construct

<400> SEQUENCE: 251

Lys Gln Ser Tyr Asp Leu Phe Thr
1               5
```

<210> SEQ ID NO 252
<211> LENGTH: 326
<212> TYPE: PRT
<213> ORGANISM: Artificial Sequence
<220> FEATURE:
<223> OTHER INFORMATION: Synthetic Construct

<400> SEQUENCE: 252

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Arg Val Arg Cys Pro Arg Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Arg
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 253
<211> LENGTH: 978
<212> TYPE: DNA
<213> ORGANISM: Artificial Sequence

```
<220> FEATURE:
<223> OTHER INFORMATION: Synthetic Construct

<400> SEQUENCE: 253
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtagtgacc gtgccctcca gcaacttcgg cacccagacc     240
tacacctgca acgtagatca caagcccagc aacaccaagg tggacaagac agttgagcgc     300
aaatgtgtg tcaggtgccc aaggtgccca gcaccacctg tggcaggacc gtcagtcttc     360
ctcttccccc caaaacccaa ggacaccctc atgatctccc ggacccctga ggtcacgtgc     420
gtggtggtgg ccgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt cgtgcaccag gactggctga acggcaagga gtacaagtgc     600
aaggtctcca acaaaggcct cccatcctcc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caggctcacc gtggacaaga gcaggtggca gcaggggaac     900
gtcttctcat gctccgtgat gcatgaggct ctgcacaacc actacacaca gaagagcctc     960
tccctgtctc cgggtaaa                                                   978

<210> SEQ ID NO 254
<211> LENGTH: 326
<212> TYPE: PRT
<213> ORGANISM: Artificial Sequence
<220> FEATURE:
<223> OTHER INFORMATION: Synthetic Construct

<400> SEQUENCE: 254
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Glu Val Glu Cys Pro Glu Cys Pro Ala Pro
            100                 105                 110

Pro Val Ala Gly Pro Ser Val Phe Leu Phe Pro Lys Pro Lys Asp
        115                 120                 125

Thr Leu Met Ile Ser Arg Thr Pro Glu Val Thr Cys Val Val Val Ala
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
            195                 200                 205
Ser Ser Ile Glu Lys Thr Ile Ser Lys Thr Lys Gly Gln Pro Arg Glu
    210                 215                 220
Pro Gln Val Tyr Thr Leu Pro Pro Ser Arg Glu Met Thr Lys Asn
225                 230                 235                 240
Gln Val Ser Leu Thr Cys Glu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 255
<211> LENGTH: 978
<212> TYPE: DNA
<213> ORGANISM: Artificial Sequence
<220> FEATURE:
<223> OTHER INFORMATION: Synthetic Construct

<400> SEQUENCE: 255
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag cgctctgac cagcggcgtg cacaccttcc cggctgtcct acagtcctca     180
ggactctact ccctcagcag cgtagtgacc gtgccctcca gcaacttcgg cacccagacc     240
tacacctgca acgtagatca caagcccagc aacaccaagg tggacaagac agttgagcgc     300
aaatgtgagg tcgagtgccc agagtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt cgtgcaccag gactggctga acggcaagga gtacaagtgc     600
aaggtctcca acaaaggcct cccatcctcc atcgagaaaa ccatctccaa aaccaaaggg     660
cagccccgag aaccacaggt gtacaccctg cccccatccc gggaggagat gaccaagaac     720
caggtcagcc tgacctgcga ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
gtcttctcat gctccgtgat gcatgaggct ctgcacaacc actacacaca gaagagcctc     960
tccctgtctc cgggtaaa                                                   978

<210> SEQ ID NO 256

<211> LENGTH: 107
<212> TYPE: PRT
<213> ORGANISM: Homo sapiens

<400> SEQUENCE: 256

Gly Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 257
<211> LENGTH: 324
<212> TYPE: DNA
<213> ORGANISM: Homo sapiens

<400> SEQUENCE: 257
ggaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                            324

<210> SEQ ID NO 258
<211> LENGTH: 8
<212> TYPE: PRT
<213> ORGANISM: Artificial Sequence
<220> FEATURE:
<223> OTHER INFORMATION: Synthetic Construct

<400> SEQUENCE: 258

Leu Gln Gly Leu Leu Gln Gly Gly
1               5

<210> SEQ ID NO 259
<211> LENGTH: 4
<212> TYPE: PRT
<213> ORGANISM: Artificial Sequence
<220> FEATURE:
<223> OTHER INFORMATION: Synthetic Construct

<400> SEQUENCE: 259

Leu Leu Gln Gly
1

<210> SEQ ID NO 260
<211> LENGTH: 6
<212> TYPE: PRT
<213> ORGANISM: Artificial Sequence
<220> FEATURE:

<223> OTHER INFORMATION: Synthetic Construct

<400> SEQUENCE: 260

Leu Ser Leu Ser Gln Gly
1               5

<210> SEQ ID NO 261
<211> LENGTH: 8
<212> TYPE: PRT
<213> ORGANISM: Artificial Sequence
<220> FEATURE:
<223> OTHER INFORMATION: Synthetic Construct

<400> SEQUENCE: 261

Gly Gly Gly Leu Leu Gln Gly Gly
1               5

<210> SEQ ID NO 262
<211> LENGTH: 5
<212> TYPE: PRT
<213> ORGANISM: Artificial Sequence
<220> FEATURE:
<223> OTHER INFORMATION: Synthetic Construct

<400> SEQUENCE: 262

Gly Leu Leu Gln Gly
1               5

<210> SEQ ID NO 263
<211> LENGTH: 13
<212> TYPE: PRT
<213> ORGANISM: Artificial Sequence
<220> FEATURE:
<223> OTHER INFORMATION: Synthetic Construct

<400> SEQUENCE: 263

Leu Leu Gln Gly Ser Pro Leu Ala Gln Ser His Gly Gly
1               5                   10

<210> SEQ ID NO 264
<211> LENGTH: 7
<212> TYPE: PRT
<213> ORGANISM: Artificial Sequence
<220> FEATURE:
<223> OTHER INFORMATION: Synthetic Construct

<400> SEQUENCE: 264

Gly Leu Leu Gln Gly Gly Gly
1               5

<210> SEQ ID NO 265
<211> LENGTH: 6
<212> TYPE: PRT
<213> ORGANISM: Artificial Sequence
<220> FEATURE:
<223> OTHER INFORMATION: Synthetic Construct

<400> SEQUENCE: 265

Gly Leu Leu Gln Gly Gly
1               5

<210> SEQ ID NO 266
<211> LENGTH: 4
<212> TYPE: PRT
<213> ORGANISM: Artificial Sequence
<220> FEATURE:
<223> OTHER INFORMATION: Synthetic Construct

<400> SEQUENCE: 266

Gly Leu Leu Gln
1

<210> SEQ ID NO 267
<211> LENGTH: 8
<212> TYPE: PRT
<213> ORGANISM: Artificial Sequence
<220> FEATURE:
<223> OTHER INFORMATION: Synthetic Construct

<400> SEQUENCE: 267

Leu Leu Gln Leu Leu Gln Gly Ala
1               5

<210> SEQ ID NO 268
<211> LENGTH: 5
<212> TYPE: PRT
<213> ORGANISM: Artificial Sequence
<220> FEATURE:
<223> OTHER INFORMATION: Synthetic Construct

<400> SEQUENCE: 268

Leu Leu Gln Gly Ala
1               5

<210> SEQ ID NO 269
<211> LENGTH: 7
<212> TYPE: PRT
<213> ORGANISM: Artificial Sequence
<220> FEATURE:
<223> OTHER INFORMATION: Synthetic Construct

<400> SEQUENCE: 269

Leu Leu Gln Tyr Gln Gly Ala
1               5

<210> SEQ ID NO 270
<211> LENGTH: 6
<212> TYPE: PRT
<213> ORGANISM: Artificial Sequence
<220> FEATURE:
<223> OTHER INFORMATION: Synthetic Construct

<400> SEQUENCE: 270

Leu Leu Gln Gly Ser Gly
1               5

<210> SEQ ID NO 271
<211> LENGTH: 6
<212> TYPE: PRT
<213> ORGANISM: Artificial Sequence
<220> FEATURE:
<223> OTHER INFORMATION: Synthetic Construct

<400> SEQUENCE: 271

Leu Leu Gln Tyr Gln Gly
1               5

<210> SEQ ID NO 272
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 272

Leu Leu Gln Leu Leu Gln Gly
1               5

<210> SEQ ID NO 273
<211> LENGTH: 5
<212> TYPE: PRT
<213> ORGANISM: Artificial Sequence
<220> FEATURE:
<223> OTHER INFORMATION: Synthetic Construct

<400> SEQUENCE: 273

Ser Leu Leu Gln Gly
1               5

<210> SEQ ID NO 274
<211> LENGTH: 5
<212> TYPE: PRT
<213> ORGANISM: Artificial Sequence
<220> FEATURE:
<223> OTHER INFORMATION: Synthetic Construct

<400> SEQUENCE: 274

Leu Leu Gln Leu Gln
1               5

<210> SEQ ID NO 275
<211> LENGTH: 6
<212> TYPE: PRT
<213> ORGANISM: Artificial Sequence
<220> FEATURE:
<223> OTHER INFORMATION: Synthetic Construct

<400> SEQUENCE: 275

Leu Leu Gln Leu Leu Gln
1               5

<210> SEQ ID NO 276
<211> LENGTH: 5
<212> TYPE: PRT
<213> ORGANISM: Artificial Sequence
<220> FEATURE:
<223> OTHER INFORMATION: Synthetic Construct

<400> SEQUENCE: 276

Leu Leu Gln Gly Arg
1               5

<210> SEQ ID NO 277
<211> LENGTH: 6
<212> TYPE: PRT
<213> ORGANISM: Artificial Sequence
<220> FEATURE:
<223> OTHER INFORMATION: Synthetic Construct

<400> SEQUENCE: 277

Leu Leu Gln Gly Pro Pro
1               5

<210> SEQ ID NO 278
<211> LENGTH: 6
<212> TYPE: PRT
<213> ORGANISM: Artificial Sequence
<220> FEATURE:
<223> OTHER INFORMATION: Synthetic Construct

<400> SEQUENCE: 278
```

```
Leu Leu Gln Gly Pro Ala
1               5
```

<210> SEQ ID NO 279
<211> LENGTH: 8
<212> TYPE: PRT
<213> ORGANISM: Artificial Sequence
<220> FEATURE:
<223> OTHER INFORMATION: Synthetic Construct

<400> SEQUENCE: 279

```
Gly Gly Leu Leu Gln Gly Pro Pro
1               5
```

<210> SEQ ID NO 280
<211> LENGTH: 7
<212> TYPE: PRT
<213> ORGANISM: Artificial Sequence
<220> FEATURE:
<223> OTHER INFORMATION: Synthetic Construct

<400> SEQUENCE: 280

```
Gly Gly Leu Leu Gln Gly Ala
1               5
```

<210> SEQ ID NO 281
<211> LENGTH: 7
<212> TYPE: PRT
<213> ORGANISM: Artificial Sequence
<220> FEATURE:
<223> OTHER INFORMATION: Synthetic Construct

<400> SEQUENCE: 281

```
Leu Leu Gln Gly Pro Gly Lys
1               5
```

<210> SEQ ID NO 282
<211> LENGTH: 6
<212> TYPE: PRT
<213> ORGANISM: Artificial Sequence
<220> FEATURE:
<223> OTHER INFORMATION: Synthetic Construct

<400> SEQUENCE: 282

```
Leu Leu Gln Gly Pro Gly
1               5
```

<210> SEQ ID NO 283
<211> LENGTH: 5
<212> TYPE: PRT
<213> ORGANISM: Artificial Sequence
<220> FEATURE:
<223> OTHER INFORMATION: Synthetic Construct

<400> SEQUENCE: 283

```
Leu Leu Gln Gly Pro
1               5
```

<210> SEQ ID NO 284
<211> LENGTH: 4
<212> TYPE: PRT
<213> ORGANISM: Artificial Sequence
<220> FEATURE:
<223> OTHER INFORMATION: Synthetic Construct

<400> SEQUENCE: 284

```
Leu Leu Gln Pro
1

<210> SEQ ID NO 285
<211> LENGTH: 6
<212> TYPE: PRT
<213> ORGANISM: Artificial Sequence
<220> FEATURE:
<223> OTHER INFORMATION: Synthetic Construct

<400> SEQUENCE: 285

Leu Leu Gln Pro Gly Lys
1               5

<210> SEQ ID NO 286
<211> LENGTH: 7
<212> TYPE: PRT
<213> ORGANISM: Artificial Sequence
<220> FEATURE:
<223> OTHER INFORMATION: Synthetic Construct

<400> SEQUENCE: 286

Leu Leu Gln Ala Pro Gly Lys
1               5

<210> SEQ ID NO 287
<211> LENGTH: 7
<212> TYPE: PRT
<213> ORGANISM: Artificial Sequence
<220> FEATURE:
<223> OTHER INFORMATION: Synthetic Construct

<400> SEQUENCE: 287

Leu Leu Gln Gly Ala Pro Gly
1               5

<210> SEQ ID NO 288
<211> LENGTH: 6
<212> TYPE: PRT
<213> ORGANISM: Artificial Sequence
<220> FEATURE:
<223> OTHER INFORMATION: Synthetic Construct

<400> SEQUENCE: 288

Leu Leu Gln Gly Ala Pro
1               5

<210> SEQ ID NO 289
<211> LENGTH: 6
<212> TYPE: PRT
<213> ORGANISM: Artificial Sequence
<220> FEATURE:
<223> OTHER INFORMATION: Synthetic Construct

<400> SEQUENCE: 289

Leu Leu Gln Leu Gln Gly
1               5

<210> SEQ ID NO 290
<211> LENGTH: 326
<212> TYPE: PRT
<213> ORGANISM: Homo sapiens

<400> SEQUENCE: 290

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 291
<211> LENGTH: 330
<212> TYPE: PRT
<213> ORGANISM: Homo sapiens

<400> SEQUENCE: 291

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 292
<211> LENGTH: 327
<212> TYPE: PRT
<213> ORGANISM: Homo sapiens

<400> SEQUENCE: 292

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro

```
                100             105             110
Glu Phe Leu Gly Gly Pro Ser Val Phe Leu Phe Pro Pro Lys Pro Lys
            115             120             125

Asp Thr Leu Met Ile Ser Arg Thr Pro Glu Val Thr Cys Val Val Val
            130             135             140

Asp Val Ser Gln Glu Asp Pro Glu Val Gln Phe Asn Trp Tyr Val Asp
145             150             155             160

Gly Val Glu Val His Asn Ala Lys Thr Lys Pro Arg Glu Glu Gln Phe
                165             170             175

Asn Ser Thr Tyr Arg Val Val Ser Val Leu Thr Val Leu His Gln Asp
            180             185             190

Trp Leu Asn Gly Lys Glu Tyr Lys Cys Lys Val Ser Asn Lys Gly Leu
            195             200             205

Pro Ser Ser Ile Glu Lys Thr Ile Ser Lys Ala Lys Gly Gln Pro Arg
            210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
                245             250             255

Ile Ala Val Glu Trp Glu Ser Asn Gly Gln Pro Glu Asn Asn Tyr Lys
                260             265             270

Thr Thr Pro Pro Val Leu Asp Ser Asp Gly Ser Phe Phe Leu Tyr Ser
            275             280             285

Arg Leu Thr Val Asp Lys Ser Arg Trp Gln Glu Gly Asn Val Phe Ser
            290             295             300

Cys Ser Val Met His Glu Ala Leu His Asn His Tyr Thr Gln Lys Ser
305             310             315             320

Leu Ser Leu Ser Leu Gly Lys
                325
```

ANTIBODIES SPECIFIC FOR EPIDERMAL GROWTH FACTOR RECEPTOR VARIANT III AND THEIR USES

CROSS-REFERENCE TO RELATED APPLICATIONS

This application claims the benefit of U.S. Provisional Application No. 62/281,543 filed Jan. 21, 2016, and U.S. Provisional Application No. 62/431,766 filed Dec. 8, 2016, both of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC72271A_SEQ_Listing_20170110_ST25.txt" created on Jan. 6, 2017 and having a size of 160 KB. The sequence listing contained in this .txt file is part of the specification and is incorporated herein by reference in its entirety.

FIELD

The present invention relates to antibodies, e.g., full length antibodies or antigen binding fragments thereof, that specifically bind to Epidermal Growth Factor Receptor Variant III (EGFRvIII). The invention further relates to heteromultimeric antibodies (e.g., bispecific antibodies) and antibody conjugates (e.g., antibody-drug-conjugates). Compositions comprising the EGFRvIII antibodies, methods for producing and purifying such antibodies, and their use in diagnostics and therapeutics are also provided.

BACKGROUND

EGFR variant III (EGFRvIII), a tumor specific mutant of EGFR, is a product of genomic rearrangement which is often associated with wild-type EGFR gene amplification. EGFRvIII is formed by an in-frame deletion of exons 2-7, leading to deletion of 267 amino acids with a glycine substitution at the junction. The truncated receptor loses its ability to bind ligands but acquires constitutive kinase activity. Interestingly, EGFRvIII frequently co-expresses with full length wild-type EGFR in the same tumor cells. Moreover, EGFRvIII expressing cells exhibit increased proliferation, invasion, angiogenesis and resistance to apoptosis.

EGFRvIII is most often found in glioblastoma multiforme (GBM). It is estimated that 25-35% of GBM carries this truncated receptor. Moreover, its expression often reflects a more aggressive phenotype and poor prognosis. Besides GBM, expression of EGFRvIII has also been reported in other solid tumors such as non-small cell lung cancer, head and neck cancer, breast cancer, ovarian cancer and prostate cancer. In contrast, EGFRvIII is not expressed in healthy tissues. The lack of expression in normal tissues makes EGFRvIII an ideal target for developing tumor specific targeted therapy. To date, there has not been any FDA approved monoclonal antibody (e.g., monospecific or bispecific) against EGFRvIII identified with high affinity, high specificity, and high potency in treating cancers such as GBM. Accordingly, there remains a need for antibodies (e.g., monospecific or bispecific) treating cancers such as GBM with improved efficacy and safety profile, and suitable for use with human patients.

SUMMARY

The invention disclosed herein is directed to antibodies (e.g., monospecific or bispecific antibodies) and antibody conjugates that specifically bind to Epidermal Growth Factor Receptor Variant III (EGFRvIII). In one aspect, the invention provides an isolated antibody which specifically binds to EGFRvIII, wherein the antibody comprises (a) a heavy chain variable (VH) region comprising (i) a VH complementarity determining region one (CDR1) comprising the sequence shown in SEQ ID NO: 62, 63, 64, 74, 75, 76, 80, 81, 82, 88, 89, 90, 93, 94, 95, 99, 100, 101, 109, 110, 111, 115, 116, 117, 121, 122, 123, 132, 133, 134, 137, 138, 139, 143, 144, or 145; (ii) a VH CDR2 comprising the sequence shown in SEQ ID NO: 65, 66, 68, 69, 70, 71, 77, 78, 83, 84, 86, 87, 91, 92, 96, 97, 98, 102, 103, 105, 106, 112, 113, 118, 119, 124, 125, 127, 128, 130, 131, 135, 136, 140, 141, 146, 147, 224, 225, 226, 227, 228, 229, 230, 231, 232, 233, 234, 235, or 237; and iii) a VH CDR3 comprising the sequence shown in SEQ ID NO: 67, 72, 73, 79, 85, 104, 107, 108, 114, 120, 126, 129, 142, 148, 219, 220, 221, 222, 223, or 236; and/or a light chain variable (VL) region comprising (i) a VL CDR1 comprising the sequence shown in SEQ ID NO: 149, 154, 156, 159, 162, 165, 166, 168, 169, 170, 171, 173, 174, 176, 178, 181, 182, 185, 187, 190, 192, 195, 198, 238, or 239; (ii) a VL CDR2 comprising the sequence shown in SEQ ID NO: 150, 152, 155, 157, 160, 163, 172, 175, 179, 183, 186, 188, 191, 193, 196, or 199; and (iii) a VL CDR3 comprising the sequence shown in SEQ ID NO: 151, 153, 158, 161, 164, 167, 177, 180, 184, 189, 194, 197, or 200.

In another aspect, provided is an isolated antibody which specifically binds to EGFRvIII, wherein the antibody comprises: a VH region comprising a VH CDR1, VH CDR2, and VH CDR3 of the VH sequence shown in SEQ ID NO:1, 3, 5, 7, 9, 11, 13, 15, 17, 19, 21, 23, 25, 27, 30, 32, 34, 35, 37, 39, 41, 43, 44, 46, 48, 50, 52, 53, 54, 55, 56, 57, 58, 59, 60, 61, 202, 203, 204, 205, 206, 207, 208, 209, 210, 214, 216, 217, or 218; and/or a VL region comprising VL CDR1, VL CDR2, and VL CDR3 of the VL sequence shown in SEQ ID NO: 2, 4, 6, 8, 10, 12, 14, 16, 18, 20, 22, 24, 26, 28, 29, 31, 33, 36, 38, 40, 42, 45, 47, 49, 51, 211, 212, 213, or 215. In some embodiments, the VH region as described herein comprises a variant with one or several conservative amino acid substitutions in residues that are not within a CDR and/or the VL region as described herein comprises a variant with one or several amino acid substitutions in amino acids that are not within a CDR. For example, in some embodiments, the VH or VL region can comprise an amino acid sequence described above or a variant thereof with no more than 10, 9, 8, 7, 6, 5, 4, 3, 2, or 1 conservative substitutions in residues that are not within a CDR.

In some embodiments, provided is an isolated antibody which specifically binds to EGFRvIII, wherein the antibody comprises: a VH region comprising the sequence shown in SEQ ID NO: 5, 9, 11, 15, 30, 37, or 41; and/or a VL region comprising the sequence shown in SEQ ID NO: 6, 10, 12, 16, 31, 38, or 42. In some embodiments, the VH region comprises the sequence shown in SEQ ID NO: 5 and the VL region comprises the sequence shown in SEQ ID NO: 6. In some embodiments, the VH region comprises the sequence shown in SEQ ID NO: 9 and the VL region comprises the sequence shown in SEQ ID NO: 10. In some embodiments, the VH region comprises the sequence shown in SEQ ID NO: 11 and the VL region comprises the sequence shown in SEQ ID NO: 12. In some embodiments, the VH region comprises the sequence shown in SEQ ID NO: 15 and the VL region comprises the sequence shown in SEQ ID NO: 16. In some embodiments, the VH region comprises the sequence shown in SEQ ID NO: 30 and the VL region comprises the sequence shown in SEQ ID NO: 31. In some embodiments, the VH region comprises the sequence shown in SEQ ID NO: 37 and the VL region comprises the sequence shown in SEQ ID NO: 38. In some embodiments, the VH region comprises the sequence shown in SEQ ID NO: 41 and the VL region comprises the sequence shown in SEQ ID NO: 42.

In some embodiments, provided is an antibody which specifically binds to EGFRvIII and competes with an isolated antibody provided herein which specifically binds to EGFRvIII.

In another aspect, provided is a bispecific antibody wherein the bispecific antibody is a full-length human antibody, comprising a first antibody variable domain of the bispecific antibody specifically binding to a target antigen (e.g., EGFRvIII), and comprising a second antibody variable domain of the bispecific antibody capable of recruiting the activity of a human immune effector cell by specifically binding to an effector antigen (e.g., Cluster of differentiation 3 (CD3)) located on the human immune effector cell. In some embodiments, the first antibody variable domain comprises a heavy chain variable (VH) region comprising a VH CDR1, VH CDR2, and VH CDR3 of the VH sequence shown in SEQ ID NO: 1, 3, 5, 7, 9, 11, 13, 15, 17, 19, 21, 23, 25, 27, 30, 32, 34, 35, 37, 39, 41, 43, 44, 46, 48, 50, 52, 53, 54, 55, 56, 57, 58, 59, 60, 61, 202, 203, 204, 205, 206, 207, 208, 209, 210, 214, 216, 217, or 218; and/or a light chain variable (VL) region comprising VL CDR1, VL CDR2, and VL CDR3 of the VL sequence shown in SEQ ID NO: 2, 4, 6, 8, 10, 12, 14, 16, 18, 20, 22, 24, 26, 28, 29, 31, 33, 36, 38, 40, 42, 45, 47, 49, 51, 211, 212, 213, or 215. In some embodiments, the first antibody variable domain comprises (a) a heavy chain variable (VH) region comprising (i) a VH complementarity determining region one (CDR1) comprising the sequence shown in SEQ ID NO: 62, 63, 64, 74, 75, 76, 80, 81, 82, 88, 89, 90, 93, 94, 95, 99, 100, 101, 109, 110, 111, 115, 116, 117, 121, 122, 123, 132, 133, 134, 137, 138, 139, 143, 144, or 145; (ii) a VH CDR2 comprising the sequence shown in SEQ ID NO: 65, 66, 68, 69, 70, 71, 77, 78, 83, 84, 86, 87, 91, 92, 96, 97, 98, 102, 103, 105, 106, 112, 113, 118, 119, 124, 125, 127, 128, 130, 131, 135, 136, 140, 141, 146, 147, 224, 225, 226, 227, 228, 229, 230, 231, 232, 233, 234, 235, or 237; and iii) a VH CDR3 comprising the sequence shown in SEQ ID NO: 67, 72, 73, 79, 85, 104, 107, 108, 114, 120, 126, 129, 142, 148, 219, 220, 221, 222, 223, or 236; and/or (b) a light chain variable (VL) region comprising (i) a VL CDR1 comprising the sequence shown in SEQ ID NO: 149, 154, 156, 159, 162, 165, 166, 168, 169, 170, 171, 173, 174, 176, 178, 181, 182, 185, 187, 190, 192, 195, 198, 238, or 239; (ii) a VL CDR2 comprising the sequence shown in SEQ ID NO: 150, 152, 155, 157, 160, 163, 172, 175, 179, 183, 186, 188, 191, 193, 196, or 199; and (iii) a VL CDR3 comprising the sequence shown in SEQ ID NO: 151, 153, 158, 161, 164, 167, 177, 180, 184, 189, 194, 197, or 200.

In some embodiments, the second antibody variable domain comprises the VH and/or VL region specific against CD3. For example, the second antibody variable domain comprises a heavy chain variable (VH) region comprising a VH CDR1, VH CDR2, and VH CDR3 of the VH sequence shown in SEQ ID NO:240; and/or a light chain variable (VL) region comprising a VL CDR1, VL CDR2, and VL CDR3 of the VL sequence shown in SEQ ID NO: 241. In some embodiments, the second antibody variable domain comprises (a) a VH region comprising (i) a VH CDR1 comprising the sequence shown in SEQ ID NO: 244, 110, or 245; (ii) a VH CDR2 comprising the sequence shown in SEQ ID NO: 246 or 247; and iii) a VH CDR3 comprising the sequence shown in SEQ ID NO: 248; and/or a VL region comprising (i) a VL CDR1 comprising the sequence shown in SEQ ID NO: 249; (ii) a VL CDR2 comprising the sequence shown in SEQ ID NO: 250; and (iii) a VL CDR3 comprising the sequence shown in SEQ ID NO: 251.

In some embodiments, the antibodies described herein comprise a constant region. In some embodiments, the antibodies described herein are of the human IgG1, IgG2 or IgG2Δa, IgG3, or IgG4 subclass. In some embodiments, the antibodies described herein comprise a glycosylated constant region. In some embodiments, the antibodies described herein comprise a constant region having decreased binding affinity to one or more human Fc gamma receptor(s).

In some embodiments, both the first and the second antibody variable domains of the bispecific antibody comprise amino acid modifications at positions 223, 225, and 228 (e.g., (C223E or C223R), (E225R), and (P228E or P228R)) in the hinge region and at position 409 or 368 (e.g., K409R or L368E (EU numbering scheme)) in the CH3 region of human IgG2 (SEQ ID NO: 290).

In some embodiments, both the first and the second antibody variable domains of the bispecific antibody comprise amino acid modifications at position 265 (e.g., D265A) of the human IgG2.

In some embodiments, both the first and the second antibody variable domains of the bispecific antibody comprise amino acid modifications at one or more of positions 265 (e.g., D265A), 330 (e.g., A330S), and 331 (e.g., P331S) of the human IgG2. In some embodiments, both the first and the second antibody variable domains of the bispecific antibody comprise amino acid modifications at each of positions 265 (e.g., D265A), 330 (e.g., A330S), and 331 (e.g., P331S) of the human IgG2.

In another aspect, the invention provides an isolated antibody comprising an acyl donor glutamine-containing tag engineered at a specific site of the EGFRvIII antibody of the present invention.

In one variation, the invention provides an isolated antibody comprising an acyl donor glutamine-containing tag and an amino acid modification at position 222, 340, or 370 of the EGFRvIII antibody of the present invention. In some embodiments, the amino acid modification is a substitution from lysine to arginine.

In some embodiments, the EGFRvIII antibody of the present invention further comprises a linker.

In another aspect, the invention provides a conjugate of the EGFRvIII antibody as described herein, wherein the antibody is conjugated to an agent, wherein the agent is selected from the group consisting of a cytotoxic agent, an immunomodulating agent, an imaging agent, a therapeutic protein, a biopolymer, and an oligonucleotide. In some embodiments, the agent is a cytotoxic agent including, but not limited to, an anthracycline, an auristatin, a camptothecin, a combretastatin, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and stereoisomers, isosteres, analogs, or derivatives thereof. For example, the cytotoxic agent is MMAD (Monomethyl Auristatin D), 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1- oxoheptan-4-yl]-N-methyl-L-valinamide), 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide), 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide), or 0121(2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide).

In some embodiments, the present invention provides a conjugate comprising the formula: antibody-(acyl donor glutamine-containing tag)-(linker)-(cytotoxic agent).

In other embodiments, the invention provides pharmaceutical compositions comprising any of the antibodies or antibody conjugates described herein.

The invention also provides cell lines that recombinantly produce any of the antibodies described herein.

The invention also provides nucleic acids encoding any of the antibodies described herein. The invention also provides nucleic acids encoding a heavy chain variable region and/or a light chain variable region of any of the antibodies described herein.

The invention also provides a host cell comprising a nucleic acid or vector provided herein. Also provided is a method of producing an antibody (e.g. monospecific or bispecific) provided herein, comprising culturing a host cell provided herein under conditions that result in production of the antibody, and isolating the antibody from the host cell or culture.

The invention also provides kits comprising an effective amount of any of the antibodies or antibody conjugates described herein.

Also provided is an antibody, bispecific antibody, or conjugate of an antibody provided herein for use as a medicament.

The invention also provides methods of treating subjects in need thereof comprising providing the isolated antibodies, bispecific antibodies, or antibody conjugates described herein, and administering said antibodies to said subject.

Also provided are methods of treating a condition associated with malignant cells expressing EGFRvIII in a subject comprising administering to a subject in need thereof an effective amount of a pharmaceutical composition comprising the antibodies or antibody conjugates as described herein. In some embodiments, the condition is a cancer. In some embodiments, the cancer is an EGFRvIII related cancer (e.g., any cancer with EGFRvIII expression) selected from the group consisting of glioblastoma multiform, anaplastic astrocytoma, giant cell glioblastoma, gliosarcoma, anaplastic oligodendroglioma, anaplastic ependymoma, anaplastic oligoastrocytoma, choroid plexus carcinoma, anaplastic ganglioglioma, pineoblastoma, pineocytoma, meningioma, medulloepithelioma, ependymoblastoma, medulloblastoma, supraentorial primitive neuroectodermal tumor, atypical teratoid/rhabdoid tumor, head and neck cancer, non-small cell lung cancer, breast cancer, ovarian cancer, prostate cancer, medullobastoma, colorectal cancer, anal cancer, gastric cancer, thyroid cancer, mesothelioma, uterine cancer, and bladder cancer.

In another aspect, the invention provides a method of inhibiting tumor growth or progression in a subject who has malignant cells expressing EGFRvIII, comprising administering to the subject in need thereof an effective amount of a pharmaceutical composition comprising the isolated antibodies, bispecific antibodies, or antibody conjugates, as described herein.

In another aspect, the invention provides a method inhibiting metastasis of malignant cells expressing EGFRvIII in a subject, comprising administering to the subject in need thereof an effective amount of the pharmaceutical composition comprising the isolated antibodies, bispecific antibodies, or antibody conjugates, as described herein.

In another aspect, the invention provides a method inducing tumor regression in a subject who has malignant cells expressing EGFRvIII, comprising administering to the subject in need thereof an effective amount of the pharmaceutical composition of a pharmaceutical composition comprising the isolated antibodies, bispecific antibodies, or antibody conjugates, as described herein.

BRIEF DESCRIPTION OF THE FIGURES/DRAWINGS

FIGS. 1A, 1B, and 1C show examples of FACS binding histograms of three EGFRvIII antibodies: mAb 42G9 (FIG. 1A), 32A10 (FIG. 1B) and 32G8 (FIG. 1C), to the three F98 cell lines: F98 (EGFR negative), F98-EGFRwt, and F98-EGFRvIII. The X-axis is fluorescence intensity; the Y-axis is percentage of maximum/normalized to mode.

FIGS. 2A, 2B and 2C depict histograms showing the expression of wild-type EGFR and EGFRvIII in GBM cell lines as measured by flow cytometry: LN229-EGFRvIII (FIG. 2A), LN18-EGFRvIII (FIG. 2B) and DKMG (FIG. 2C). EGFRvIII was detected with mAb 42G9 and EGFRwt was detected with an EGFR wild-type specific mAb. The X-axis is fluorescence intensity; the Y-axis is percentage of maximum/normalized to mode.

DETAILED DESCRIPTION

Figure 1A:
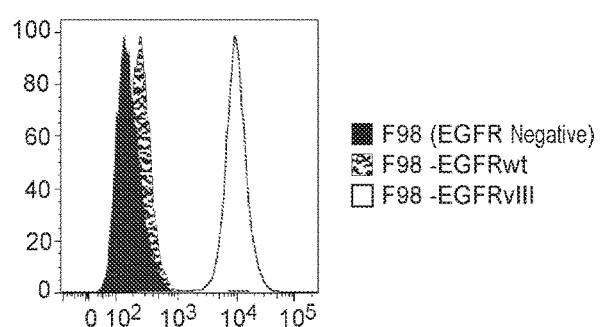

The invention disclosed herein provides antibodies (e.g., monospecific or bispecific) and antibody conjugates that specifically bind to EGFRvIII (e.g., human EGFRvIII). The invention also provides polynucleotides encoding these antibodies, compositions comprising these antibodies and antibody conjugates, and methods of making and using these antibodies and antibody conjugates. The invention also provides methods for treating a condition associated with EGFRvIII-mediated pathologies in a subject, such as cancer.

General Techniques

The practice of the present invention will employ, unless otherwise indicated, conventional techniques of molecular biology (including recombinant techniques), microbiology, cell biology, biochemistry, immunology, virology, monoclonal antibody generation and engineering, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen binding fragments thereof (such as Fab, Fab', F(ab')$_2$, Fv), single chain (ScFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., EGFRvIII). Antigen binding functions of an antibody can be performed by fragments of an intact antibody. Examples of binding fragments encompassed within the term "antigen binding fragment" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antibody conjugate, or a polypeptide that "preferentially binds" or "specifically binds" (used interchangeably herein) to a target (e.g., EGFRvIII protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an EGFRvIII epitope is an antibody that binds this epitope with greater affinity, avidity, more readily, and/or with greater duration than it binds to other EGFRvIII epitopes or non-EGFRvIII epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The terms "polypeptide", "oligopeptide", "peptide" and "protein" are used interchangeably herein to refer to chains of amino acids of any length. For example, the chain may be relatively short (e.g., 10-100 amino acids), or longer. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

A "monovalent antibody" comprises one antigen binding site per molecule (e.g., IgG or Fab). In some instances, a monovalent antibody can have more than one antigen binding sites, but the binding sites are from different antigens.

A "monospecific antibody" comprises two identical antigen binding sites per molecule (e.g. IgG) such that the two binding sites bind identical epitope on the antigen. Thus, they compete with each other on binding to one antigen molecule. Most antibodies found in nature are monospecific. In some instances, a monospecific antibody can also be a monovalent antibody (e.g. Fab)

A "bivalent antibody" comprises two antigen binding sites per molecule (e.g., IgG). In some instances, the two binding sites have the same antigen specificities. However, bivalent antibodies may be bispecific.

A "bispecific" or "dual-specific" is a hybrid antibody having two different antigen binding sites. The two antigen binding sites of a bispecific antibody bind to two different epitopes, which may reside on the same or different protein targets.

A "bifunctional" is antibody is an antibody having identical antigen binding sites (i.e., identical amino acid sequences) in the two arms but each binding site can recognize two different antigens.

A "heteromultimer", "heteromultimeric complex", or "heteromultimeric polypeptide" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where polypeptides in addition to the first and second polypeptide are present.

A "heterodimer," "heterodimeric protein," "heterodimeric complex," or "heteromultimeric polypeptide" is a molecule comprising a first polypeptide and a second polypeptide, wherein the second polypeptide differs in amino acid sequence from the first polypeptide by at least one amino acid residue.

The "hinge region," "hinge sequence", and variations thereof, as used herein, includes the meaning known in the art, which is illustrated in, for example, Janeway et al., ImmunoBiology: the immune system in health and disease, (Elsevier Science Ltd., NY) (4th ed., 1999); Bloom et al., Protein Science (1997), 6:407-415; Humphreys et al., J. Immunol. Methods (1997), 209:193-202.

The "immunoglobulin-like hinge region," "immunoglobulin-like hinge sequence," and variations thereof, as used herein, refer to the hinge region and hinge sequence of an immunoglobulin-like or an antibody-like molecule (e.g., immunoadhesins). In some embodiments, the immunoglobulin-like hinge region can be from or derived from any IgG1, IgG2, IgG3, or IgG4 subtype, or from IgA, IgE, IgD or IgM, including chimeric forms thereof, e.g., a chimeric IgG1/2 hinge region.

The term "immune effector cell" or "effector cell as used herein refers to a cell within the natural repertoire of cells in the human immune system which can be activated to affect the viability of a target cell. The viability of a target cell can include cell survival, proliferation, and/or ability to interact with other cells.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azidoribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art, a "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS* (*USA*), 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202: 163 (1996), may be performed.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of EGFRvIII expressing tumor, remission of an EGFRvIII associated disease (e.g., cancer), decreasing symptoms resulting from an EGFRvIII associated disease (e.g., cancer), increasing the quality of life of those suffering from an EGFRvIII associated disease (e.g., cancer), decreasing the dose of other medications required to treat an EGFRvIII associated disease (e.g., cancer), delaying the progression of an EGFRvIII associated disease (e.g., cancer), curing an EGFRvIII associated disease (e.g., cancer), and/or prolong survival of patients having an EGFRvIII associated disease (e.g., cancer).

"Ameliorating" means a lessening or improvement of one or more symptoms as compared to not administering an EGFRvIII antibody (monospecific or bispecific). "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various EGFRvIII associated diseases or conditions (such as for example multiple myeloma), decreasing the dose of other medications required to treat the disease, enhancing the effect of another medication, and/or delaying the progression of the EGFRvIII associated disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 21st Ed. Mack Publishing, 2005).

The term "acyl donor glutamine-containing tag" or "glutamine tag" as used herein refers to a polypeptide or a protein containing one or more Gln residue(s) that acts as a transglutaminase amine acceptor. See, e.g., WO2012059882 and WO2015015448.

The term "$k_{on}$" or "$k_a$", as used herein, refers to the rate constant for association of an antibody to an antigen. Specifically, the rate constants ($k_{on}/k_a$ and $k_{off}/k_d$) and equilibrium dissociation constants are measured using whole antibody (i.e. bivalent) and monomeric EGFRvIII proteins (e.g., Histidine-tagged EGFRvIII fusion protein).

The term "$k_{off}$" or "$k_d$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

EGFRvIII Antibodies and Methods of Making Thereof

The present invention provides an antibody that binds to EGFRvIII [e.g., human EGFRvIII (e.g., accession number: P00533 Feature Identifier VAR_066493, or GenBank Acession No. AJN69267; mrpsgtagaallallaalcp asraleekkgnyvvt-dhgscvracgadsyemeedgvrkckkcegperkvcngigigefkdslsi nat-nikhfknctsisgdlhilpvafrgdsfthtppldpqeldilktvkeitgflliqawpenrt dlhafenleiirgrtkqhgqfslavvslnitslglrslkeisdgdviisgnknlcy-antinwkk lfgtsgqktkiisnrgensckatgqvchalcspegcwgpeprd-cvscrnvsrgrecvdkcnlle geprefvenseciqchpeclpqamnitctgrgp-dnciqcahyidgphcvktcpagvmgenntiv wkyadaghvchlchpnctygctgpglegcptngpkipsiatgmvgalllll-vvalgiglfmrrr hivrkrtlrrllqerelvepltpsgeapnqallrilketefkkik-vlgsgafgtvykglwipeg ekvkipvaikelreatspkankeildeayvmas-vdnphvcrllgicltstvqlitqlmpfgcll dyvrehkdnigsqyllnwcvqiakgmnyledrrlvhrdlaarnvlvkt-pqhvkitdfglakllg aeekeyhaeggkvpikwmalesilhriythqsd-vwsygvtvwelmtfgskpydgipaseissil ekgerlpqppictidvymim-vkcwmidadsrpkfreliiefskmardpqrylviqgdermhlps ptdsnfyralmdeedmddvvdadeylipqqgffsspstsrtpllsslsatsnnst-vacidrngl qscpikedsflqryssdptgaltedsiddtflpvpeyinqsvp-krpagsvqnpvyhnqpinpap srdphyqdphstavgnpeylntvqptcvn-stfdspahwaqkgshqisldnpdyqqdffpkeakp ngifkgstaenaeylrvapqssefiga (SEQ ID NO: 201))] and characterized by any one or more of the following characteristics: (a) decrease or downregulate the protein expression of EGFRvIII; (b) treat, prevent, ameliorate one or more symptoms of a condition associated with malignant cells expressing EGFRvIII in a subject (e.g., cancer such as glioblastoma multiform); (c) inhibit tumor growth or progression in a subject (who has a malignant tumor expressing EGFRvIII); (d) inhibit metastasis of cancer (malignant) cells expressing EGFRvIII in a subject (who has one or more malignant cells expressing EGFRvIII); (e) induce regression (e.g., long-term regression) of a tumor expressing EGFRvIII; (f) exert cytotoxic activity in malignant cells expressing EGFRvIII; (g) block EGFRvIII interaction with other yet to be identified factors; and/or (h) induce bystander effect that kill or inhibit growth of non-EGFRvIII expressing malignant cells in the vicinity.

In one aspect, provided is an isolated antibody which specifically binds to EGFRvIII, wherein the antibody comprises (a) a heavy chain variable (VH) region comprising (i) a VH complementarity determining region one (CDR1) comprising the sequence shown in SEQ ID NO: 62, 63, 64, 74, 75, 76, 80, 81, 82, 88, 89, 90, 93, 94, 95, 99, 100, 101, 109, 110, 111, 115, 116, 117, 121, 122, 123, 132, 133, 134, 137, 138, 139, 143, 144, or 145; (ii) a VH CDR2 comprising the sequence shown in SEQ ID NO: 65, 66, 68, 69, 70, 71, 77, 78, 83, 84, 86, 87, 91, 92, 96, 97, 98, 102, 103, 105, 106, 112, 113, 118, 119, 124, 125, 127, 128, 130, 131, 135, 136, 140, 141, 146, 147, 224, 225, 226, 227, 228, 229, 230, 231, 232, 233, 234, 235, or 237; and iii) a VH CDR3 comprising the sequence shown in SEQ ID NO: 67, 72, 73, 79, 85, 104, 107, 108, 114, 120, 126, 129, 142, 148, 219, 220, 221, 222, 223, or 236; and/or (b) a light chain variable (VL) region comprising (i) a VL CDR1 comprising the sequence shown in SEQ ID NO: 149, 154, 156, 159, 162, 165, 166, 168, 169, 170, 171, 173, 174, 176, 178, 180, 181, 182, 185, 187, 190, 192, 195, 198, 238, or 239; (ii) a VL CDR2 comprising the sequence shown in SEQ ID NO: 150, 152, 155, 157, 160, 163, 172, 175, 179, 183, 186, 188, 191, 193, 196, or 199; and (iii) a VL CDR3 comprising the sequence shown in SEQ ID NO: 151, 153, 158, 161, 164, 167, 177, 180, 184, 189, 194, 197, or 200.

In another aspect, provided is an isolated antibody which specifically binds to EGFRvIII, wherein the antibody comprises: a VH region comprising a VH CDR1, VH CDR2, and VH CDR3 of the VH sequence shown in SEQ ID NO:1, 3, 5, 7, 9, 11, 13, 15, 17, 19, 21, 23, 25, 27, 30, 32, 34, 35, 37, 39, 41, 43, 44, 46, 48, 50, 52, 53, 54, 55, 56, 57, 58, 59, 60, 61, 202, 203, 204, 205, 206, 207, 208, 209, 210, 214, 216, 217, or 218; and/or a VL region comprising VL CDR1, VL CDR2, and VL CDR3 of the VL sequence shown in SEQ ID NO: 2, 4, 6, 8, 10, 12, 14, 16, 18, 20, 22, 24, 26, 28, 29, 31, 33, 36, 38, 40, 42, 45, 47, 49, 51, 211, 212, 213, or 215.

In some embodiments, provided is an antibody having any one of partial light chain sequence as listed in Table 1 and/or any one of partial heavy chain sequence as listed in Table 1. In Table 1, the underlined sequences are CDR sequences according to Kabat and in bold according to Chothia.

TABLE 1

| mAb | Light Chain | Heavy Chain |
|---|---|---|
| m62G7 | DVVMTQTPLTLSVTIGQPASISCK SSQSLLYSNGKTYLNWLLQRPG QSPKRLIYLVSKLDSGVPDRFTG SGSGTDFTLKISRVEAEDLGFYY CVQDTHFPLTFGAGTKLELK (SEQ ID NO: 2) | EVQLQQSGPELVKPGASVKISCKT SGYTTFTDYTLHVVVKQSHVKSLEWI GGIDPINGGTTYNQKFKGKATLTV DKSSSTAYMELRSLTSEDSAVYYC ARGEAMDSWGQGTSVTVSS (SEQ ID NO: 1) |
| h62G7 | DVVMTQSPLSLPVTLGQPASISC KSSQSLLYSNGKTYLNWFQQRP GQSPPRRLIYLVSKLDSGVPDRFS GSGSGTDFTLKISRVEAEDVGVY YCVQDTHFPLTFGGGTKVEIK (SEQ ID NO: 4) | QVQLVQSGAEVKKPGASVKVSCK ASGYTFTDYTLHWVRQAPGQGLE WMGGINPINGGTTYNQKFKGRVT MTRDTSTSTVYMELSSLRSEDTAV YYCARGEAMDSWGQGTLVTVSS (SEQ ID NO: 3) |
| h62G7-EQ/L6 | DVVMTQSPLSLPVTLGQPASISC KSSQSLLYSNGKTYLNWFQQRP GQSPPRRLIYQVSKLDSGVPDRFS GSGSGTDFTLKISRVEAEDVGVY YCGQDTHFPLTFGGGTKVEIK (SEQ ID NO: 6) | QVQLVQSGAEVKKPGASVKVSCK ASGYTFTDYTLHWVRQAPGQGLE WMGGIWPITGGTTYNQKFKGRVT MTRDTSTSTVYMELSSLRSEDTAV YYCARGEAQGSWGQGTLVTVSS (SEQ ID NO: 5) |

TABLE 1-continued

| mAb | Light Chain | Heavy Chain |
| --- | --- | --- |
| h62G7 H14/L1-DV | DVVMTQSPLSLPVTLGQPASISCKSSQSLLYSNDKTYTNWFQQRPGQSPRRLIYEVSKLDVGVPDRFSGSGSGTDFTLKISRVEAEDVGVYYCGQDTHFPLTFGGGTKVEIK (SEQ ID NO: 8) | QVQLVQSGAEVKKPGASVKVSCKASGYTFTDYTLHWVRQAPGQGLEWMGGIWPITGGTTYNQKFKGRVTMTRDTSTSTVYMELSSLRSEDTAVYYCARGEAEGSWGQGTLVTVSS (SEQ ID NO: 7) |
| 42G9 | EVVLTQSPATLSVSPGERATLSCRASQSVRSNLAWYQQKSGQAPRLLIYGSTIRATGVPARFSGSGSGTEFTLTISSLQSEDFAVYYCQQYSDWPFTFGPGTKVDIK (SEQ ID NO: 10) | QVTLKESGPVLLKPTETLTLTCTVSGFSLSNPRMGVSWIRQPPGKALEWFAHIFSTDEKSLKLSLRSRLTLSKDTSKSQVVLTMTNMAPVDSATYYCARDSSNYEGYFDFWGQGTLVTVSS (SEQ ID NO: 9) |
| 32A10 | EVVMTQSPATLSVSPGERVTLSCRASQSVSSNFAWYQQRPGQAPRLLLYGATTRATGLPGRFSGSGSGTENILTISSLQSEDFAIYFCQQYKDWPFTFGPGSKVDIK (SEQ ID NO: 12) | QVTLKESGPVLVKPTETLTLTCTVSGFSLSNARMGVSWIRQPPGKALEWLAHIFSTDEKSIRRSLRSRLTLSKDTSKSQVVLTMTNMDPVDTATYFCARDSSNYEGYFDYWGQGTLVTVSS (SEQ ID NO: 11) |
| 20B9 | EIVMTQSPATLSVSPGERATLSCRVSQSIGANLAWYQQKFGQAPRLLIYGASTRATGIPVRFSGGGSGTEFTLTISSLQSEDFAIYSCQQYIYWPFTFGPGTTVDIK (SEQ ID NO: 14) | QVTLKESGPVLVKPTETLTLTCTVSGFSLSNARMGVSWIRQPPGKALEWLGHIFSTDEKSYSTSLRGRITISKDTSRGLVVLTLTNMDPVDTATYYCARDSSNYEGYFDFWGPGFLVTVSS (SEQ ID NO: 13) |
| 14C11 | EIVMTQSPATLSVSPGERATLSCRASQSVSNNLAWYQQKPGQAPRLLIYGASTRATGVPARFSGSDSGTEFSLTISSLQSEDFAVYFCQQYKDWPFTFGPGTKVEIK (SEQ ID NO: 16) | QVTLKESGPVLVKPTETLTLTCTVSGFSLNNARMGVSWIRQPPGKALEWFAHIFSTDEKSFRTSLRSRLTLSKDTSKSQVVLTMTNMDPVDTATYYCARDSSNYEGYFDYWGQGILVTVSS (SEQ ID NO: 15) |
| 21E11 | DMVVTQSPATLSVSPGERATLSCRASQSVGSDLAWYQQPPGQSPRLLIYGASTRATGVPARFSGSGSGTDFTLTITSLESEDFAVYYCQQYNDWPFTFGPGTKVDIK (SEQ ID NO: 18) | QVTLKESGPVLVKPTETLTLTCTVSGFSLSNVRMGVSWIRQPPGKALEWFAHIFSSDEKSIRRSLRSRLTLSKDTSKSQVVLTMTNMDPVDTATYYCARDSSNYEGYFDFWGQGTLVTVSSN (SEQ ID NO: 17) |
| 49B11 | EMEVTQSPATLSVSPGERATLSCRASQNIGSDLAWYQQQSGQAPRLLISGASTRATGVPTRFSGSGSGTDFTLTITSLQSEDFAVYYCQQYNDWPFTFGPGTKVDIK (SEQ ID NO: 20) | QVTLKESGPVLVKPTETLTLTCTVSGFSLSNVRMGVSWIRQPPGKALEWFAHIFSSDEKSIRRSLRSRLTLSKDTSKSQVVLTMTNMDPVDTATYYCARDSSNYEGYFDYWGQGTLVTVSS (SEQ ID NO: 19) |
| 46E10 | EVVMTQSPPNLSVSPGERATLSCRASQSVTSNFAWYQQRPGQSPRLLLYGASTRATGVPGRFSGSGSGTENILTISSLQSEDFAVYFCQQYKDWPFTFGPGSKVDIK (SEQ ID NO: 22) | QVTLKESGPVLVKPTETLTLTCTVSGFSLSNARMGVSWIRQPPGKALEWLAHIFSTDEKSIRRSLRSRLTLSKDTSKSQVVLIMTNMDPVDTATYYCARDSSNYEGYFDYWGQGTLVTVSS (SEQ ID NO: 21) |
| 12H6 | EVVMTQSPATLSVSPGERATLSCRASQGVSSNFAWYQQRPGQSPRLLLYGASTRATGVPGRFSGSGSGTENILTISSLQSEDFAIYFCQQYKDWPFTFGPGSKVDIK (SEQ ID NO: 24) | QVTLKESGPVLVKPTETLTLTCTVSGFSLSNARMGVSWIRQPPGKALEWLAHIFSTDEKSIRRSLRSRLTLSKDTSKSQVVLTMTNMDPVDTATYYCARDSSNYEGYFDYWGQGTLVTVSS (SEQ ID NO: 23) |
| 19A9 | EVVMTQSPATLSVSPGERATLSCRASQSVNRNLAWYQQKPGQAPRLLIFGTSTRATGIPARFSGSGSGTEFTLTIDSLQSEHSGLYYCQQYNDWPFTFGPGTKVDIK (SEQ ID NO: 26) | QVTLEESGPVLVKPTETLTLTCTVSGFSLSNARMGVSWIRQPPGKAPEWFAHIFSTDEKSLRLSLRSRLTLSKDTSKSQVVLTMTNMDPVDTATYYCARDSSNYEGYFDYWGQGTLVTVSS (SEQ ID NO: 25) |
| 11B11 | EVLMTQSPATLSVSPGERATLSCRASQSVSTNFAWYQQRPGQAPRLLLFGASTRATGIPGRFSGSGSGTENILTISSLQSEDFAIYFCQQYKDWPFTFGPGSKVEIK (SEQ ID NO: 28) | QVTLKESGPVLVKPTETLTLTCTVSGFSLSNAKMGVSWIRQPPGKALEWLAHIFSTDEKSIRRSLRSRLTMSKDTSKSQVVLTMTNMDPVDTATYYCVRDSSNYEGYFDYWGQGTLVTVSS (SEQ ID NO: 27) |

TABLE 1-continued

| mAb | Light Chain | Heavy Chain |
|---|---|---|
| 21E7 | DVVLTQSPATLSVSPGERATLSC RASQSVNSNLAWYQQNPGQAP RLLIFGSSTRATGIPASFSGSGSG TEFTLTINSLQSEHSAVYYCQQY NDWPFTFGPGTKVDIK (SEQ ID NO: 29) | QVTLEESGPVLVKPTETLTLTCTV SGFSLSNARMGVSWIRQPPGKAP EWFAHIFSTDEKSLRLSLRSRLTL SKDTSKSQVVLTMTNMDPVDTAT YYCARDSSNYEGYFDYWGQGTLV TVSS (SEQ ID NO: 25) |
| 12B2 | EVVMTQSPATLSVSPGERATLSC RASQSVINNLAWYQQKPGQAPR LLIYGTSTRATDIPARFSGSGSGT EFTLTISSLQSEDFAVYYCQDYN NWPFTFGPGTKVDIK (SEQ ID NO: 31) | QVTLKESGPVLVKPTETLTLTCTV SGFSLSNPRMGVSWIRQPPGKAL EWLGHIFSSDEKSYRLSLRSRLSIS KDTSKSQVVLTMTNMDPVDTATY YCVRDSSNYGGYFDYWGQGTLV TVSS (SEQ ID NO: 30) |
| 11F10 | EIVMTQSPATLSVSPGERTTLSC RASQSVGSNLAWYQQKPGQAP RLLIYGASTRASGVPARFSGSGS GTEFTLTISSLQSEDFAVYSCQEY NNWPFTFGQGTKVEIK (SEQ ID NO: 33) | QVTLKESGPVLVKPIETLTLTCTVC GFSLSNPRMGVSWIRQPPGKALE WLGHIFSSDEKSYRLFLRSRLSISK DTSKSQVVLTMTNMDPVDTATYY CARDSSDYEGYFDYWGQGTLVTV SS (SEQ ID NO: 32) |
| 17G11 | EVVMTQSPATLSVSPGERATLSC RASQSVINNLAWYQQKPGQAPR LLIYGTSTRATDIPARFSGSGSGT EFTLTISSLQSEDFAVYYCQDYN NWPFTFGPGTKVDIK (SEQ ID NO: 31) | QVTLKESGPVLVKPTETLTLTCTVF GFSLSNPRMGVSWIRQPPGKAPE WLGHIFSSDEKSYRLSLRSRLSISK DTSKSQVVLTMTNMDPGDPATYY CVRDSSNYEEYFDYWGQGTLVTV SS (SEQ ID NO: 34) |
| 29D5 | KIVMTQSPATLSVSPGERATLSC RANQIVSSNLAWYQQKPGQAPR LLVFGTSTRATGIPIRFSGSGSGT EFTLTVSSLQSEDFAVYVCQQYN DWPFTFGPGTKVDIK (SEQ ID NO: 36) | QVTLKESGPVLVKPTETLTLTCTV SGFSLSNPRMGVSWLRQPPGKAL EWFAHIFSTDEKSYSPSLRGRLTV SKDTSKSQVVLTLTNMDPVDTATY YCARDSSNYEGYFDYWGQGTLVT VSS (SEQ ID NO: 35) |
| 30D8 | DIVMTQSPLSLPVTPGEPASISCR SSQSLLHNKRNNYLDWFLQKPG QSPQLLIYLASNRASGVPDRFSG GGSGTDFTLKISRVEAEDVGVYY CMQAQQTPITFGQGTRLEIK (SEQ ID NO: 38) | EVQLVESGGGLVKPGGSLRLSCE ASGFTFSDAWMSWVRQAPGKGL EWVGRIKSKTDGGTTDYVVPLNG RFIISRDDSRNTLYLQLNNLKTEDT AVYYCTTVPGSYGYWGQGTLVTV SS (SEQ ID NO: 37) |
| 20E12 | DIVLTQSPLSLSVTPGEPASISCR SSQSLLYSNGKNYLDWFLHKPG QSPQLLIYLGSNRASGVPDRFSG SGSGIDFLKISRVEAEDVGVYYC MQAQQTPITFGQGTRLEIK (SEQ ID NO: 40) | EVNLVESGGGLVKPGGSLRLSCE ASGFTFSYAWMSWVRQAPGKGL EWVGRIKSIADGGATDYAAPVRN RFTISRDDSRNTLYLEMHSLKTED TAVYYCTTIPGNDAFDMWGQGTM VTVSS (SEQ ID NO: 39) |
| 26B9 | DIVLTQSPLSLPVTPGEPASISCR SSQSLLHRDGFNYLDWFLQKPG QSPQLLIYLASSRASGVPDRFSG SDSGTDFTLKISRVEAEDVGVYY CMQALQTPITFGQGTRLEIK (SEQ ID NO: 42) | EVQLVESWGVLVKPGGSLRLSCA ASGFIFNNAWMSWVRQAPGKGLE WIGRIKSKSDGGTTDYAAPVKDRF TISRDDSKDTLYLQMNGLKTEDTA VYFCTTAPGGPFDYWGQGTLVTV SS (SEQ ID NO: 41) |
| 32G8 | DIVLTQSPLSLSVTPGEPASISCR SSQSLLYSNGKNYLDWFLHKPG QSPQLLIYLGSNRASGVPDRFSG SGSGIDFLKISRVEAEDVGVYYC MQAQQTPITFGQGTRLEIK (SEQ ID NO: 40) | EVNLVESGGGLVKPGGSLRLSCE ASGFTFSYAWMSWVRQAPGKGL EWVGRIKSITDGGVIDYAAPVRNR CTISRDDSRNTLYLEMHSLKTEDT AVYYCTTIPGNDDFDMWGQGRM VTVSS (SEQ ID NO: 43) |
| 34E7 | DIVLTQSPLSLSVTPGEPASISCR STQSLLYSNGKNYLDWFLHKPG QSPQLLIFLGSIRASGVPDRFSG SGSGIDFLKISRVEAEDVGVYYC MQAQQTPITFGQGTRLEIK (SEQ ID NO: 45) | EVNLVESGGGLVKPGGSLRLSCE ASGFTFSYAWMSWVRQAPGKGL EWVGRIKSINDGGATDYASPVRN RFTISRDDSRNMLYLEMHSLKTED TAVYYCTTIPGNDAFDMWGQGTL VTVSS (SEQ ID NO: 44) |
| 20G5 | DIVLTQSPLSLPVTPGEPASISCR SSQSLLYSDRRNYLDWFLQKPG QSPHLLIYLGSYRASGVPDRFSG SGSGTDFTLKISRVEAEDVGVYY CMQALQIPITFGQGTRLEIK (SEQ ID NO: 47) | EVQLVESGGDLVKPGGSLRLSCA ASGFTFTNAWMSWVRQAPGKGL EWVGRIKSIDGGTTDYAAPVKG RFIISRDDSKNTLSLQMNSLKTEDT AMYYCTTAPGGPFDYWGQGSLV TVSS (SEQ ID NO: 46) |

TABLE 1-continued

| mAb | Light Chain | Heavy Chain |
|---|---|---|
| C6 | ELQSVLTQPPSASGTPGQRVTIS CSGSSSNIGSNYVYWYQQLPGT APKILIYRNNQRPSGVPDRFSGS KSGTSASLAISGLRSEDEADYYC AAWDDNLSGWVFGTGTKLTVL (SEQ ID NO: 49) | QVQLVQSGAEVKKPGSSVKVSCK ASGDTFSSNAISWVRQAPGQGLE WMGVIIPIFGTADYAQKFQGRVTIT ADESTSTAYMELSSLRSEDTAVYY CARHTYHEYAGGYYGGAMDPWG QGTLVTVSS (SEQ ID NO: 48) |
| B5 | DIQMTQSPSSLSASVGDRVTITC RASQSISSYLNWYQQKPGKAPK LLIYAAASSLQSGVPSRFSGSGS TDFTLTISSLQPEDFATYYCQQSY STPLTFGQGTKVEIK (SEQ ID NO: 51) | EVQLLESGGGLVQPGGSLRLSCA ASGFTFSNYAMSWVRQAPGKGLE WVSDISGGGRTYYADSVKGRFTI SRDNSKNTLYLQMNSLRAEDTAV YYCARAGLLYGGGVYPMDIWGQ GTLVTVSS (SEQ ID NO: 50) |
| 42G9-1 | EVVLTQSPATLSVSPGERATLSC RASQSVRSNLAWYQQKSGQAP RLLIYGSTIRATGVPARFSGSGS GTEFTLTISSLQSEDFAVYYCQQ YSDWPFTFGPGTKVDIK (SEQ ID NO: 10) | QVTLKESGPVLLKPTETLTLTCTVS GFSLSNPRMGVSWIRQPPGKALE WFAHIFSTDEKSLKLSLRSRLTLSK DTSKSQVVLTMTNMAPVDSATYY CAR$X_1X_2$SNYEGYFDFWGQGTLVT VSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 52) |
| 32A10-1 | EVVMTQSPATLSVSPGERVTLSC RASQSVSSNFAWYQQRPGQAP RLLLYGATTRATGLPGRFSGSGS GTENILTISSLQSEDFAIYFCQQY KDWPFTFGPGSKVDIK (SEQ ID NO: 12) | QVTLKESGPVLVKPTETLTLTCTV SGFSLSNARMGVSWIRQPPGKAL EWLAHIFSTDEKSIRRSLRSRLTLS KDTSKSQVVLTMTNMDPVDTATY FCAR$X_1X_2$SNYEGYFDYWGQGTLV TVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 53) |
| 20B9-1 | EIVMTQSPATLSVSPGERATLSC RVSQSIGANLAWYQQKFGQAPR LLIYGASTRATGIPVRFSGGGS TEFTLTISSLQSEDFAIYSCQQYIY WPFTFGPGTTVDIK (SEQ ID NO: 14) | QVTLKESGPVLVKPTETLTLTCTV SGFSLSNARMGVSWIRQPPGKAL EWLHIFSTDEKSYSTSLRGRITIS KDTSRGLVVLTLTNMDPVDTATYY CAR$X_1X_2$SNYEGYFDFWGPGFLVT VSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 54) |
| 14C11-1 | EIVMTQSPATLSVSPGERATLSC RASQSVSNNLAWYQQKPGQAP RLLIYGASTRATGVPARFSGSDS GTEFSLTISSLQSEDFAVYFCQQ YKDWPFTFGPGTKVEIK (SEQ ID NO: 16) | QVTLKESGPVLVKPTETLTLTCTV SGFSLNNARMGVSWIRQPPGKAL EWFAHIFSTDEKSFRTSLRSRLTL SKDTSKSQVVLTMTNMDPVDTAT YYCAR$X_1X_2$SNYEGYFDYWGQGIL VTVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 55) |
| 21E11-1 | DMVVTQSPATLSVSPGERATLSC RASQSVGSDLAWYQQPPGQSP RLLIYGASTRATGVPARFSGSGS GTDFTLTITSLESEDFAVYYCQQY NDWPFTFGPGTKVDIK (SEQ ID NO: 18) | QVTLKESGPVLVKPTETLTLTCTV SGFSLSNVRMGVSWIRQPPGKAL EWFAHIFSSDEKSIRRSLRSRLTLS KDTSKSQVVLTMTNMDPVDTATY YCAR$X_1X_2$SNYEGYFDFWGQGTLV TVSSN, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 56) |
| 49B11-1 | EMEVTQSPATLSVSPGERATLSC RASQNIGSDLAWYQQQSGQAP RLLISGASTRATGVPTRFSGSGS GTDFTLTITSLQSEDFAVYYCQQ | QVTLKESGPVLVKPTETLTLTCTV SGFSLSNVRMGVSWIRQPPGKAL EWFAHIFSSDEKSI**RRSLRSRLTLS KDTSKSQVVLTMTNMDPVDTATY |

TABLE 1-continued

| mAb | Light Chain | Heavy Chain |
|---|---|---|
| | YNDWPFTFGPGTKVDIK (SEQ ID NO: 20) | YCARX₁X₂SNYEGYFDYWGQGTLV TVSS, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 57) |
| 46E10-1 | EVVMTQSPPNLSVSPGERATLSCRASQSVTSNFAWYQQRPGQSPRLLLYGASTRATGVPGRFSGSGSGTENLTISSLQSEDFAVYFCQQYKDWPFTFGPGSKVDIK (SEQ ID NO: 22) | QVTLKESGPVLVKPTETLTLTCTVSGFSLSNARMGVSWIRQPPGKALEWLAHIFSTDEKSIRRSLRSRLTLSKDTSKSQVVLIMTNMDPVDTATYYCARX₁X₂SNYEGYFDYWGQGTLVTVSS, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 58) |
| 12H6-1 | EVVMTQSPATLSVSPGERATLSCRASQGVSSNFAWYQQRPGQSPRLLLYGASTRATGVPGRFSGSGSGTENLTISSLQSEDFAIYFCQQYKDWPFTFGPGSKVDIK (SEQ ID NO: 24) | QVTLKESGPVLVKPTETLTLTCTVSGFSLSNARMGVSWIRQPPGKALEWLAHIFSTDEKSIRRSLRSRLTLSKDTSKSQVVLTMTNMDPVDTATYYCARX₁X₂SNYEGYFDYWGQGTLVTVSS, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 59) |
| 19A9-1 | EVVMTQSPATLSVSPGERATLSCRASQSVNRNLAWYQQKPGQAPRLLIFGTSTRATGIPARFSGSGSGTEFTLTIDSLQSEHSGLYYCQQYNDWPFTFGPGTKVDIK (SEQ ID NO: 26) | QVTLEESGPVLVKPTETLTLTCTVSGFSLSNARMGVSWIRQPPGKAPEWFAHIFSTDEKSLRLSLRSRLTLSKDTSKSQVVLTMTNMDPVDTATYYCARX₁X₂SNYEGYFDYWGQGTLVTVSS, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 60) |
| 11B11-1 | EVLMTQSPATLSVSPGERATLSCRASQSVSTNFAWYQQRPGQAPRLLLFGASTRATGIPGRFSGSGSGTENLTISSLQSEDFAIYFCQQYKDWPFTFGPGSKVEIK (SEQ ID NO: 28) | QVTLKESGPVLVKPTETLTLTCTVSGFSLSNAKMGVSWIRQPPGKALEWLAHIFSTDEKSIRRSLRSRLTMSKDTSKSQVVLTMTNMDPVDTATYYCVRX₁X₂SNYEGYFDYWGQGTLVTVSS, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 61) |
| 21E7-1 | DVVLTQSPATLSVSPGERATLSCRASQSVNSNLAWYQQNPGQAPRLLIFGSSTRATGIPASFSGSGSGTEFTLTINSLQSEHSAVYYCQQYNDWPFTFGPGTKVDIK (SEQ ID NO: 29) | QVTLEESGPVLVKPTETLTLTCTVSGFSLSNARMGVSWIRQPPGKAPEWFAHIFSTDEKSLRLSLRSRLTLSKDTSKSQVVLTMTNMDPVDTATYYCARX₁X₂SNYEGYFDYWGQGTLVTVSS, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 202) |
| 12B2-1 | EVVMTQSPATLSVSPGERATLSCRASQSVINNLAWYQQKPGAPRLLIYGTSTRATDIPARFSGSGSGTEFTLTISSLQSEDFAVYYCQDYNNWPFTFGPGTKVDIK (SEQ ID NO: 31) | QVTLKESGPVLVKPTETLTLTCTVSGFSLSNPRMGVSWIRQPPGKALEWLGHIFSDEKSYRLSLRSRLSISKDTSKSQVVLTMTNMDPVDTATYYCVRX₁X₂SNYGGYFDYWGQGTLVTVSS, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 203) |
| 11F10-1 | EIVMTQSPATLSVSPGERTTLSCRASQSVGSNLAWYQQKPGQAPRLLIYGASTRASGVPARFSGSGSGTEFTLTISSLQSEDFAVYSCQEYNNWPFTFGQGTKVEIK (SEQ ID | QVTLKESGPVLVKPIETLTLTCTVCGFSLSNPRMGVSWIRQPPGKALEWLGHIFSSDEKSYRLFLRSRLSISKDTSKSQVVLTMTNMDPVDTATYYCARX₁X₂SDYEGYFDYWGQGTLVT |

TABLE 1-continued

| mAb | Light Chain | Heavy Chain |
|---|---|---|
| | NO: 33) | VSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 204) |
| 17G11-1 | EVVMTQSPATLSVSPGERATLSCRASQSVINNLAWYQQKPGQAPRLLIYGTSTRATDIPARFSGSGSTEFTLTISSLQSEDFAVYYCQDYNNWPFTFGPGTKVDIK (SEQ ID NO: 31) | QVTLKESGPVLVKPTETLTLTCTVFGFSLSNPRMGVSWIRQPPGKAPEWLGHIFSSDEKSYRLSLRSRLSISKDTSKSQVVFXMTNMDPGDPATYYCVRX$_1$X$_2$SNYEEYFDYWGQGTLVTVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 205) |
| 29D5-1 | KIVMTQSPATLSVSPGERATLSCRANQIVSSNLAWYQQKPGQAPRLLVFGTSTRATGIPIRFSGSGSTEFTLTVSSLQSEDFAVYCQQYNDWPFTFGPGTKVDIK (SEQ ID NO: 36) | QVTLKESGPVLVKPTETLTLTCTVSGGFSLSNPRMGVSWLRQPPGKALEWFAHIFSTDEKSYSPSLRGRLTVSKDTSKSQVVLTLTNMDPVDTATYYCARX$_1$X$_2$SNYEGYFDYWGQGTLVTVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 206) |
| 30D8-1 | DIVMTQSPLSLPVTPGEPASISCRSSQSLLHNKRNNYLDWFLQKPGQSPQLLIYLASNRASGVPDRFSGGGSGTDFTLKISRVEAEDVGVYYCMQAQQTPITFGQGTRLEIK (SEQ ID NO: 38) | EVQLVESGGGLVKPGGSLRLSCEASGFTFSDAWMSWVRQAPGKGLEWVGRIKSKTX$_1$X$_2$GTTDYVVPLNGRFIISRDDSRNTLYLQLNNLKTEDTAVYYCTTVPGSYGYWGQGTLVTVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 207) |
| 20E12-1 | DIVLTQSPLSLSVTPGEPASISCRSSQSLLYSX$_1$X$_2$KNYLDWFLHKPGQSPQLLIYLGSNRASGVPDRFSGSGSGIDFILKISRVEAEDVGVYYCMQAQQTPITFGQGTRLEIK,, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 211) | EVNLVESGGGLVKPGGSLRLSCEASGFTFSYAWMSWVRQAPGKGLEWVGRIKSIAX$_1$X$_2$GATDYAAPVRNRFTISRDDSRNTLYLEMHSLKTEDTAVYYCTTIPGNDAFDMWGQGTVTVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 208) |
| 2689-1 | DIVLTQSPLSLPVTPGEPASISCRSSQSLLHRX$_1$X$_2$FNYLDWFLQKPGQSPQLLIYLASSRASGVPDRFSGSDSGTDFTLKISRVEAEDVGVYYCMQALQTPITFGQGTRLEIK, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 212) | EVQLVESWGVLVKPGGSLRLSCAASGFTFNNAWMSWVRQAPGKGLEWIGRIKSKSX$_1$X$_2$GTTDYAAPVKDRFTISRDDSKDTLYLQMNGLKTEDTAVYFCTTAPGGPFDYWGQGTLVTVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 209) |
| 32G8-1 | DIVLTQSPLSLSVTPGEPASISCRSSQSLLYSX$_1$X$_2$KNYLDWFLHKPGQSPQLLIYLGSNRASGVPDRFSGSGSGIDFILKISRVEAEDVGVYYCMQAQQTPITFGQGTRLEIK, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 213) | EVNLVESGGGLVKPGGSLRLSCEASGFTFSYAWMSWVRQAPGKGLEWVGRIKSITX$_1$X$_2$GVIDYAAPVRNRCTISRDDSRNTLYLEMHSLKTEDTAVYYCTTIPGNDDFDMWGQGRMVTVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 210) |
| 34E7-1 | DIVLTQSPLSLSVTPGEPASISCRSTQSLLYSX$_1$X$_2$KNYLDWFLHKPGQSPQLLIFLGSIRASGVPDRFSGSGSGIDFILKISRVEAEDVGVYYCMQAQQTPITFGQGTRLEIK,, wherein $X_1$ is R, H, K, D, E, S, T, | EVNLVESGGGLVKPGGSLRLSCEASGFTFSYAWMSWVRQAPGKGLEWVGRIKSINX$_1$X$_2$GATDYASPVRNRFTISRDDSRNMLYLEMHSLKTEDTAVYYCTTIPGNDAFDMWGQGTLVTVSS, wherein $X_1$ is R, H, K, D, E, |

TABLE 1-continued

| mAb | Light Chain | Heavy Chain |
|---|---|---|
| | N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 215) | S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 214) |
| 20G5-1 | DIVLTQSPLSLPVTPGEPASISCR SSQSLLYSDRRNYLDWFLQKPG QSPHLLIYLGSYRASGVPDRFSG SGSGTDFTLKISRVEAEDVGVYY CMQALQIPITFGQGTRLEIK (SEQ ID NO: 47) | EVQLVESGGDLVKPGGSLRLSCA ASGFTFTNAWMSWVRQAPGKGL EWVGRIKSKIX₁X₂GTTDYAAPVKG RFIISRDDSKNTLSLQMNSLKTEDT AMYYCTTAPGGPFDYWGQGSLV TVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 216) |
| C6-1 | ELQSVLTQPPSASGTPGQRVTIS CSGSSSNIGSNYVYWYQQLPGT APKILIYRNNQRPSGVPDRFSGS KSGTSASLAISGLRSEDEADYYC AAWDDNLSGWVFGTGTKLTVL (SEQ ID NO: 49) | QVQLVQSGAEVKKPGSSVKVSCK ASGDTFSSNAISWVRQAPGQGLE WMGVIIPIFGTADYAQKFQGRVTIT ADESTSTAYMELSSLRSEDTAVYY CARHTYHEYAGGYYGGAMX₁X₂W GQGTLVTVSS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 217) |
| B5-1 | DIQMTQSPSSLSASVGDRVTITC RASQSISSYLNWYQQKPGKAPK LLIYAASSLQSGVPSRFSGSGSG TDFTLTISSLQPEDFATYYCQQSY STPLTFGQGTKVEIK (SEQ ID NO: 51) | EVQLLESGGGLVQPGGSLRLSCA ASGFTFSNYAMSWVRQAPGKGLE WVSDISGGGGRTYYAX₁X₂VKGRF TISRDNSKNTLYLQMNSLRAEDTA VYYCARAGLLYGGGVYPMDIWG QGTLVTVS, wherein $X_1$ is R, H, K, D, E, S, T, N, Q, C, G, P, A, V, I, L, M, F, Y, or W, and $X_2$ is R, H, K, D, E, S, T, N, Q, C, G, P, A, V, I, L, M, F, Y, or W (SEQ ID NO: 218) |

Also provided herein are CDR portions of antigen binding domains of antibodies to EGFRvIII (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 2 provides examples of CDR sequences provided herein.

TABLE 2

| | Heavy Chain | | |
|---|---|---|---|
| mAb | CDRH1 | CDRH2 | CDRH3 |
| m62G7 | TDYTLH (SEQ ID NO: 62) (Kabat); GYTFTD (SEQ ID NO: 63) (Chothia); GYTFTDYTLH (SEQ ID NO: 64) (extended) | GIDPINGGTTYNQKFKG (SEQ ID NO: 65) (Kabat) GIDPINGGTTY (SEQ ID NO: 66) (Chothia) | GEAMDS (SEQ ID NO: 67) |
| h62G7 | TDYTLH (SEQ ID NO: 62) (Kabat); GYTFTD (SEQ ID NO: 63) (Chothia); GYTFTDYTLH (SEQ ID NO: 64) (extended) | GINPINGGTTYNQKFKG (SEQ ID NO: 68) (Kabat) GINPINGGTTY (SEQ ID NO: 69) (Chothia) | GEAMDS (SEQ ID NO: 67) |
| h62G7-H14 | TDYTLH (SEQ ID NO: 62) (Kabat); GYTFTD (SEQ ID NO: 63) (Chothia); GYTFTDYTLH (SEQ ID NO: 64) (extended) | GIWPITGGTTYNQKFKG (SEQ ID NO: 70) (Kabat) GIWPITGGTTY (SEQ ID NO: 71) (Chothia) | GEAEGS (SEQ ID NO: 72) |

TABLE 2-continued

| | | | |
|---|---|---|---|
| h62G7-EQ | TDYTLH (SEQ ID NO: 62) (Kabat); GYTFTD (SEQ ID NO: 63) (Chothia); GYTFTDYTLH (SEQ ID NO: 64) (extended) | GIWPITGGTTYNQKFKG (SEQ ID NO: 70) (Kabat) GIWPITGGTTY (SEQ ID NO: 71) (Chothia) | GEAQGS (SEQ ID NO: 73) |
| 42G9 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSTDEKSLKLSLRS (SEQ ID NO: 77) (Kabat) HIFSTDEKSL (SEQ ID NO: 78) (Chothia) | DSSNYEGYFDF (SEQ ID NO: 79) |
| 32A10 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSIRRSLRS (SEQ ID NO: 83) (Kabat) HIFSTDEKSI (SEQ ID NO: 84) (Chothia) | DSSNYEGYFDY (SEQ ID NO: 85) |
| 20B9 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSYSTSLRG (SEQ ID NO: 86) (Kabat) HIFSTDEKSY (SEQ ID NO: 87) (Chothia) | DSSNYEGYFDF (SEQ ID NO: 79) |
| 14C11 | NNARMGVS (SEQ ID NO: 88) (Kabat); GFSLNNAR (SEQ ID NO: 89) (Chothia); GFSLNNARMGVS (SEQ ID NO: 90) (extended) | HIFSTDEKSFRTSLRS (SEQ ID NO: 91) (Kabat) HIFSTDEKSF (SEQ ID NO: 92) (Chothia) | DSSNYEGYFDY (SEQ ID NO: 85) |
| 21E11 | SNVRMGVS (SEQ ID NO: 93) (Kabat); GFSLSNVR (SEQ ID NO: 94) (Chothia); GFSLSNVRMGVS (SEQ ID NO: 95) (extended) | HIFSSDEKSIRRSLRS (SEQ ID NO: 96) (Kabat) HIFSSDEKSI (SEQ ID NO: 97) (Chothia) | DSSNYEGYFDF (SEQ ID NO: 79) |
| 49B11 | SNVRMGVS (SEQ ID NO: 93) (Kabat); GFSLSNVR (SEQ ID NO: 94) (Chothia); GFSLSNVRMGVS (SEQ ID NO: 95) (extended) | HIFSSDEKSIRRSLRS (SEQ ID NO: 96) (Kabat) HIFSSDEKSI (SEQ ID NO: 97) (Chothia) | DSSNYEGYFDY (SEQ ID NO: 85) |
| 46E10 12H6 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSIRRSLRS (SEQ ID NO: 83) (Kabat) HIFSTDEKSI (SEQ ID NO: 84) (Chothia) | DSSNYEGYFDY (SEQ ID NO: 85) |
| 19A9 21E7 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSLRLSLRS (SEQ ID NO: 98) (Kabat) HIFSTDEKSL (SEQ ID NO: 78) (Chothia) | DSSNYEGYFDY (SEQ ID NO: 85) |
| 11B11 | SNAKMGVS (SEQ ID NO: 99) (Kabat); GFSLSNAK (SEQ ID NO: 100) (Chothia); GFSLSNAKMGVS (SEQ ID NO: 101) (extended) | HIFSTDEKSIRRSLRS (SEQ ID NO: 83) (Kabat) HIFSTDEKSI (SEQ ID NO: 84) (Chothia) | DSSNYEGYFDY (SEQ ID NO: 85) |
| 12B2 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSSDEKSYRLSLRS (SEQ ID NO: 102) (Kabat) HIFSSDEKSY (SEQ ID NO: 103) (Chothia) | DSSNYGGYFDY (SEQ ID NO: 104) |
| 11F10 | SNPRMGVS (SEQ ID NO: 74) (Kabat); | HIFSSDEKSYRLFLRS (SEQ ID NO: 105) | DSSDYEGYFDY (SEQ ID NO: 107) |

TABLE 2-continued

| | | | |
|---|---|---|---|
| | GFSLSNPR (SEQ ID NO: 75) (Chothia); GFSLSNPRMGVS (SEQ ID NO: 76) (extended) | (Kabat) HIFSSDEKSY (SEQ ID NO: 103) (Chothia) | |
| 17G11 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSSDEKSYRLSLRS (SEQ ID NO: 102) (Kabat) HIFSSDEKSY (SEQ ID NO: 103) (Chothia) | DSSNYEEYFDY (SEQ ID NO: 108) |
| 29D5 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSTDEKSYSPSLRG (SEQ ID NO: 106) (Kabat) HIFSTDEKSY (SEQ ID NO: 87) (Chothia) | DSSNYEGYFDY |
| 30D8 | SDAWMS (SEQ ID NO: 109) (Kabat); GFTFSD (SEQ ID NO: 110) (Chothia); GFTFSDAWMS (SEQ ID NO: 111) (extended) | RIKSKTDGGTTDYVVPLNG (SEQ ID NO: 112) (Kabat) RIKSKTDGGTTDY (SEQ ID NO: 113) (Chothia) | VPGSYGY (SEQ ID NO: 114) |
| 20E12 | SYAWMS (SEQ ID NO: 115) (Kabat); GFTFSY (SEQ ID NO: 116) (Chothia); GFTFSYAWMS (SEQ ID NO: 117) (extended) | RIKSIADGGATDYAAPVRN (SEQ ID NO: 118) (Kabat) RIKSIADGGATDY (SEQ ID NO: 119) (Chothia) | IPGNDAFDM (SEQ ID NO: 120) |
| 26B9 | NNAWMS (SEQ ID NO: 121) (Kabat); GFIFNN (SEQ ID NO: 122) (Chothia); GFIFNNAWMS (SEQ ID NO: 123) (extended) | RIKSKSDGGTTDYAAPVKD (SEQ ID NO: 124) (Kabat) RIKSKSDGGTTDY (SEQ ID NO: 125) (Chothia) | APGGPFDY (SEQ ID NO: 126) |
| 32G8 | SYAWMS (SEQ ID NO: 115) (Kabat); GFTFSY (SEQ ID NO: 116) (Chothia); GFTFSYAWMS (SEQ ID NO: 117) (extended) | RIKSITDGGVIDYAAPVRN (SEQ ID NO: 127) (Kabat) RIKSITDGGVIDY (SEQ ID NO: 128) (Chothia) | IPGNDDFDM (SEQ ID NO: 129) |
| 34E7 | SYAWMS (SEQ ID NO: 115) (Kabat); GFTFSY (SEQ ID NO: 116) (Chothia); GFTFSYAWMS (SEQ ID NO: 117) (extended) | RIKSINDGGATDYASPVRN (SEQ ID NO: 130) (Kabat) RIKSINDGGATDY (SEQ ID NO: 131) (Chothia) | IPGNDAFDM (SEQ ID NO: 120) |
| 20G5 | TNAWMS (SEQ ID NO: 132) (Kabat); GFTFTN (SEQ ID NO: 133) (Chothia); GFTFTNAWMS (SEQ ID NO: 134) (extended) | RIKSKIDGGTTDYAAPVKG (SEQ ID NO: 135) (Kabat) RIKSKIDGGTTDY (SEQ ID NO: 136) (Chothia) | APGGPFDY (SEQ ID NO: 126) |
| C6 | SSNAIS (SEQ ID NO: 137) (Kabat); GDTFSS (SEQ ID NO: 138) (Chothia); GDTFSSNAIS (SEQ ID NO: 139) (extended) | VIIPIFGTADYAQKFQG (SEQ ID NO: 140) (Kabat) VIIPIFGTADY (SEQ ID NO: 141) (Chothia) | HTYHEYAGGYYGGAMDP (SEQ ID NO: 142) |
| B5 | SNYAMS (SEQ ID NO: 143) (Kabat); GFTFSN (SEQ ID NO: 144) (Chothia); GFTFSNYAMS (SEQ ID NO: 145) (extended) | DISGGGGRTYYADSVKG (SEQ ID NO: 146) (Kabat) DISGGGGRTYY (SEQ ID NO: 147) (Chothia) | AGLLYGGGVYPMDI (SEQ ID NO: 148) |
| 42G9-1 | SNPRMGVS (SEQ ID NO: 74) (Kabat); GFSLSNPR (SEQ ID NO: 75) (Chothia); | HIFSTDEKSLKLSLRS (SEQ ID NOL 77) (Kabat) HIFSTDEKSL (SEQ ID | $X_1X_2$SNYEGYFDF, wherein $X_1$ is R, H, K, D, E, S, T, N, Q, C, G, P, A, V, I, |

TABLE 2-continued

| | | | |
|---|---|---|---|
| | GFSLSNPRMGVS (SEQ ID NO: 76) (extended) | NO: 78) (Chothia) | L, M, F, Y, or W, and X₂ is R, H, K, D, E, S, T, N, Q, C, G, P, A, V, I, L, M, F, Y, or W (SEQ ID NO: 219) |
| 32A10-1 | SNARMGVS (SEQ ID NO: 80) (Kabat); GFSLSNAR (SEQ ID NO: 81) (Chothia); GFSLSNARMGV (SEQ ID NO: 82) (extended) | HIFSTDEKSIRRSLRS (SEQ ID NO: 83) (Kabat); HIFSTDEKSI (SEQ ID NO: 84) (Chothia) | X₁X₂SNYEGYFDY, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 220) |
| 20B9-1 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSYSTSLRG (SEQ ID NO: 86) (Kabat) HIFSTDEKSY (SEQ ID NO: 87) (Chothia) | X₁X₂SNYEGYFDF, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 219) |
| 14C11-1 | NNARMGVS (SEQ ID NO: 88) (Kabat); GFSLNNAR (SEQ ID NO: 89) (Chothia); GFSLNNARMGVS (SEQ ID NO: 90) (extended) | HIFSTDEKSFRTSLRS (SEQ ID NO: 91) (Kabat) HIGSTDEKSF (SEQ ID NO: 92) (Chothia) | X₁X₂SNYEGYFDY, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 220) |
| 21E11-1 | SNVRMGVS (SEQ ID NO: 93) (Kabat); GFSLSNVR (SEQ ID NO: 94) (Chothia); GFSLSNVRMGVS (SEQ ID NO: 95) (extended) | HIFSSDEKSIRRSLRS (SEQ ID NO: 96) (Kabat) HIFSSDEKSI (SEQ ID NO: 97) (Chothia) | X₁X₂SNYEGYFDF, wherein X₁ is R, H, K, D, E, S, T, N Q, C, G, P, A, V, I, L, M, F, Y, or W, and X₂ is R, H, K, D, E, S, T, N, Q, C, G, P, A, V, I, L, M, F, Y, or W (SEQ ID NO: 219) |
| 49B11-1 | SNVRMGVS (SEQ ID NO: 93) (Kabat); GFSLSNVR (SEQ ID NO: 94) (Chothia); GFSLSNVRMGVS (SEQ ID NO: 95) (extended) | HIFSSDEKSIRRSLRS (SEQ ID NO: 96) (Kabat) HIFSSDEKSI (SEQ NO: 97) (Chothia) | X₁X₂SNYEGYFDY, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 220) |
| 46E10-1 12H6-1 | SNARMGVS (SEQ ID NO: 80) (Kabat); GFSLSNAR (SEQ ID NO: 81) (Chothia); GFSLSNARMGVS (SEQ ID NO: 82) (extended) | HIFSTDEKSIRRSLRS (SEQ ID NO: 83) (Kabat) HIFSTDEKSI (SEQ ID NO: 84) (Chothia) | X₁X₂SNYEGYFDY, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 220) |
| 19A9-1 21E7-1 | SNARMGVS (SEQ ID NO: 80) (Kabat); GFSLSNAR (SEQ ID NO: 81) (Chothia); GFSLSNARMGVS (SEQ ID | HIFSTDEKSLRLSLRS (SEQ ID NO: 98) (Kabat) HIFSTDEKSL (SEQ ID NO: 78) (Chothia) | X₁X₂SNYEGYFDY, wherein X₁ is R, H, K, D, E, S, T, N, Q, C, G, P, A, V, I, L, M, F, Y, or W, |

TABLE 2-continued

| | | | |
|---|---|---|---|
| | NO: 82) (extended) | | and X₂ is R, H, K, D, E, S, T, N, Q, C, G, P, A, V, I, L, M, F, Y, or W (SEQ ID NO: 220) |
| 11B11-1 | SNAKMGVS (SEQ ID NO: 99) (Kabat); GFSLSNAK (SEQ ID NO: 100) (Chothia); GFSLSNAKMGVS (SEQ ID NO: 101) (extended) | HIFSTDEKSIRRSLRS (SEQ ID NO: 83) (Kabat) HIFSTDEKSI (SEQ ID NO: 84) (Chothia) | X₁X₂SNYEGYFDY, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 220) |
| 12B2-1 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSSDEKSYRLSLRS (SEQ ID NO: 102) (Kabat) HIFSSDEKSY (SEQ ID NO: 103) (Chothia) | X₁X₂SNYGGYFDY, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 221) |
| 11F10-1 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSSDEKSYRLFLRS (SEQ ID NO: 105) (Kabat) HIFSSDEKSY (SEQ ID NO: 103) (Chothia) | X₁X₂SNYGGYFDY, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 222) |
| 17G11-1 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSSDEKSYRLSLRS (SEQ ID NO: 102) (Kabat) HIFSSDEKSY (SEQ ID NO: 103) (Chothia) | X₁X₂SNYGGYFDY, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 223) |
| 29D5-1 | SNPRMGVS (SEQ ID NO: 74) (Kabat); GFSLSNPR (SEQ ID NO: 75) (Chothia); GFSLSNPRMGVS (SEQ ID NO: 76) (extended) | HIFSTDEKSYSPSLRG (SEQ ID NO: 106) (Kabat) HIFSTDEKSY (SEQ ID NO: 87) (Chothia) | X₁X₂SNYGGYFDY, wherein X₁ is R, H, K, D, E, S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 220) |
| 30D8-1 | SDAWMS (SEQ ID NO: 109) (Kabat); GFTFSD (SEQ ID NO: 110) (Chothia); GFTFSDAWMS (SEQ ID NO: 111) (extended) | RIKSKTX₁X₂GTTDYVV PLNG, wherein X₁ is R, H, K, D, E, S, T, N, Q, C, G, P, A, V, I, L, M, F, Y, or W (SEQ ID NO: 224) (Kabat) RIKSKTX₁X₂GTTDY, wherein X₁ is R, H, K, D, E, S, T, N, Q, C, G, P, A, V, I, L, M, F, Y, or W, and X₂ is R, H, K, D, E, S, T, N, Q, C, G, Pa, A, V, I, L, M, F, Y or W (SEQ ID NO: 227) (Chothia) | VPGSYGY (SEQ ID NO: 114) |
| 20E12-1 | SYAWMS (SEQ ID NO: 115) (Kabat); GFTFSY (SEQ ID NO: 116) | RIKSIAX₁X₂GATDYAAP VRN, wherein X₁ is R, H, K, D, E, S, T, N, | IPGNDAFDM (SEQ ID NO: 120) |

TABLE 2-continued

| | | | |
|---|---|---|---|
| | (Chothia);<br>GFTFSYAWMS (SEQ ID NO: 117) (extended) | Q, C, G, P, A, V, I, L, M, F, Y, or W (SEQ ID NO: 226) (Kabat)<br>RIKSIAX₁X₂GATDY, wherein X₁ is R, H, K, D, E, S, T, N, Q, C, G, P, A, V, I, L, M, F, Y, or W, and X₂ is R, H, K, D, E, S, T, N, Q, C, G, Pa, A, V, I, L, M, F, Y or W (SEQ ID NO: 227) (Chothia) | |
| 26B9-1 | NNAWMS (SEQ ID NO: 121) (Kabat);<br>GFIFNN (SEQ ID NO: 122) (Chothia);<br>GFIFNNAWMS (SEQ ID NO: 123) (extended) | RIKSKSX₁X₂GTTDYAAP VKD, wherein X₁ is R, H, K, D, E, S, T, N, Q, C, G, P, A, V, I, L, M, F, Y, or W (SEQ ID NO: 228) (Kabat)<br>RIKSKSX₁X₂GTTDY, wherein X₁ is R, H, K, D, E, S, T, N, Q, C, G, P, A, V, I, L, M, F, Y, or W, and X₂ is R, H, K, D, E, S, T, N, Q, C, G, Pa, A, V, I, L, M, F, Y or W (SEQ ID NO: 229) (Chothia) | APGGPFDY (SEQ ID NO: 126) |
| 32G8-1 | SYAWMS (SEQ ID NO: 115) (Kabat);<br>GFTFSY (SEQ ID NO: 116) (Chothia);<br>GFTFSYAWMS (SEQ ID NO: 117) (extended) | RIKSITX₁X₂GVIDYAAP VKD, wherein X₁ is R, H, K, D, E, S, T, N, Q, C, G, P, A, V, I, L, M, F, Y, or W (SEQ ID NO: 230) (Kabat)<br>RIKSITX₁X₂GVIDY, wherein X₁ is R, H, K, D, E, S, T, N, Q, C, G, P, A, V, I, L, M, F, Y, or W, and X₂ is R, H, K, D, E, S, T, N, Q, C, G, Pa, A, V, I, L, M, F, Y or W (SEQ ID NO: 231) (Chothia) | IPGNDDFDM (SEQ ID NO: 129) |
| 34E7-1 | SYAWMS (SEQ ID NO: 115) (Kabat);<br>GFTFSY (SEQ ID NO: 116) (Chothia);<br>GFTFSYAWMS (SEQ ID NO: 117) (extended) | RIKSINX₁X₂GATDYASP VRN, wherein X₁ is R, H, K, D, E, S, T, N, Q, C, G, P, A, V, I, L, M, F, Y, or W (SEQ ID NO: 228) (Kabat)<br>RIKSINX₁X₂GATDY, wherein X₁ is R, H, K, D, E, S, T, N, Q, C, G, P, A, V, I, L, M, F, Y, or W, and X₂ is R, H, K, D, E, S, T, N, Q, C, G, Pa, A, V, I, L, M, F, Y or W (SEQ ID NO: 229) (Chothia) | IPGNDAFDM (SEQ ID NO: 120) |
| 20G5-1 | TNAWMS (SEQ ID NO: 132) (Kabat);<br>GFTFTN (SEQ ID NO: 133) (Chothia);<br>GFTFTNAWMS (SEQ ID NO: 134) (extended) | RIKSKIX₁X₂GTTDYAAP VRN, wherein X₁ is R, H, K, D, E, S, T, N, Q, C, G, P, A, V, I, L, M, F, Y, or W (SEQ ID NO: 234) (Kabat)<br>RIKSKIX₁X₂GTTDY, wherein X₁ is R, H, K, D, E, S, T, N, Q, C, G, P, A, V, I, L, M, F, Y, or W, and X₂ is R, H, K, D, E, S, T, N, Q, C, G, Pa, A, V, I, L, M, F, Y or W (SEQ ID NO: 235) (Chothia) | APGGPFDY (SEQ ID NO: 126) |
| C6-1 | SSNAIS (SEQ ID NO: 137) (Kabat);<br>GDTFSS (SEQ ID NO: 138) | VIIPIFGTADYAQKFQG (SEQ ID NO: 140) (Kabat) | HTYHEYAGGYYGG AMX₁X₂, wherein X₁ is R, H, K, D, E, |

TABLE 2-continued

|  | (Chothia); GDTFSSNAIS (SEQ ID NO: 139) (extended) | VIIPIFGTADY (SEQ ID NO: 141) (Chothia) | S, T, N, Q, C, G, P, A, V, I, L, M, F, Y, or W, and X₂ is R, H, K, D, E, S, T, N, Q, C, G, P, A, V, I, L, M, F, Y, or W (SEQ ID NO: 236) |
|---|---|---|---|
| B5 | SNYAMS (SEQ ID NO: 143) (Kabat); GFTFSN (SEQ ID NO: 144) (Chothia); GFTFSNYAMS (SEQ ID NO: 145) (extended) | DISGGGGRTYYAX₁X₂V KG, where in X1 is R, H, KJ, D, E, S, T, N, Q, C, G, P, A, V, I, L, M, F, Y, or W, and X2 is R, H, K, D, E, S, T, N, Q, C, G, P, A, V, I, L, M, F, Y, or W (SEQ ID NO: 237) (Kabat) DISGGGGRTYY (SEQ ID NO: 147) (Chothia) | AGLLYGGGVYPM DI (SEQ ID NO: 148) |

| Light Chain | | | |
|---|---|---|---|
| mAb | CDRL1 | CDRL2 | CDRL3 |
| m62G7 h62G7 | KSSQSLLYSNGKTYLN (SEQ ID NO: 149) | LVSKLDS (SEQ ID NO: 150) | VQDTHFPLT (SEQ ID NO: 151) |
| h62G7-L6 | KSSQSLLYSNGKTYLN (SEQ ID NO: 149) | QVSKLDS (SEQ ID NO: 152) | GQDTHFPLT (SEQ ID NO: 153) |
| h62G7-L1-DV | KSSQSLLYSNDKTYTN (SEQ ID NO: 154) | EVSKLDV (SEQ ID NO: 155) | GQDTHFPLT (SEQ ID NO: 153) |
| 42G9 | RASQSVRSNLA (SEQ ID NO: 156) | GSTIRAT (SEQ ID NO: 157) | QQYSDWPFT (SEQ ID NO: 158) |
| 32A10 | RASQSVSSNFA (SEQ ID NO: 159) | GATTRAT (SEQ ID NO: 160) | QQYKDWPFT (SEQ ID NO: 161) |
| 20B9 | RVSQSIGANLA (SEQ ID NO: 162) | GASTRAT (SEQ ID NO: 163) | QQYIYWPFT (SEQ ID NO: 164) |
| 14C11 | RASQSVSNNLA (SEQ ID NO: 165) | GASTRAT (SEQ ID NO: 163) | QQYKDWPFT (SEQ ID NO: 161) |
| 21E11 | RASQSVGSDLA (SEQ ID NO: 166) | GASTRAT (SEQ ID NO: 163) | QQYNDWPFT (SEQ ID NO: 167) |
| 49B11 | RASQNIGSDLA (SEQ ID NO: 168) | GASTRAT (SEQ ID NO: 163) | QQYNDWPFT (SEQ ID NO: 167) |
| 46E10 | RASQSVTSNFA (SEQ ID NO: 169) | GASTRAT (SEQ ID NO: 163) | QQYKDWPFT (SEQ ID NO: 161) |
| 12H6 | RASQGVSSNFA (SEQ ID NO: 170) | GASTRAT (SEQ ID NO: 163) | QQYKDWPFT (SEQ ID NO: 161) |
| 19A9 | RASQSVNRNLA (SEQ ID NO: 171) | GTSTRAT (SEQ ID NO: 172) | QQYNDWPFT (SEQ ID NO: 167) |
| 11811 | RASQSVSTNFA (SEQ ID NO: 173) | GASTRAT (SEQ ID NO: 163) | QQYKDWPFT (SEQ ID NO: 161) |
| 21E7 | RASQSVNSNLA (SEQ ID NO: 174) | GSSTRAT (SEQ ID NO: 175) | QQYNDWPFT (SEQ ID NO: 167) |
| 1282 17G11 | RASQSVINNLA (SEQ ID NO: 176) | GTSTRAT (SEQ ID NO: 172) | QDYNNWPFT (SEQ ID NO: 177) |
| 11F10 | RASQSVGSNLA (SEQ ID NO: 178) | GASTRASG (SEQ ID NO: 179) | QEYNNWPFT (SEQ ID NO: 180) |
| 29D5 | RANQIVSSNLA (SEQ ID NO: 181) | GTSTRAT (SEQ ID NO: 172) | QQYNDWPFT (SEQ ID NO: 167) |
| 30D8 | RSSQSLLHNKRNNYLD (SEQ ID NO: 182) | LASNRAS (SEQ ID NO: 183) | MQAQQTPIT (SEQ ID NO: 184) |
| 20E12 32G8 | RSSQSLLYSNGKNYLD (SEQ ID NO: 185) | LGSNRAS (SEQ ID NO: 186) | MQAQQTPIT (SEQ ID NO: 184) |

TABLE 2-continued

| | | | |
|---|---|---|---|
| 26B9 | RSSQSLLHRDGFNYLD (SEQ ID NO: 187) | LASSRAS (SEQ ID NO: 188) | MQALQTPIT (SEQ ID NO: 189) |
| 34E7 | RSTQSLLYSNGKNYLD (SEQ ID NO: 190) | LGSIRAS (SEQ ID NO: 191) | MQAQQTPIT (SEQ ID NO: 184) |
| 20G5 | RSSQSLLYSDRRNYLD (SEQ ID NO: 192) | LGSYRAS (SEQ ID NO: 193) | MQALQIPIT (SEQ ID NO: 194) |
| C6 | SGSSSNIGSNYVY (SEQ ID NO: 195) | RNNQRPS (SEQ ID NO: 196) | AAWDDNLSGWV (SEQ ID NO: 197) |
| B5 | RASQSISSYLN (SEQ ID NO: 198) | AASSLQS (SEQ ID NO: 199) | QQSYSTPLT (SEQ ID NO: 200) |
| 20E12-1 32G8-1 | RSSQSLLYSX$_1$X$_2$KNYLD, wherein X$_1$ is R, H, K, D, E, S, T, N, Q, C, G, P, A, V, I, L, M, F, Y, or W, and X$_2$ is R, H, K, D, E, S, T, N, Q, C, G, P, A, V, I, L, M, F, Y, or W (SEQ ID NO: 238) | LGSNRAS (SEQ ID NO: 186) | MQAQQTPIT (SEQ ID NO: 184) |
| 26B9-1 | RSSQSLLHRX$_1$X$_2$FNYLD, wherein X$_1$ is R, H, K, D, E, S, T, N, Q, C, G, P, A, V, I, L, M, F, Y, or W, and X$_2$ is R, H, K, D, E, S, T, N, Q, C, G, P, A, V, I, L, M, F, Y, or W (SEQ ID NO: 238) | LASSRAS (SEQ ID NO: 188) | MQALQTPIT (SEQ ID NO: 189) |

In some embodiments, the present invention provides an antibody that binds to EGFRvIII and competes with the antibody as described herein, including m62G7, h62G7, h62G7-H14/L1-DV, h62G7-EQ/L6, 42G9, 32A10, 20B9, 14C11, 21E11, 49B11, 46E10, 12H6, 19A9, 21E7, 11B11, 12B2, 11F10, 17G11, 29D5, 30D8, 20E12, 26B9, 32G8, 34E7, 20G5, C6, B5, 42G9-1, 32A10-1, 20B9-1, 14C11-1, 21E11-1, 49B11-1, 46E10-1, 12H6-1, 19A9-1, 21E7-1, 11B11-1, 12B2-1, 11F10-1, 17G11-1, 29D5-1, 30D8-1, 20E12-1, 26B9-1, 32G8-1, 34E7-1, 20G5-1, C6-1, and B5-1.

In some embodiments, the invention also provides CDR portions of antibodies to EGFRvIII antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity ($K_D$) of the EGFRvIII antibody as described herein to EGFRvIII (such as human EGFRvIII (e.g., (SEQ ID NO: 201)) can be about 0.001 to about 5000 nM. In some embodiments, the binding affinity is about any of 5000 nM, 4500 nM, 4000 nM, 3500 nM, 3000 nM, 2500 nM, 2000 nM, 1789 nM, 1583 nM, 1540 nM, 1500 nM, 1490 nM, 1064 nM, 1000 nM, 933 nM, 894 nM, 750 nM, 705 nM, 678 nM, 532 nM, 500 nM, 494 nM, 400 nM, 349 nM, 340 nM, 353 nM, 300 nM, 250 nM, 244 nM, 231 nM, 225 nM, 207 nM, 200 nM, 186 nM, 172 nM, 136 nM, 113 nM, 104 nM, 101 nM, 100 nM, 90 nM, 83 nM, 79 nM, 74 nM, 54 nM, 50 nM, 45 nM, 42 nM, 40 nM, 35 nM, 32 nM, 30 nM, 25 nM, 24 nM, 22 nM, 20 nM, 19 nM, 18 nM, 17 nM, 16 nM, 15 nM, 12 nM, 10 nM, 9 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, or 0.001 nM. In some embodiments, the binding affinity is less than about any of 5000 nM, 4000 nM, 3000 nM, 2000 nM, 1000 nM, 900 nM, 800 nM, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM, 1 nM, or 0.5 nM.

Bispecific antibodies, monoclonal antibodies that have binding specificities for at least two different antigens, can be prepared using the antibodies disclosed herein. Methods for making bispecific antibodies are known in the art (see, e.g., Suresh et al., Methods in Enzymology 121:210, 1986). Traditionally, the recombinant production of bispecific antibodies was based on the coexpression of two immunoglobulin heavy chain-light chain pairs, with the two heavy chains having different specificities (Millstein and Cuello, Nature 305, 537-539, 1983). Accordingly, in one aspect, provided is a bispecific antibody wherein the bispecific antibody is a full-length human antibody, comprising a first antibody variable domain of the bispecific antibody specifically binding to a target antigen (e.g., EGFRvIII), and comprising a second antibody variable domain of the bispecific antibody capable of recruiting the activity of a human immune effector cell by specifically binding to an effector antigen located on the human immune effector cell.

The human immune effector cell can be any of a variety of immune effector cells known in the art. For example, the immune effector cell can be a member of the human lymphoid cell lineage, including, but not limited to, a T cell (e.g., a cytotoxic T cell), a B cell, and a natural killer (NK) cell. The immune effector cell can also be, for example without limitation, a member of the human myeloid lineage, including, but not limited to, a monocyte, a neutrophilic granulocyte, and a dendritic cell. Such immune effector cells may have either a cytotoxic or an apoptotic effect on a target cell or other desired effect upon activation by binding of an effector antigen.

The effector antigen is an antigen (e.g., a protein or a polypeptide) that is expressed on the human immune effector cell. Examples of effector antigens that can be bound by the heterodimeric protein (e.g., a heterodimeric antibody or a bispecific antibody) include, but are not limited to, human CD3 (or CD3 (Cluster of Differentiation) complex), CD16, NKG2D, NKp46, CD2, CD28, CD25, CD64, and CD89.

The target cell can be a cell that is native or foreign to humans. In a native target cell, the cell may have been transformed to be a malignant cell or pathologically modified (e.g., a native target cell infected with a virus, a *plasmodium*, or a bacterium). In a foreign target cell, the cell is an invading pathogen, such as a bacterium, a *plasmodium*, or a virus.

The target antigen is expressed on a target cell in a diseased condition (e.g., an inflammatory disease, a proliferative disease (e.g., cancer), an immunological disorder, a neurological disease, a neurodegenerative disease, an autoimmune disease, an infectious disease (e.g., a viral infection or a parasitic infection), an allergic reaction, a graft-versus-host disease or a host-versus-graft disease). A target antigen is not effector antigen. In some embodiments, the target antigen is EGFRvIII.

In some embodiments, provided is a bispecific antibody wherein the bispecific antibody is a full-length human antibody, comprising a first antibody variable domain of the bispecific antibody specifically binding to a target antigen, and comprising a second antibody variable domain of the bispecific antibody capable of recruiting the activity of a human immune effector cell by specifically binding to an effector antigen located on the human immune effector cell, wherein the first antibody variable domain comprises a heavy chain variable (VH) region comprising a VH CDR1, VH CDR2, and VH CDR3 of the VH sequence shown in SEQ ID NO: 1, 3, 5, 7, 9, 11, 13, 15, 17, 19, 21, 23, 25, 27, 30, 32, 34, 35, 37, 39, 41, 43, 44, 46, 48, 50, 52, 53, 54, 55, 56, 57, 58, 59, 60, 61, 202, 203, 204, 205, 206, 207, 208, 209, 210, 214, 216, 217, or 218; and/or a light chain variable (VL) region comprising a VL CDR1, VL CDR2, and VL CDR3 of the VL sequence shown in SEQ ID NO: 2, 4, 6, 8, 10, 12, 14, 16, 18, 20, 22, 24, 26, 28, 29, 31, 33, 36, 38, 40, 42, 45, 47, 49, 51, 211, 212, 213, or 215.

In some embodiments, provided is a bispecific antibody wherein the bispecific antibody is a full-length human antibody, comprising a first antibody variable domain of the bispecific antibody specifically binding to a target antigen, and comprising a second antibody variable domain of the bispecific antibody capable of recruiting the activity of a human immune effector cell by specifically binding to an effector antigen located on the human immune effector cell, wherein the first antibody variable domain comprises (a) a heavy chain variable (VH) region comprising (i) a VH complementarity determining region one (CDR1) comprising the sequence shown in SEQ ID NO: 62, 63, 64, 74, 75, 76, 80, 81, 82, 88, 89, 90, 93, 94, 95, 99, 100, 101, 109, 110, 111, 115, 116, 117, 121, 122, 123, 132, 133, 134, 137, 138, 139, 143, 144, or 145; (ii) a VH CDR2 comprising the sequence shown in SEQ ID NO: 65, 66, 68, 69, 70, 71, 77, 78, 83, 84, 86, 87, 91, 92, 96, 97, 98, 102, 103, 105, 106, 112, 113, 118, 119, 124, 125, 127, 128, 130, 131, 135, 136, 140, 141, 146, 147, 224, 225, 226, 227, 228, 229, 230, 231, 232, 233, 234, 235, or 237; and iii) a VH CDR3 comprising the sequence shown in SEQ ID NO: 67, 72, 73, 79, 85, 104, 107, 108, 114, 120, 126, 129, 142, 148, 219, 220, 221, 222, 223, or 236; and/or (b) a light chain variable (VL) region comprising (i) a VL CDR1 comprising the sequence shown in SEQ ID NO: 149, 154, 156, 159, 162, 165, 166, 168, 169, 170, 171, 173, 174, 176, 178, 181, 182, 185, 187, 190, 192, 195, 198, 238, or 239; (ii) a VL CDR2 comprising the sequence shown in SEQ ID NO: 150, 152, 155, 157, 160, 163, 172, 175, 179, 183, 186, 188, 191, 193, 196, or 199; and (iii) a VL CDR3 comprising the sequence shown in SEQ ID NO: 151, 153, 158, 161, 164, 167, 177, 180, 184, 189, 194, 197, or 200.

In some embodiments, the second antibody variable domain comprises a heavy chain variable (VH) region comprising a VH CDR1, VH CDR2, and VH CDR3 of the VH sequence shown in SEQ ID NO: 240; and/or a light chain variable (VL) region comprising VL CDR1, VL CDR2, and VL CDR3 of the VL sequence shown in SEQ ID NO: 241.

In some embodiments, the second antibody variable domain comprises (a) a heavy chain variable (VH) region comprising (i) a VH complementary determining region one (CDR1) comprising the sequence shown in SEQ ID NO: 244, 110, or 245; (ii) a VH CDR2 comprising the sequence shown in SEQ ID NO: 246 or 247; and iii) a VH CDR3 comprising the sequence shown in SEQ ID NO: 248; and/or (b) a light chain variable (VL) region comprising (i) a VL CDR1 comprising the sequence shown in SEQ ID NO: 249; (ii) a VL CDR2 comprising the sequence shown in SEQ ID NO: 250; and (iii) a VL CDR3 comprising the sequence shown in SEQ ID NO: 251.

Table 3 shows the specific amino acid and nucleic acid sequences of the second antibody variable domain, which is specific to CD3. In Table 3, the underlined sequences are CDR sequences according to Kabat and in bold according to Chothia.

TABLE 3

| mAb | Light Chain | Heavy Chain |
| --- | --- | --- |
| h2B4_HNPS_VH 1d_T2 4K_VL | DIVMTQSPDSLAVSLGERATINC KSSQSLFNVRSRKNYLAWYQQK PGQPPKLLISWASTRESGVPDRF SGSGSGTDFTLTISSLQAEDVAV YYCKQSYDLFTFGSGTKLEIK (SEQ ID NO: 241) | EVQLVESGGGLVQPGGSLRLSCA ASGFTFSDYYMTWVRQAPGKGLE WVAFIRNRARGYTSDHNPSVKGR FTISRDNAKNSLYLQMNSLRAEDT AVYYCARDRPSYYVLDYWGQGTT VTVSS (SEQ ID NO: 240) |
| h2B4_HNPS_VH 1d-T2 4K_VL | GACATTGTGATGACTCAATCCC CCGACTCCCTGGCTGTGTCCCT CGGCGAACGCGCAACTATCAAC TGTAAAAGCAGCCAGTCCCTGT TCAACGTCCGGTCGAGGAAGAA CTACCTGGCCTGGTATCAGCAG AAACCTGGGCAGCCGCCGAAG CTTCTGATCTCATGGGCCTCAA | GAAGTCCAACTTGTCGAATCGGG AGGAGGCCTTGTGCAACCCGGT GGATCCCTGAGGCTGTCATGCG CGGCCTCGGGCTTCACCTTTTCC GATTACTACATGACCTGGGTCAG ACAGGCCCCTGGAAAGGGGTTG GAATGGGTGGCATTCATCCGGA ATAGAGCCCGCGGATACACTTCC |

TABLE 3-continued

| mAb | Light Chain | Heavy Chain |
|---|---|---|
| | CTCGGGAAAGCGGAGTGCCAG ATAGATTCTCCGGATCTGGCTC CGGAACCGACTTCACCCTGACG ATTTCGAGCTTGCAAGCGGAGG ATGTGGCCGTGTACTACTGCAA GCAGTCCTACGACCTCTTCACC TTTGGTTCGGGCACCAAGCTGG AGATCAAA (SEQ ID NO: 243) | GACCACAACCCCAGCGTGAAGG GGCGGTTCACCATTAGCCGCGA CAACGCCAAGAACTCCCTCTACC TCCAAATGAACAGCCTGCGGGC GGAGGATACCGCTGTGTACTACT GCGCCCGCGACCGGCCGTCCTA CTATGTGCTGGACTACTGGGGC CAGGGTACTACGGTCACCGTCT CCTCA (SEQ ID NO: 242) |

Table 4 shows the examples of CDR sequences of the second antibody variable domain, which is specific to CD3.

TABLE 4

| Heavy Chain | | | |
|---|---|---|---|
| mAb | CDRH1 | CDRH2 | CDRH3 |
| h2B4_H NPS | SDYYMT (SEQ ID NO: 244) (Kabat); GFTFSD (SEQ ID NO: 110) (Chothia); GFTFSDYYMT (SEQ ID NO: 245) (Extended) | FIRNRARGYTSDH (SEQ ID NO: 246) (Kabat) FIRNRARGYTSDHNPSVKG (SEQ ID NO: 247) (Extended) | DRPSYYVLDY (SEQ ID NO: 248) |

| Light Chain | | | |
|---|---|---|---|
| mAb | CDRH1 | CDRH2 | CDRH3 |
| h2B4-1d_T24K | KSSQSLFNVRSRKN YLA (SEQ ID NO: 249) | WASTRES (SEQ ID NO: 250) | KQSYDLFT (SEQ ID NO: 251) |

In some embodiments, a bispecific antibody provided herein which contains a CD3-specific variable domain contains an anti-CD3 sequence as provided in U.S. Publication No. 20160297885, which is hereby incorporated by reference for all purposes.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In another approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

In another approach, the bispecific antibodies are composed of amino acid modification in the first hinge region in one arm, and the substituted/replaced amino acid in the first hinge region has an opposite charge to the corresponding amino acid in the second hinge region in another arm. This approach is described in International Patent Application No. PCT/US2011/036419 (WO2011/143545).

In another approach, the formation of a desired heteromultimeric or heterodimeric protein (e.g., bispecific antibody) is enhanced by altering or engineering an interface between a first and a second immunoglobulin-like Fc region (e.g., a hinge region and/or a CH3 region). In this approach, the bispecific antibodies may be composed of a CH3 region, wherein the CH3 region comprises a first CH3 polypeptide and a second CH3 polypeptide which interact together to form a CH3 interface, wherein one or more amino acids within the CH3 interface destabilize homodimer formation and are not electrostatically unfavorable to homodimer formation. This approach is described in International Patent Application No. PCT/US2011/036419 (WO2011/143545).

In another approach, the bispecific antibodies can be generated using a glutamine-containing peptide tag engineered to the antibody directed to an epitope (e.g., EGFRvIII) in one arm and another peptide tag (e.g., a Lys-containing peptide tag or a reactive endogenous Lys) engineered to a second antibody directed to a second epitope in another arm in the presence of transglutaminase. This approach is described in International Patent Application No. PCT/IB2011/054899 (WO2012/059882).

In some embodiments, the heterodimeric protein (e.g., bispecific antibody) as described herein comprises a full-length human antibody, wherein a first antibody variable domain of the bispecific antibody specifically binding to a target antigen (e.g., EGFRvIII), and comprising a second antibody variable domain of the bispecific antibody capable of recruiting the activity of a human immune effector cell by specifically binding to an effector antigen (e.g., CD3) located on the human immune effector cell, wherein the first and second antibody variable domain of the heterodimeric protein comprise amino acid modifications at positions 223, 225, and 228 (e.g., (C223E or C223R), (E225R), and (P228E or P228R)) in the hinge region and at position 409 or 368 (e.g., K409R or L368E (EU numbering scheme)) in the CH3 region of human IgG2 (SEQ ID NO: 290).

In some embodiments, the first and second antibody variable domains of the heterodimeric protein comprise amino acid modifications at positions 221 and 228 (e.g., (D221R or D221E) and (P228R or P228E)) in the hinge region and at position 409 or 368 (e.g., K409R or L368E (EU numbering scheme)) in the CH3 region of human IgG1 (SEQ ID NO: 291).

In some embodiments, the first and second antibody variable domains of the heterodimeric protein comprise amino acid modifications at positions 228 (e.g., (P228E or P228R)) in the hinge region and at position 409 or 368 (e.g., R409 or L368E (EU numbering scheme)) in the CH3 region of human IgG4 (SEQ ID NO: 292).

The amino acid sequence of the wild type Fc regions of human IgG1, IgG2, and IgG4 are listed below:

IgG2
(SEQ ID NO: 290)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

IgG1
(SEQ ID NO: 291)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

IgG4
(SEQ ID NO: 292)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

-continued
CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the EGFRvIII antibody as described herein is a monoclonal antibody. For example, the EGFRvIII antibody is a humanized monoclonal antibody or a chimeric monoclonal antibody.

In some embodiments, the antibody comprises a modified constant region, such as, for example without limitation, a constant region that has increased potential for provoking an immune response. For example, the constant region may be modified to have increased affinity to an Fc gamma receptor such as, e.g., FcγRI, FcγRIIA, or FcγIII.

In some embodiments, the antibody comprises a modified constant region, such as a constant region that is immunologically inert, that is, having a reduced potential for provoking an immune response. In some embodiments, the constant region is modified as described in Eur. J. Immunol., 29:2613-2624, 1999; PCT Application No. PCT/GB99/01441; and/or UK Patent Application No. 98099518. The Fc can be human IgG1, human IgG2, human IgG3, or human IgG4. The Fc can be human IgG2 containing the mutation A330P331 to S330S331 (IgG2Δa), in which the amino acid residues are numbered with reference to the wild type IgG2 sequence. Eur. J. Immunol., 29:2613-2624, 1999. In some embodiments, the antibody comprises a constant region of IgG4 comprising the following mutations (Armour et al., Molecular Immunology 40 585-593, 2003): E233F234L235 to P233V234A235 (IgG4Δc), in which the numbering is with reference to wild type IgG4. In yet another embodiment, the Fc is human IgG4 E233F234L235 to P233V234A235 with deletion G236 (IgG4Δb). In another embodiment, the Fc is any human IgG4 Fc (IgG4, IgG4Δb or IgG4Δc) containing hinge stabilizing mutation S228 to P228 (Aalberse et al., Immunology 105, 9-19, 2002). In another embodiment, the Fc can be aglycosylated Fc.

In some embodiments, the constant region is aglycosylated by mutating the oligosaccharide attachment residue (such as Asn297) and/or flanking residues that are part of the glycosylation recognition sequence in the constant region. In some embodiments, the constant region is aglycosylated for N-linked glycosylation enzymatically. The constant region may be aglycosylated for N-linked glycosylation enzymatically or by expression in a glycosylation deficient host cell.

In some embodiments, the constant region has a modified constant region that removes or reduces Fc gamma receptor binding. For example, the Fc can be human IgG2 containing the mutation D265, in which the amino acid residues are numbered with reference to the wild type IgG2 sequence (SEQ ID NO: 290). Accordingly, in some embodiments, the constant region has a modified constant region having the sequence shown in SEQ ID NO: 252:

```
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCRVRCPRCPAPPVAGPSVFLFPPKPKDTLMISRTPEVTCVVVAVSHEDP
EVQFNWYVDGVEVHNAKTKPREEQFNSTFRVVSVLTVVHQDWLNGKEYKC
KVSNKGLPSSIEKTISKTKGQPREPQVYTLPPSREEMTKNQVSLTCLVKG
FYPSDIAVEWESNGQPENNYKTTPPMLDSDGSFFLYSRLTVDKSRWQQGN
VFSCSVMHEALHNHYTQKSLSLSPGK.
```

The nucleic acid encoding the sequence shown in SEQ ID NO: 252 is shown in SEQ ID NO: 253:

```
GCCTCCACCAAGGGCCCATCGGTCTTCCCCCTGGCGCCCTGCTCCAGGA
GCACCTCCGAGAGCACAGCGGCCCTGGGCTGCCTGGTCAAGGACTACTT
CCCCGAACCGGTGACGGTGTCGTGGAACTCAGGCGCTCTGACCAGCGGC
GTGCACACCTTCCCGGCTGTCCTACAGTCCTCAGGACTCTACTCCCTCA
GCAGCGTAGTGACCGTGCCCTCCAGCAACTTCGGCACCCAGACCTACAC
CTGCAACGTAGATCACAAGCCCAGCAACACCAAGGTGGACAAGACAGTT
GAGCGCAAATGTCGTGTCAGGTGCCCAAGGTGCCCAGCACCACCTGTGG
CAGGACCGTCAGTCTTCCTCTTCCCCCCAAAACCCAAGGACACCCTCAT
GATCTCCCGGACCCCTGAGGTCACGTGCGTGGTGGTGGCCGTGAGCCAC
GAAGACCCCGAGGTCCAGTTCAACTGGTACGTGGACGGCGTGGAGGTGC
ATAATGCCAAGACAAAGCCACGGGAGGAGCAGTTCAACAGCACGTTCCG
TGTGGTCAGCGTCCTCACCGTCGTGCACCAGGACTGGCTGAACGGCAAG
GAGTACAAGTGCAAGGTCTCCAACAAAGGCCTCCCATCCTCCATCGAGA
AAACCATCTCCAAAACCAAAGGGCAGCCCCGAGAACCACAGGTGTACAC
CCTGCCCCCATCCCGGGAGGAGATGACCAAGAACCAGGTCAGCCTGACC
TGCCTGGTCAAAGGCTTCTACCCCAGCGACATCGCCGTGGAGTGGGAGA
GCAATGGGCAGCCGGAGAACAACTACAAGACCACACCTCCCATGCTGGA
CTCCGACGGCTCCTTCTTCCTCTACAGCAGGCTCACCGTGGACAAGAGC
AGGTGGCAGCAGGGGAACGTCTTCTCATGCTCCGTGATGCATGAGGCTC
TGCACAACCACTACACACAGAAGAGCCTCTCCCTGTCTCCGGGTAAA.
```

In some embodiments, the constant region has a modified constant region having the sequence shown in SEQ ID NO: 254:

```
ASTKGPSVFPLAPCSRSTSESTAALGCLVKDYFPEPVTVSWNSGALTSG
VHTFPAVLQSSGLYSLSSVVTVPSSNFGTQTYTCNVDHKPSNTKVDKTV
ERKCEVECPECPAPPVAGPSVFLFPPKPKDTLMISRTPEVTCVVVAVSH
EDPEVQFNWYVDGVEVHNAKTKPREEQFNSTFRVVSVLTVVHQDWLNGK
EYKCKVSNKGLPSSIEKTISKTKGQPREPQVYTLPPSREEMTKNQVSLT
CEVKGFYPSDIAVEWESNGQPENNYKTTPPMLDSDGSFFLYSKLTVDKS
RWQQGNVFSCSVMHEALHNHYTQKSLSLSPGK.
```

The nucleic acid encoding the sequence shown in SEQ ID NO: 254 is shown in SEQ ID NO: 255:

```
GCCTCCACCAAGGGCCCATCGGTCTTCCCCCTGGCGCCCTGCTCCAGGA
GCACCTCCGAGAGCACAGCGGCCCTGGGCTGCCTGGTCAAGGACTACTT
CCCCGAACCGGTGACGGTGTCGTGGAACTCAGGCGCTCTGACCAGCGGC
GTGCACACCTTCCCGGCTGTCCTACAGTCCTCAGGACTCTACTCCCTCA
GCAGCGTAGTGACCGTGCCCTCCAGCAACTTCGGCACCCAGACCTACAC
CTGCAACGTAGATCACAAGCCCAGCAACACCAAGGTGGACAAGACAGTT
GAGCGCAAATGTGAGGTCGAGTGCCCAGAGTGCCCAGCACCACCTGTGG
CAGGACCGTCAGTCTTCCTCTTCCCCCCAAAACCCAAGGACACCCTCAT
GATCTCCCGGACCCCTGAGGTCACGTGCGTGGTGGTGGCCGTGAGCCAC
GAAGACCCCGAGGTCCAGTTCAACTGGTACGTGGACGGCGTGGAGGTGC
ATAATGCCAAGACAAAGCCACGGGAGGAGCAGTTCAACAGCACGTTCCG
TGTGGTCAGCGTCCTCACCGTCGTGCACCAGGACTGGCTGAACGGCAAG
GAGTACAAGTGCAAGGTCTCCAACAAAGGCCTCCCATCCTCCATCGAGA
AAACCATCTCCAAAACCAAAGGGCAGCCCCGAGAACCACAGGTGTACAC
CCTGCCCCCATCCCGGGAGGAGATGACCAAGAACCAGGTCAGCCTGACC
TGCCTGGTCAAAGGCTTCTACCCCAGCGACATCGCCGTGGAGTGGGAGA
GCAATGGGCAGCCGGAGAACAACTACAAGACCACACCTCCCATGCTGGA
CTCCGACGGCTCCTTCTTCCTCTACAGCAAGCTCACCGTGGACAAGAGC
AGGTGGCAGCAGGGGAACGTCTTCTCATGCTCCGTGATGCATGAGGCTC
TGCACAACCACTACACACAGAAGAGCCTCTCCCTGTCTCCGGGTAAA.
```

The amino acid of the human Kappa constant region is shown in SEQ ID NO: 256:

```
GTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC.
```

And the nucleic acid encoding the sequence of SEQ ID NO: 256 is shown in SEQ ID NO: 257:
```
GGAACTGTGGCTGCACCATCTGTCTTCATCTTCCCGCCATCTGATGAGC
AGTTGAAATCTGGAACTGCCTCTGTTGTGTGCCTGCTGAATAACTTCTA
TCCCAGAGAGGCCAAAGTACAGTGGAAGGTGGATAACGCCCTCCAATCG
GGTAACTCCCAGGAGAGTGTCACAGAGCAGGACAGCAAGGACAGCACCT
ACAGCCTCAGCAGCACCCTGACGCTGAGCAAAGCAGACTACGAGAAACA
CAAAGTCTACGCCTGCGAAGTCACCCATCAGGGCCTGAGCTCGCCCGTC
ACAAAGAGCTTCAACAGGGGAGAGTGTTAG.
```

One way of determining binding affinity of antibodies to EGFRvIII is by measuring binding affinity of the bivalent antibody to monomeric EGFRvIII protein. The affinity of an EGFRvIII antibody can be determined by surface plasmon resonance (Biacore™3000™ surface plasmon resonance (SPR) system, Biacore™, INC, Piscataway N.J.) equipped with pre-immobilized anti-mouse Fc or anti-human Fc using HBS-EP running buffer (0.01M HEPES, pH 7.4, 0.15 NaCl, 3 mM EDTA, 0.005% v/v Surfactant P20). Monomeric 8-histidine tagged human EGFRvIII extracellular domain can be diluted into HBS-EP buffer to a concentration of less than 0.5 µg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound EGFRvIII protein while keeping the activity of EGFRvIII antibodies on the chip for over 200 injections. Typically, serial dilutions (spanning concentrations of 0.1-10× estimated $K_D$) of purified 8-histidine tagged EGFRvIII samples are injected for 1 min at 100 µL/minute and dissociation times of up to 2 hours are allowed. The concentrations of the EGFRvIII proteins are determined by absorbance at 280 nm based on sequence specific extinction coefficient of the 8-histidine tagged EGFRvIII protein. Kinetic association rates ($k_{on}$ or $k_a$) and dissociation rates ($k_{off}$ or $k_d$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any monomeric EGFRvIII, including human EGFRvIII, EGFRvIII of another mammal (such as mouse EGFRvIII, rat EGFRvIII, or primate EGFRvIII), as well as different forms of EGFRvIII (e.g., glycosylated EGFRvIII). Binding affinity of an antibody is generally measured at 25° C., but can also be measured at 37° C.

The antibodies as described herein may be made by any method known in the art. For the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for EGFRvIII, or portions thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with cells expressing human EGFRvIII, a human EGFRvIII protein, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329, 112, 2008; U.S. Pat. No. 7,314,622.

In an alternative, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to EGFRvIII and greater efficacy in inhibiting EGFRvIII.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen binding site derived from a non-human immunoglobulin have been described, including chimeric antibodies having rodent or modified rodent V regions and their associated CDRs fused to human constant regions. See, for example, Winter et al. Nature 349:293-299, 1991, Lobuglio et al. Proc. Nat. Acad. Sci. USA 86:4220-4224, 1989, Shaw et al. J Immunol. 138:4534-4538, 1987, and Brown et al. Cancer Res. 47:3577-3583, 1987. Other references describe rodent CDRs grafted into a human supporting framework region (FR) prior to fusion with an appropriate human antibody constant region. See, for example, Riechmann et al. Nature 332:323-327, 1988, Verhoeyen et al. Science 239:1534-1536, 1988, and Jones et al. Nature 321: 522-525, 1986. Another reference describes rodent CDRs supported by recombinantly engineered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476, 1991, and in U.S. Pat. Nos. 6,180,377; 6,054,297; 5,997,867; 5,866,692; 6,210, 671; and 6,350,861; and in PCT Publication No. WO 01/27160.

The general principles related to humanized antibodies discussed above are also applicable to customizing antibodies for use, for example, in dogs, cats, primate, equines and bovines. Further, one or more aspects of humanizing an antibody described herein may be combined, e.g., CDR grafting, framework mutation and CDR mutation.

In one variation, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565, 332; 5,580,717; 5,733,743; and 6,265,150; and Winter et al., Annu. Rev. Immunol. 12:433-455, 1994. Alternatively, the phage display technology (McCafferty et al., Nature 348: 552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for EGFRvIII, or tumor antigens of interest.

The antibodies as described herein can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant regions in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a monoclonal antibody herein.

The EGFRvIII antibodies as described herein can be identified or characterized using methods known in the art, whereby reduction of EGFRvIII expression levels are detected and/or measured. In some embodiments, an EGFRvIII antibody is identified by incubating a candidate agent with EGFRvIII and monitoring binding and/or attendant reduction of EGFRvIII expression levels. The binding assay may be performed with purified EGFRvIII polypeptide(s), or with cells naturally expressing, or transfected to express, EGFRvIII polypeptide(s). In one embodiment, the binding assay is a competitive binding assay, where the ability of a candidate antibody to compete with a known EGFRvIII antibody for EGFRvIII binding is evaluated. The assay may be performed in various formats, including the ELISA format.

Following initial identification, the activity of a candidate EGFRvIII antibody can be further confirmed and refined by bioassays, known to test the targeted biological activities. Alternatively, bioassays can be used to screen candidates directly. Some of the methods for identifying and characterizing antibodies are described in detail in the Examples.

EGFRvIII antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an EGFRvIII or other tumor antigen antibody. In another example, the epitope to which the EGFRvIII antibody binds can be determined in a systematic screening by using overlapping peptides derived from the EGFRvIII sequence and determining binding by the EGFRvIII antibody. According to the gene fragment expression assays, the open reading frame encoding EGFRvIII is fragmented either randomly or by specific genetic constructions and the reactivity of the expressed fragments of EGFRvIII with the antibody to be tested is determined. The gene fragments may, for example, be produced by PCR and then transcribed and translated into protein in vitro, in the presence of radioactive amino acids. The binding of the antibody to the radioactively labeled EGFRvIII is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant EGFRvIII in which various fragments of the EGFRvIII protein have been replaced (swapped) with sequences from EGFRvIII from another species (e.g., mouse), or a closely related, but antigenically distinct protein (e.g., Trop-1). By assessing binding of the antibody to the mutant EGFRvIII, the importance of the particular EGFRvIII fragment to antibody binding can be assessed. In the case of EGFRvIII specific antibody (i.e. antibody that does not bind EGFRwt (wild type) or any other proteins), epitope can be deduced from the sequence alignment of EGFRvIII to EGFRwt.

Yet another method which can be used to characterize an EGFRvIII antibody is to use competition assays with other antibodies known to bind to the same antigen, i.e., various fragments on EGFRvIII, to determine if the EGFRvIII antibody binds to the same epitope as other antibodies. Competition assays are well known to those of skill in the art.

An expression vector can be used to direct expression of an EGFRvIII antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 263:621, 1988; Wu et al., J. Biol. Chem., 269:542, 1994; Zenke et al., Proc. Natl. Acad. Sci. USA, 87:3655, 1990; and Wu et al., J. Biol. Chem., 266:338, 1991. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1:51, 1994; Kimura, Human Gene Therapy, 5:845, 1994; Connelly, Human Gene Therapy, 1995, 1:185; and Kaplitt, Nature Genetics, 6:148, 1994). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Pat. No. 2,200,651; and EP Pat. No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 3:147, 1992); ligand-linked DNA (see, e.g., Wu, J. Biol. Chem., 264:16985, 1989); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 14:2411, 1994 and in Woffendin, Proc. Natl. Acad. Sci., 91:1581, 1994.

In some embodiments, the invention encompasses compositions, including pharmaceutical compositions, comprising antibodies described herein or made by the methods and having the characteristics described herein. As used herein, compositions comprise one or more antibodies that bind to EGFRvIII, and/or one or more polynucleotides comprising sequences encoding one or more these antibodies. These compositions may further comprise suitable excipients, such as pharmaceutically acceptable excipients including buffers, which are well known in the art.

The invention also provides methods of making any of these antibodies. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide comprises a sequence encoding the heavy chain and/or the light chain variable regions of antibody m62G7, h62G7, h62G7-H14/L1-DV, h62G7-EQ/L6, 42G9, 32A10, 20B9, 14C11, 21E11, 49B11, 46E10, 12H6, 19A9, 21E7, 11B11, 12B2, 11F10, 17G11, 29D5, 30D8, 20E12, 26B9, 32G8, 34E7, 20G5, C6, B5, 42G9-1, 32A10-1, 20B9-1, 14C11-1, 21E11-1, 49B11-1, 46E10-1, 12H6-1, 19A9-1, 21E7-1, 11B11-1, 12B2-1, 11F10-1, 17G11-1, 29D5-1, 30D8-1, 20E12-1, 26B9-1, 32G8-1, 34E7-1, 20G5-1, C6-1, or B5- 1. The sequence encoding the antibody of interest may be maintained in a vector in a host cell and the host cell can then be expanded and frozen for future use. Vectors (including expression vectors) and host cells are further described herein.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

In the recombinant humanized antibodies, the Fcγ portion can be modified to avoid interaction with Fcγ receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, for example, U.S. Pat. Nos. 5,997,867 and 5,866,692.

The invention encompasses modifications to the antibodies and polypeptides of the invention including variants shown in Table 5, including functionally equivalent antibodies which do not significantly affect their properties and variants which have enhanced or decreased activity and/or affinity. For example, the amino acid sequence may be mutated to obtain an antibody with the desired binding affinity to EGFRvIII. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 5 under the heading of "conservative substitutions." If such substitutions result in a change in biological activity, then more substantial changes, denominated "exemplary substitutions" in Table 5, or as further described below in reference to amino acid classes, may be introduced and the products screened. In some embodiments, substitution variants of antibodies provided herein have no more than 15, 14, 13, 12, 11, 10, 9, 8, 7, 6, 5, 4, 3, 2, or 1 conservative substitution in the VH or VL region as compared to the reference parent antibody. In some embodiments, the substitutions are not within a CDR of the VH or VL region.

TABLE 5

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala, Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acid residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, Chem. Immunol. 65:111-128, 1997; Wright and Morrison, TibTECH 15:26-32, 1997). The oligosaccharide side chains of the immunoglobulins affect the protein's function (Boyd et al., Mol. Immunol. 32:1311-1318, 1996; Wittwe and Howard, Biochem. 29:4175-4180, 1990) and the intramolecular interaction between portions of the glycoprotein, which can affect the conformation and presented three-dimensional surface of the glycoprotein (Jefferis and Lund, supra; Wyss and Wagner, Current Opin. Biotech. 7:409-416, 1996). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180, 1999).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., J. Biol. Chem. 272:9062-9070, 1997).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., Bio/Technology, 10:779-783, 1992; Barbas et al., Proc Nat. Acad. Sci, USA 91:3809-3813, 1994; Schier et al., Gene, 169:147-155, 1995; Yelton et al., J. Immunol., 155:1994-2004, 1995; Jackson et al., J. Immunol., 154(7):3310-9, 1995, Hawkins et al., J. Mol. Biol., 226:889-896, 1992; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using Biacore™ surface plasmon resonance analysis, which detects differences in binding affinity of about 2-fold or greater. Biacore™ is particularly useful when the starting antibody already binds with a relatively high affinity, for example a $K_D$ of about 10 nM or lower. Screening using Biacore™ surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., Gene 137(1):109-18, 1993.

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore™ surface plasmon resonance analysis, and selection using any method known in the art for selection, including phage display, yeast display, and ribosome display.

The invention also encompasses fusion proteins comprising one or more fragments or regions from the antibodies of this invention. In one embodiment, a fusion polypeptide is provided that comprises at least 10 contiguous amino acids of the variable light chain region shown in SEQ ID NOs: 2, 4, 6, 8, 10, 12, 14, 16, 18, 20, 22, 24, 26, 28, 29, 31, 33, 36, 38, 40, 42, 45, 47, 49, 51, 211, 212, 213, or 215, and/or at least 10 amino acids of the variable heavy chain region shown in SEQ ID NOs: 1, 3, 5, 7, 9, 11, 13, 15, 17, 19, 21, 23, 25, 27, 30, 32, 34, 35, 37, 39, 41, 43, 44, 46, 48, 50, 52, 53, 54, 55, 56, 57, 58, 59, 60, 61, 202, 203, 204, 205, 206, 207, 208, 209, 210, 214, 216, 217, or 218. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises one or more CDR(s). In still other embodiments, the fusion polypeptide comprises CDR H3 (VH CDR3) and/or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the EGFRvIII antibody embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The invention also provides isolated polynucleotides encoding the antibodies of the invention, and vectors and host cells comprising the polynucleotide.

Accordingly, the invention provides polynucleotides (or compositions, including pharmaceutical compositions), comprising polynucleotides encoding any of the following: m62G7, h62G7, h62G7-H14/L1-DV, h62G7-EQ/L6, 42G9, 32A10, 20B9, 14C11, 21E11, 49B11, 46E10, 12H6, 19A9, 21E7, 11B11, 12B2, 11F10, 17G11, 29D5, 30D8, 20E12, 26B9, 32G8, 34E7, 20G5, C6, B5, 42G9-1, 32A10-1, 20B9-1, 14C11-1, 21E11-1, 49B11-1, 46E10-1, 12H6-1, 19A9-1, 21E7-1, 11B11-1, 12B2-1, 11F10-1, 17G11-1, 29D5-1, 30D8-1, 20E12-1, 26B9-1, 32G8-1, 34E7-1, 20G5-1, C6-1, and B5- 1, or any fragment or part thereof having the ability to bind EGFRvIII.

In another aspect, the invention provides polynucleotides encoding any of the antibodies (including antibody fragments) and polypeptides described herein, such as antibodies and polypeptides having impaired effector function. Polynucleotides can be made and expressed by procedures known in the art.

In another aspect, the invention provides compositions (such as a pharmaceutical compositions) comprising any of the polynucleotides of the invention. In some embodiments, the composition comprises an expression vector comprising a polynucleotide encoding any of the antibodies described herein.

Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to EGFRvIII is effected by an immunoassay or FACS. A cell overexpressing the antibody or protein of interest can be identified.

EGFRvIII Antibody Conjugates

The present invention also provides a conjugate (or immunoconjugate) of the EGFRvIII antibody as described herein, wherein the antibody is conjugated to an agent (e.g., a cytotoxic agent) for targeted immunotherapy (e.g., antibody-drug conjugates) either directly or indirectly via a linker. For example, a cytotoxic agent can be linked or conjugated to the EGFRvIII antibody as described herein for targeted local delivery of the cytotoxic agent moiety to tumors (e.g., EGFRvIII expressing tumor).

Methods for conjugating cytotoxic agent or other therapeutic agents to antibodies have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Reactive cysteine residues engineered at specific sites of antibodies for specific drug conjugation with defined stoichiometry have also been described. See, e.g., Junutula et al., Nature Biotechnology, 26:925-932, 2008. Conjugation using an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent comprising or attached to a reactive amine) is also described in international applications WO2012/059882 and WO2015015448.

In some embodiments, the EGFRvIII antibody or the conjugate as described herein comprises an acyl donor glutamine-containing tag engineered at a specific site of the antibody (e.g., a carboxyl terminus, an amino terminus, or at another site in the EGFRvIII antibody). In some embodiments, the tag comprises an amino acid glutamine (Q) or an amino acid sequence LQG, LLQGG (SEQ ID NO: 258), LLQG (SEQ ID NO: 259), LSLSQG (SEQ ID NO: 260), GGGLLQGG (SEQ ID NO: 261), GLLQG (SEQ ID NO: 262), LLQ, GSPLAQSHGG (SEQ ID NO: 263), GLLQGG (SEQ ID NO: 264), GLLQGG (SEQ ID NO: 265), GLLQ (SEQ ID NO: 266), LLQLLQGA (SEQ ID NO: 267), LLQGA (SEQ ID NO: 268), LLQYQGA (SEQ ID NO: 269), LLQGSG (SEQ ID NO: 270), LLQYQG (SEQ ID NO: 271), LLQLLQG (SEQ ID NO: 272), SLLQG (SEQ ID NO: 273), LLQLQ (SEQ ID NO: 274), LLQLLQ (SEQ ID NO: 275), LLQGR (SEQ ID NO: 276), LLQGPP (SEQ ID NO: 277), LLQGPA (SEQ ID NO: 278), GGLLQGPP (SEQ ID NO: 279), GGLLQGA (SEQ ID NO: 280), LLQGPGK (SEQ ID NO: 281), LLQGPG (SEQ ID NO: 282), LLQGP (SEQ ID NO: 283), LLQP (SEQ ID NO: 284), LLQPGK (SEQ ID NO: 285), LLQAPGK (SEQ ID NO: 286), LLQGAPG (SEQ ID NO: 287), LLQGAP (SEQ ID NO: 288), and LLQLQG (SEQ ID NO: 289).

Also provided is an isolated antibody comprising an acyl donor glutamine-containing tag and an amino acid modification at position 222, 340, or 370 of the antibody (EU numbering scheme) wherein the modification is an amino acid deletion, insertion, substitution, mutation, or any combination thereof. In some embodiments, the amino acid modification is a substitution from lysine to arginine (e.g., K222R, K340R, or K370R).

The agents that can be conjugated to the EGFRvIII antibodies of the present invention include, but are not limited to, cytotoxic agents, immunomodulating agents, imaging agents, therapeutic proteins, biopolymers, or oligonucleotides.

Examples of a cytotoxic agent include, but are not limited to, anthracycline, an auristatin, a dolastatin, a combretastatin, a duocarmycin, a pyrrolobenzodiazepine dimer, an indolino-benzodiazepine dimer, an enediyne, a geldanamycin, a maytansine, a puromycin, a taxane, a *vinca* alkaloid, a camptothecin, a tubulysin, a hemiasterlin, a spliceostatin, a pladienolide, and stereoisomers, isosteres, analogs, or derivatives thereof.

The anthracyclines are derived from bacteria Strepomyces and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, 1998. Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other novel auristatins (such as the ones described in U.S. Publication No. 2013/0129753). In some embodiments, the auristatin is 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide) having the following structure:

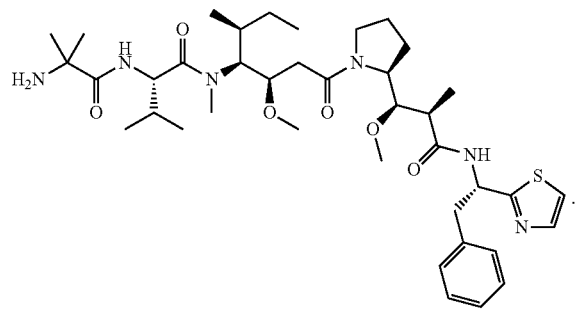 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C]

In some embodiments, the auristatin is 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide) having the following structure:

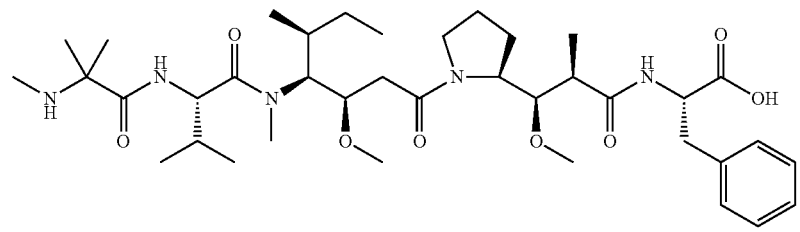 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C]

In some embodiments, the auristatin is 0131-OMe (N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methylL-valinamide) having the following structure:

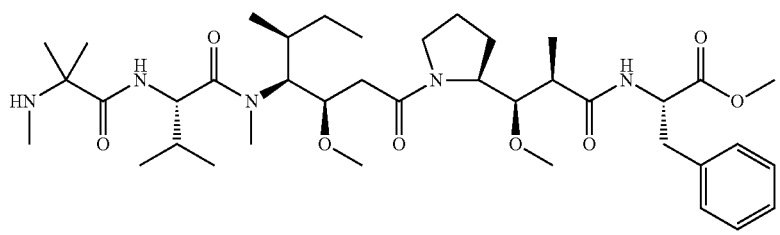 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)C(C)(C)NC)C(C)C]

In other embodiments, the auristatin is 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

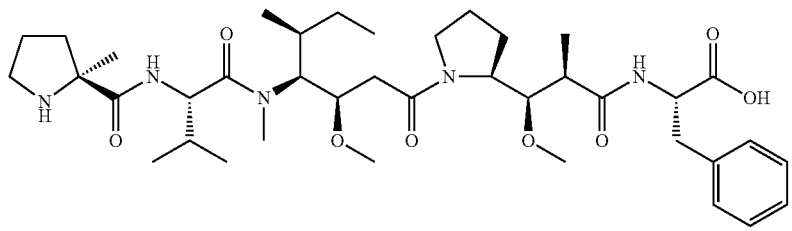 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C]

In other embodiments, the auristatin is 0121 (2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

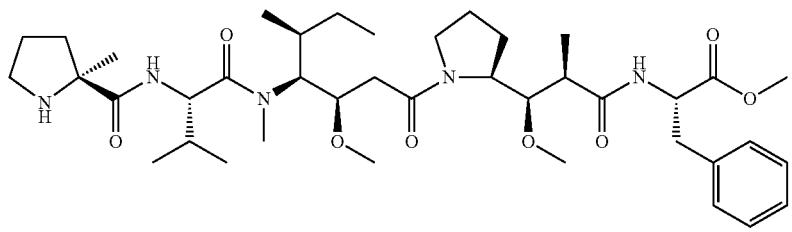 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1)C(C)C]

Camptothecin is a cytotoxic quinoline alkaloid which inhibits the enzyme topoisomerase I. Examples of camptothecin and its derivatives include, but are not limited to, topotecan and irinotecan, and their metabolites, such as SN-38.

n

Combretastatins are natural phenols with vascular disruption properties in tumors. Exemplary combretastatins and their derivatives include, but are not limited to, combretastatin A-4 (CA-4) and ombrabulin.

Duocarmycin and CC-1065 are DNA alkylating agents with cytotoxic potency. See Boger and Johnson, *PNAS* 92:3642-3649 (1995). Exemplary duocarmycin and CC-1065 include, but are not limited to, (+)-duocarmycin A and (+)-duocarmycin SA, (+)-CC-1065, and the compounds as disclosed in the international application PCT/IB2015/050280 including, but not limited to, N~2~-acetyl-L-lysyl-L-valyl-N~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide having the structure:

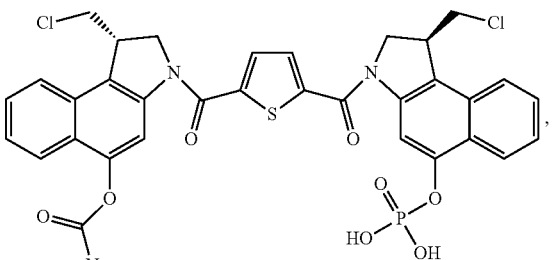
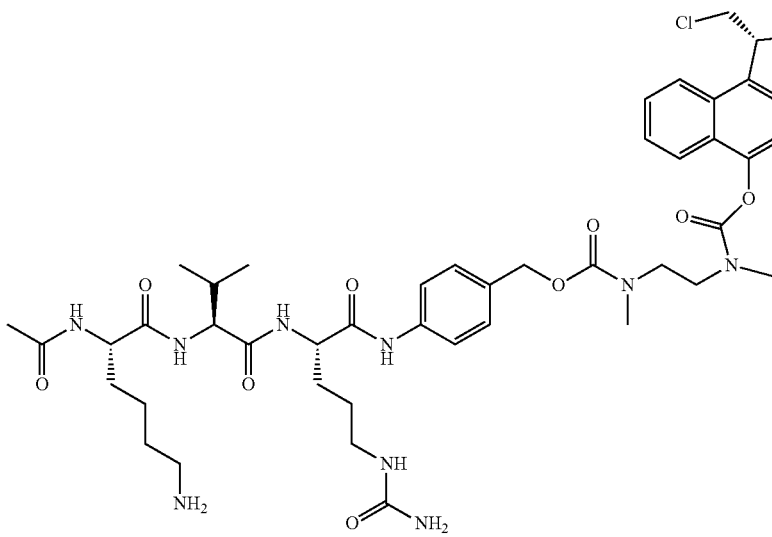

N~2~-acetyl-L-lysyl-L-valyl-N~5~-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]p ent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide having the structure:

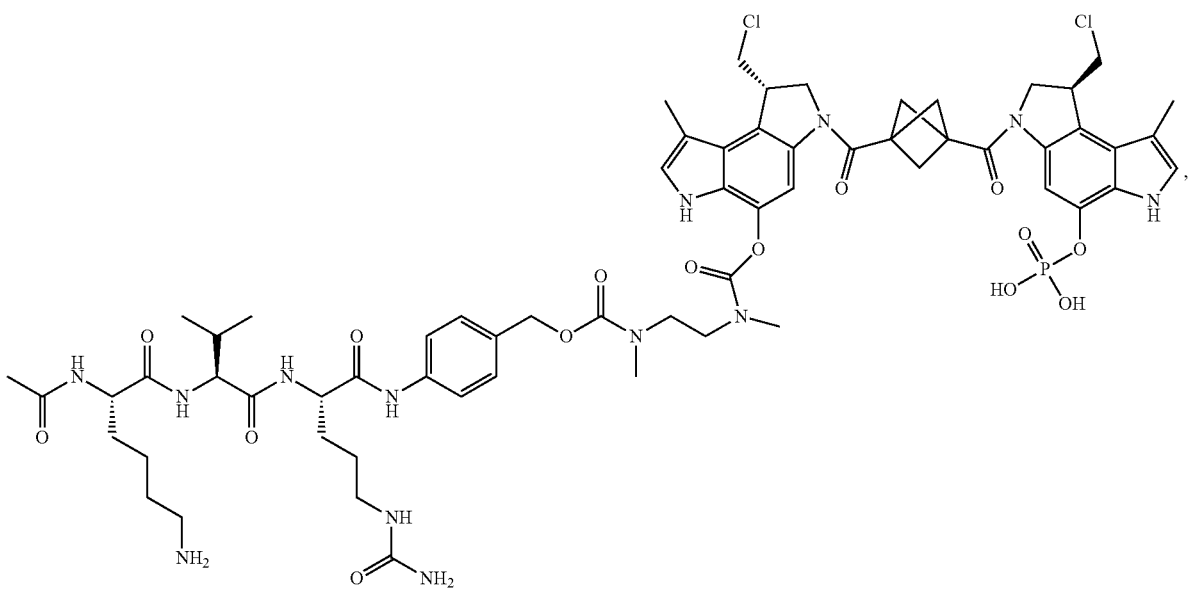 [SMILES: CC(=O)N[C@@H](CCCCN)C(=O)N[C@H](C(=O)N[C@@H](CCCNC(N)=O)C(=O)Nc1ccc(COC(=O)N(C)CCN(C)C(=O)Oc2cc3c(c4c(C)c[nH]c24)[C@H](CCl)CN3C(=O)C23CC(C(=O)N4C[C@@H](CCl)c5c4cc(OP(=O)(O)O)c4[nH]cc(C)c54)(C2)C3)cc1)C(C)C]

N~2~-acetyl-L-lysyl-L-valyl-N~5~-carbamoyl-N-[4-({[(2-{[({(8S)-8-(chloromethyl)-6-[(4-{[(1S)-1-(chloromethyl)-8-methyl-5-(phosphonooxy)-1,6-dihydropyrrolo[3,2-e]indol-3(2H)-yl]carbonyl}pentacyclo[4.2.0.0~2,5~.0~3,8~.0~4,7~]oct-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide having the structure:

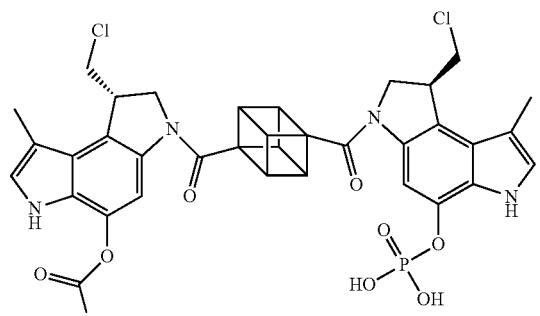
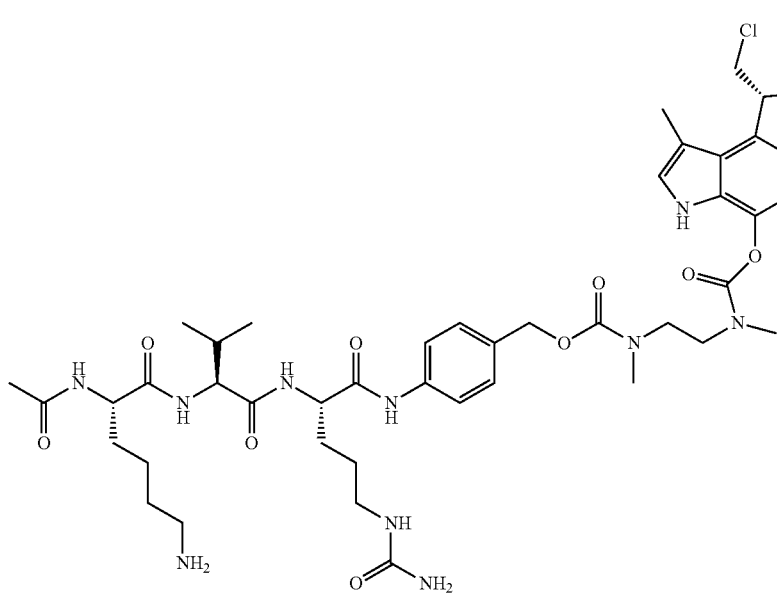

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, uncialamicin, dynemicin, and their derivatives.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethylaminoethylamino-17-demethoxygeldanamycin).

Hemiasterlin and its analogues (e.g., HTI-286) bind to the tubulin, disrupt normal microtubule dynamics, and, at stoichiometric amounts, depolymerize microtubules.

Maytansines or their derivatives maytansinoids inhibit cell proliferation by inhibiting the microtubules formation during mitosis through inhibition of polymerization of tubulin. See Remillard et al., Science 189:1002-1005, 1975. Exemplary maytansines and maytansinoids include, but are not limited to, mertansine (DM1) and its derivatives as well as ansamitocin.

Pyrrolobenzodiazepine dimers (PBDs) and indolino-benzodiazepine dimers (IGNs) are anti-tumor agents that contain one or more immine functional groups, or their equivalents, that bind to duplex DNA. PBD and IGN molecules are based on the natural product athramycin, and interact with DNA in a sequence-selective manner, with a preference for purine-guanine-purine sequences. Exemplary PBDs and their analogs include, but are not limited to, SJG-136.

Spliceostatins and pladienolides are anti-tumor compounds which inhibit splicing and interacts with spliceosome, SF3b. Examples of spliceostatins include, but are not limited to, spliceostatin A, FR901464, and (2S,3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2, 5-dim ethyltetrahydro-2H-pyran-3-yl]amino}-5-oxopent-3-en-2-yl acetate having the structure of

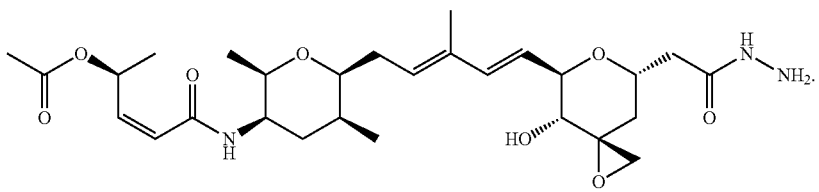 [SMILES: CC(=O)O[C@@H](C)/C=C\C(=O)N[C@@H]1C[C@H](C)[C@H](C/C=C(C)/C=C/[C@H]2O[C@H](CC(=O)NN)C[C@@]3(CO3)[C@@H]2O)O[C@@H]1C]

Examples of pladienolides include, but are not limited to, Pladienolide B, Pladienolide D, or E7107.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Tubulysins are natural products isolated from a strain of myxobacteria that has been shown to depolymerize microtubules and induce mitotic arrest. Exemplary tubulysins include, but are not limited to, tubulysin A, tubulysin B, and tubulysin D.

Vinca alkyloids are also anti-tubulin agents. Exemplary vinca alkyloids include, but are not limited to, vincristine, vinblastine, vindesine, and vinorelbine.

Accordingly, in some embodiments, the cytotoxic agent is selected from the group consisting of MMAD (Monomethyl Auristatin D), 0101 (2-methylalanyl-N-[(3R,4S,5S)-3-methoxy-1-{(2 S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L- valinamide), 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide), 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide), 0131-OMe (N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methylL-valinamide), 0121(2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide), and (2S,3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate.

In some embodiments, the agent is an immunomodulating agent. Examples of an immunomodulating agent include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof.

In some embodiments, the agent moiety is an imaging agent (e.g., a fluorophore or a chelator), such as fluorescein, rhodamine, lanthanide phosphors, and their derivatives thereof, or a radioisotope bound to a chelator. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101). Examples of chelators include, but are not limited to, 1,4,7,10-tetraazacyclododecane-N,N',N'',N'''-tetraacetic acid (DOTA), 1,4,7-triazacyclononane-1,4,7-triacetic acid (NOTA), 1,4,7-triazacyclononane, 1-glutaric acid-4, 7-acetic acid (deferoxamine), diethylenetriaminepentaacetic acid (DTPA), and 1,2-bis(o-aminophenoxy)ethane-N,N,N',N'-tetraacetic acid) (BAPTA).

In some embodiments, therapeutic or diagnostic radioisotopes or other labels (e.g., PET or SPECT labels) can be incorporated in the agent for conjugation to the EGFRvIII antibodies as described herein. Examples of a radioisotope or other labels include, but are not limited to, $^{3}H$, $^{11}C$, $^{13}N$, $^{14}C$, $^{15}N$, $^{15}O$, $^{35}B$, $^{18}F$, $^{32}P$, $^{33}P$, $^{47}Sc$, $^{51}Cr$, $^{57}Co$, $^{58}Co$, $^{59}Fe$, $^{62}Cu$, $^{64}Cu$, $^{67}Cu$, $^{67}Ga$, $^{68}Ga$, $^{75}Se$, $^{76}Br$, $^{77}Br$, $^{86}Y$, $^{89}Zr$, $^{90}Y$, $^{94}Tc$, $^{95}Ru$, $^{97}Ru$, $^{99}Tc$, $^{103}Ru$, $^{105}Rh$, $^{105}Ru$, $^{107}Hg$, $^{109}Pd$, $^{111}Ag$, $^{111}In$, $^{113}In$, $^{121}Te$, $^{122}Te$, $^{123}I$, $^{124}I$, $^{125}I$, $^{125}Te$, $^{126}I$, $^{131}I$, $^{131}In$, $^{133}I$, $^{142}Pr$, $^{143}Pr$, $^{153}Pb$, $^{153}Sm$, $^{161}Tb$, $^{165}Tm$, $^{166}Dy$, $^{166}H$, $^{167}Tm$, $^{168}Tm$, $^{169}Yb$, $^{177}Lu$, $^{186}Re$, $^{188}Re$, $^{189}Re$, $^{197}Pt$, $^{198}Au$, $^{199}Au$, $^{201}Tl$, $^{203}Hg$, $^{211}At$, $^{212}Bi$, $^{212}Pb$, $^{213}Bi$, $^{223}Ra$, $^{224}Ac$, or $^{225}Ac$.

In some embodiments, the agent is a therapeutic protein including, but is not limited to, a toxin, a hormone, an enzyme, and a growth factor.

Examples of a toxin protein (or polypeptide) include, but are not limited to, dipththeria (e.g., diphtheria A chain), *Pseudomonas* exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase I, Staphylococcal enterotoxin-A, pokeweed antiviral protein, gelonin, diphtherin toxin, *Phytolaca americana* proteins (PAPI, PAPII, and PAP-S), *momordica charantia* inhibitor, curcin, crotin, *sapaonaria officinalis* inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

In some embodiments, the agent is a biocompatible polymer. The EGFRvIII antibodies as described herein can be conjugated to the biocompatible polymer to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some embodiments, the agent is an oligonucleotide, such as anti-sense oligonucleotides.

In another aspect, the invention provides a conjugate of the antibody as described herein, wherein the conjugate comprises the formula: antibody-(acyl donor glutamine-containing tag)-(linker)-(cytotoxic agent).

Examples of a linker containing one or more reactive amines include, but are not limited to, Ac-Lys-Gly (acetyl-lysine-glycine), aminocaproic acid, Ac-Lys-β-Ala (acetyl-lysine-β-alanine), amino-PEG2 (polyethylene glycol)-C2, amino-PEG3-C2, amino-PEG6-C2 (or amino PEG6-propionyl), Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC, putrescine, or Ac-Lys-putrescine.

Methods of Using the EGFRvIII Antibodies and the Antibody Conjugates Thereof

The antibodies or the antibody conjugates of the present invention are useful in various applications including, but are not limited to, therapeutic treatment methods and diagnostic treatment methods.

The antibodies (e.g., monospecific and bispecific) and the antibody conjugates obtained by the methods described above can be used as a medicament. In some embodiments, such a medicament can be used for treating cancer, including solid tumors and liquid tumors. In some embodiments, the cancer is EGFRvIII related cancer including, but not limited to, glioblastoma (e.g., glioblastoma multiform), anaplastic astrocytoma, giant cell glioblastoma, gliosarcoma, anaplastic oligodendroglioma, anaplastic ependymoma, anaplastic oligoastrocytoma, choroid plexus carcinoma, anaplastic ganglioglioma, pineoblastoma, pineocytoma, meningioma, medulloepithelioma, ependymoblastoma, medulloblastoma, supraentorial primitive neuroectodermal tumor, atypical teratoid/rhabdoid tumor, mixed glioma, head and neck cancer, non-small cell lung cancer, breast cancer, ovarian cancer, prostate cancer, medullobastoma, colorectal cancer, anal cancer, cervical cancer, renal cancer, skin cancer, pancreatic cancer, liver cancer, bladder cancer, gastric cancer, thyroid cancer, mesothelioma, uterine cancer, lymphoma, or leukemia.

In some embodiments, provided is a method of inhibiting tumor growth or progression in a subject who has malignant cells expressing EGFRvIII, comprising administering to the subject in need thereof an effective amount of a composition comprising the EGFRvIII antibodies or the EGFRvIII antibody conjugates as described herein. In other embodiments, provided is a method of inhibiting metastasis of cells expressing EGFRvIII in a subject, comprising administering to the subject in need thereof an effective amount of a composition comprising the EGFRvIII antibodies or the EGFRvIII antibody conjugates as described herein. In other embodiments, provided is a method of inducing tumor regression in malignant cells in a subject, comprising administering to the subject in need thereof an effective amount of a composition comprising the EGFRvIII antibodies or the EGFRvIII antibody conjugates as described herein.

In some embodiments, the antibody (e.g., monospecific or bispecific) or the antibody conjugate according to the invention can be used in the manufacture of a medicament for treatment of a cancer in a patient in need thereof.

In some embodiments, the treatment can be in combination with one or more therapies against cancer selected from the group of antibodies therapy, chemotherapy, cytokines therapy, targeted therapy, vaccine therapy, dendritic cell therapy, gene therapy, hormone therapy, surgical resection, laser light therapy and radiation therapy. For example, the antibody (monospecific or bispecific) or the antibody conjugate of the invention can be administered to a patient in conjunction with (e.g., before, simultaneously, or following) 1) standard of care, including radiation, surgical resection, chemotherapy (e.g., temozolomide, procarbazine, carmustine, lomustine, vincristine etc.), antibody therapy such as bevacizumab, anti-angiogenic therapy, and/or tumor treating fields; 2) vaccine, including EGFRvIII vaccine; 3) targeted therapy, such as kinase inhibitors (e.g. everolimus); and 4) immunotherapies, including but not limited to anti-PD-1, anti-PD-L1, anti-PD-L2, anti-41BB, anti-TIM3, anti-LAG3, anti-TIGIT, anti-OX40, anti-HVEM, anti-BTLA, anti-CD40, anti-CD47, anti-CSF1R, anti-CSF1, anti-MARCO, anti-IL8, anti-CXCR4, and anti-CTLA4 antibodies.

The administration of the antibodies (e.g., monospecific or bispecific) or the antibody conjugates according to the invention may be carried out in any convenient manner, including by aerosol inhalation, injection, ingestion, transfusion, implantation or transplantation. The compositions described herein may be administered to a patient subcutaneously, intradermally, intratumorally, intracranially, intranodally, intramedullary, intramuscularly, by intravenous or intralymphatic injection, or intraperitoneally. In one embodiment, the heteromultimeric antibody compositions of the invention are preferably administered by intravenous injection.

In some embodiments, the administration of the antibodies (e.g., monospecific or bispecific) or the antibody conjugates can comprise administration of, for example, about 0.01 to about 20 mg per kg body weight including all integer values of mg per kg within those ranges. In some embodiments, the administration of the antibodies or the antibody conjugates can comprise administration of about 0.1 to 10 mg per kg body weight including all integer values of mg per kg within those ranges. The heteromultimeric antibody can be administrated in one or more doses. In some embodiments, said effective amount of the antibody or the antibody conjugate can be administrated as a single dose. In some embodiments, said effective amount of antibodies can be administrated as more than one dose over a period time. Timing of administration is within the judgment of managing physician and depends on the clinical condition of the patient. While individual needs vary, determination of optimal ranges of effective amounts of a given antibody (e.g., monospecific or bispecific) or antibody conjugate for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of heteromultimeric antibody or composition comprising those antibodies are administrated parenterally. In some embodiments, administration can be an intravenous administration. In some embodiments, administration can be directly done by injection within a tumor.

In some embodiments, anti-EGFRvIII antibodies provided herein may be used for diagnostic purposes, such in assays to identify EGFRvIII protein in samples (e.g. in immunohistochemistry assays) or in patients.

Compositions

In one aspect, the present invention provides a pharmaceutical composition comprising an antibody (e.g., monospecific or bispecific) or an antibody conjugate, of the invention or portion thereof as described above in a pharmaceutically acceptable carrier. In certain embodiments, the polypeptides of the invention may be present in a neutral form (including zwitter ionic forms) or as a positively or negatively-charged species. In some embodiments, the polypeptides may be complexed with a counterion to form a "pharmaceutically acceptable salt," which refers to a complex comprising one or more polypeptides and one or more counterions, where the counterions are derived from pharmaceutically acceptable inorganic and organic acids and bases.

The antibody (e.g., monospecific or bispecific) or the antibody conjugate, or portions thereof, may be administered alone or in combination with one or more other polypeptides of the invention or in combination with one or more other drugs (or as any combination thereof). The pharmaceutical compositions, methods and uses of the invention thus also encompass embodiments of combinations (co-administration) with other active agents, as detailed below.

As used herein, the terms "co-administration," "co-administered" and "in combination with," referring to the antibodies of the invention and one or more other therapeutic agents, is intended to mean, and does refer to and include the following: (i) simultaneous administration of such combination of a heterodimer disclosed herein and therapeutic agent(s) to a patient in need of treatment, when such components are formulated together into a single dosage form which releases said components at substantially the same time to said patient; (ii) substantially simultaneous administration of such combination of a heterodimer disclosed herein and therapeutic agent(s) to a patient in need of treatment, when such components are formulated apart from each other into separate dosage forms which are taken at substantially the same time by said patient, whereupon said components are released at substantially the same time to said patient; (iii) sequential administration of such combination of a heterodimer disclosed herein and therapeutic agent(s) to a patient in need of treatment, when such components are formulated apart from each other into separate dosage forms which are taken at consecutive times by said patient with a significant time interval between each administration, whereupon said components are released at substantially different times to said patient; and (iv) sequential administration of such combination of a heterodimer disclosed herein and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

Generally, the antibody (e.g., monospecific or bispecific) or the antibody conjugate disclosed herein or portions thereof are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the heterodimeric proteins and portions thereof disclosed herein.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include controlled, delayed, sustained, pulsed, targeted and programmed release formulations. For example, in one aspect, sterile injectable solutions can be prepared by incorporating the heterodimeric protein, e.g., bispecific antibody, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the invention is a formulation as a sterile aqueous solution having a pH that ranges from about 5.0 to about 6.5 and comprising from about 1 mg/mL to about 200 mg/mL of an antibody (e.g., monospecific or bispecific) or an antibody conjugate disclosed herein, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of an antibody (e.g., monospecific or bispecific) or an antibody conjugate disclosed herein is typically in the range of about 0.5 to about 1200 mg per patient, depending, of course, on the mode of administration, mechanism of action, and target biology. For example, an intravenous monthly dose may require about 1 to about 1000 mg/patient. The total monthly dose may be administered in single or divided doses and may, at the physician's discretion, fall outside of the typical range given herein.

An exemplary, non-limiting range for a therapeutically or prophylactically effective amount of an antibody (e.g., monospecific or bispecific) or an antibody conjugate, disclosed herein is about 1 to about 1000 mg/patient/month. In certain embodiments, the heterodimeric protein may be administered at about 1 to about 200 or about 1 to about 150 mg/patient/month.

Kits

The invention also provides kits for use in the instant methods. Kits of the invention include one or more containers comprising the antibody (e.g., monospecific or bispecific) or the antibody conjugate as described herein and instructions for use in accordance with any of the methods of the invention described herein. Generally, these instructions comprise a description of administration of the heterodimeric protein for the above described therapeutic treatments.

The instructions relating to the use of the antibody (e.g., monospecific or bispecific) or the antibody conjugate as described herein generally include information as to dosage, dosing schedule, and route of administration for the intended treatment. The containers may be unit doses, bulk packages (e.g., multi-dose packages) or subunit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a bispecific antibody. The container may further comprise a second pharmaceutically active agent.

Kits may optionally provide additional components such as buffers and interpretive information. Normally, the kit comprises a container and a label or package insert(s) on or associated with the container.

Incorporated by reference herein for all purposes is the content of U.S. Provisional Patent Application Nos. 62/281, 543 (filed Jan. 21, 2016) and 62/431,766 (Filed Dec. 8, 2016).

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1: Affinity Determination for Recombinant Anti-EGFRvIII Murine-Human Chimeric Antibody and Humanized Antibodies This example determines the affinity of chimeric and humanized anti-EGFRvIII antibodies at 25° C. and 37° C.

Anti-EGFRvIII mouse (m) antibody, m62G7, generated from hybridomas was sequenced and subcloned into suitable vectors for expression as murine-human chimeric antibodies. The CDRs of mouse antibody m62G7 were grafted onto human framework and expressed as human IgG1 recombinant antibody, h62G7. Affinity variants of h62G7 were made by introducing mutations in the CDRs of the heavy and light chains. The affinities of recombinant anti-EGFRvIII chimeric antibody m62G7 and humanized h62G7 antibodies were measured on a surface plasmon resonance Biacore™ T200 biosensor equipped with a research-grade anti-human Fc coupled CM4 sensor chip (GE Healthcare Inc., Piscataway, N.J.). Anti-EGFRvIII antibodies were then captured by anti-human Fc. Monomeric 8-histidine tagged human EGFRvIII extracellular domain was then injected as the analyte at 10-fold dilution series with top concentration at 1000 nM. Affinity of anti-EGFRvIII antibodies towards human EGFRvIII was measured at both 25° C. and 37° C. (Table 6). None of these antibodies showed detectable binding to 1000 nM 8-histidine tagged recombinant wild-type protein EGFRwt under the same assay condition.

In Table 6, variants of h62G7 are described with reference to the heavy chain variation then the light chain variation. For example, antibody clone "h62G7-EQ/L6" refers to the h62G7 clone containing the "EQ" variation in the heavy chain (also referred to herein as "h62G7-EQ") and the "L6" variation in the light chain (also referred to herein as "h62G7-L6"). These heavy chain and light chain amino acid sequences are provided in Table 2. Also, in the present application, a h62G7 variant may be referred to with either the heavy chain or the light chain variant written first—so, for example, "h62G7-EQ/L6" and "h62G7-L6/EQ" both refer to an antibody which contains a h62G7-EQ heavy chain and a h62G7-L6 light chain.

determine the binding affinity and specificity of these hybridomas to EGFRvIII, antibodies in culture supernatants were captured by anti-mouse Fc using Biacore™ T200 biosensor equipped with anti-mouse Fc coupled CM4 sensor chips (Biacore™ AB, Uppsala, Sweden—now GE Healthcare). Monomeric 8-histidine tagged human EGFRvIII extracellular domain was then injected as the analyte at 10-fold dilution series starting with top concentration 1000 nM. Affinity of anti-EGFRvIII antibodies towards human EGFRvIII was measured at 37° C. (Table 7). None of these hybridoma antibodies showed detectable binding to 1000 nM 8-histidine tagged recombinant wild-type protein EGFRwt under the same assay condition.

TABLE 7

| | EGFRvIII binding at 37° C. | | |
|---|---|---|---|
| Antibody | $k_a$ (1/Ms) | $k_d$ (1/s) | $K_D$ (nM) |
| 42G9 | 6.88E+04 | 5.63E−04 | 8.2 |
| 32A10 | 6.54E+04 | 6.26E−04 | 9.6 |
| 21E11 | 6.66E+04 | 6.32E−04 | 9.5 |
| 49B11 | 7.64E+04 | 6.95E−04 | 9.1 |
| 46E10 | 5.97E+04 | 7.16E−04 | 12.0 |
| 12H6 | 5.93E+04 | 7.33E−04 | 12.4 |
| 19A9 | 5.58E+04 | 1.04E−03 | 18.6 |
| 11B11 | 5.21E+04 | 1.13E−03 | 21.7 |
| 21E7 | 6.52E+04 | 1.30E−03 | 19.9 |
| 20B9 | 4.67E+04 | 1.50E−03 | 32.1 |
| 12B2 | 7.38E+04 | 1.79E−03 | 24.3 |
| 11F10 | 6.63E+04 | 2.81E−03 | 42.4 |
| 17G11 | 5.61E+04 | 3.00E−03 | 53.5 |
| 29D5 | 1.02E+05 | 4.24E−03 | 41.6 |
| 14C11 | 7.55E+04 | 5.93E−03 | 78.5 |
| 20E12 | 3.99E+04 | 1.41E−02 | 353.4 |
| 20G5 | 1.25E+05 | 2.89E−02 | 231.2 |
| 26B9 | 1.31E+05 | 3.20E−02 | 244.3 |
| 30D8 | 1.61E+05 | 2.77E−02 | 172.0 |
| 32G8 | 6.82E+03 | 1.22E−02 | 1788.9 |
| 34E7 | 3.77E+04 | 1.28E−02 | 339.5 |

TABLE 6

| | 25° C. | | | 37° C. | | |
|---|---|---|---|---|---|---|
| Antibody | $k_a$(1/Ms) | $k_d$(1/s) | $K_D$(nM) | $k_a$(1/Ms) | $k_d$(1/s) | $K_D$(nM) |
| m62G7 | 7.30E+05 | 6.40E−02 | 88.7 | 8.00E+05 | 1.70E−01 | 207.0 |
| h62G7-EQ/L6 | 2.40E+05 | 1.00E−02 | 43.8 | 6.60E+05 | 7.40E−02 | 112.8 |
| h62G7-EQ/L1-DV | 2.00E+05 | 1.20E−05 | 59.9 | 3.70E+05 | 6.90E−02 | 185.8 |
| h62G7-H14/L1-DV | 1.80E+04 | 2.00E−02 | 1087.9 | 6.60E+04 | 1.00E−01 | 1539.6 |
| h62G7-H14/L6 | 1.30E+04 | 1.30E−02 | 992.2 | 4.30E+04 | 6.80E−02 | 1583.3 |

Example 2: Affinity Determination for Human Anti-EGFRvIII Antibodies

This example determines the affinity of various human anti-EGFRvIII antibodies at 37° C.

To generate human antibodies against EGFRvIII, transgenic AlivaMab mice (Ablexis LLC, San Francisco, Calif.) were immunized with alternating schedule of rat glioblastoma cell line expressing EGFRvIII, F98-npEGFRvIII (American Type Culture Collection, Manassas, Va.) and peptides (SEQ ID NO: 227: CGSGSGLEEKKGNYV-VTDH) directed to the junction region in EGFRvIII. Hybridomas were generated using standard techniques. To

Example 3: Binding Specificity of Anti-EGFRvIII Antibodies to EGFRvIII Expressing Cell Lines by Flow Cytometry This example demonstrates the cell binding specificity of anti-EGFRvIII antibodies to EGFRvIII expressing cells.

Figure 1B:
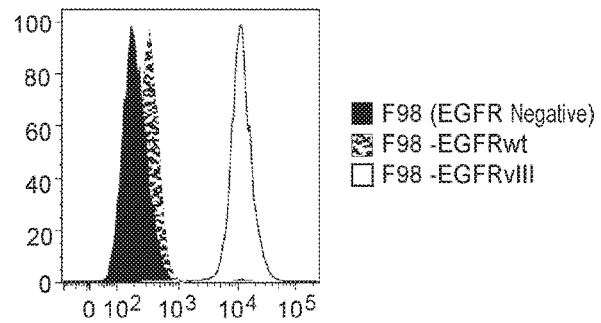
Figure 1C:
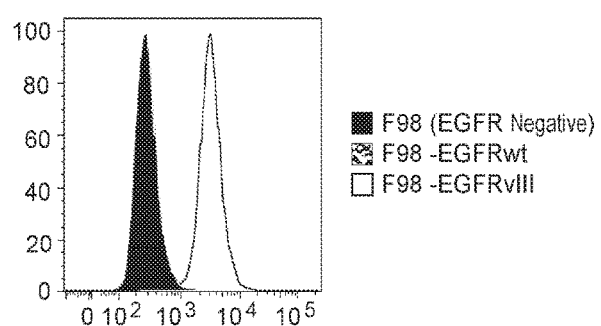

To assess the cell binding specificity of anti-EGFRvIII antibodies generated from the AlivaMab mice, three isogenic rat glioblastoma cell lines and a human cancer cell line were used: F98 (does not express any form of human EGFR), F98-EGFRwt (expresses wild-type EGFR), F98-npEGFRvIII (expresses EGFRvIII) and A431 (an epidermoid carcinoma cell line with wild-type EGFR over-expression), all obtained from American Type Culture Collection (Manassas, Va.). For cell staining, 500,000 cells were incubated with 50 μl hybridoma supernatants for 45 min at 4° C., washed with binding buffer (PBS (Phosphate Buffered Saline)+0.5% BSA (Bovine Serum Albumin)), followed by incubation with FITC-conjugated goat anti-mouse Fc specific secondary antibody from Jackson ImmunoResearch Laboratories (West Grove, Pa.). Tables 8A and 8B show mean fluorescent intensities (MFI) of EGFRvIII antibodies (except clone 20G5) on EGFRvIII expressing cell line were at least 10-fold higher than on non-expressing cell lines. FIG. 1A, FIG. 1B, and FIG. 1C show examples of the FACS binding histograms of three EGFRvIII specific clones which had been cloned and expressed as recombinant human IgG1 antibodies, 42G9 (FIG. 1A), 32A10 (FIG. 1B) and 32G8 (FIG. 1C), to the three F98 cell lines.

TABLE 8A

| Antibody | F98 | | F98-EGFRwt | | F98-EGFRvIII | | A431 | |
|---|---|---|---|---|---|---|---|---|
| | MFI | % positive | MFI | % positive | MFI | % positive | MFI | % positive |
| 2nd Ab only | 170 | 0.6 | 202 | 1.7 | 258 | 2.3 | 592 | 0.4 |
| anti-EGFR(wt and vIII) | 163 | 0.5 | 9608 | 98.3 | 5329 | 99.4 | 55240 | 100.0 |
| 42G9 | 159 | 0.4 | 185 | 1.6 | 3247 | 98.5 | 538 | 0.3 |
| 32A10 | 159 | 0.5 | 185 | 1.4 | 3349 | 98.3 | 531 | 0.2 |
| 21E11 | 159 | 0.3 | 184 | 1.3 | 3105 | 98.5 | 555 | 0.5 |
| 49B11 | 156 | 0.6 | 185 | 1.3 | 2980 | 98.5 | 599 | 0.8 |
| 46E10 | 158 | 0.4 | 187 | 1.6 | 2986 | 98.7 | 560 | 0.5 |
| 12H6 | 157 | 0.5 | 188 | 1.9 | 3445 | 98.3 | 569 | 0.8 |
| 19A9 | 158 | 0.5 | 168 | 1.6 | 3100 | 98.1 | 578 | 1.0 |
| 11B11 | 161 | 0.6 | 187 | 1.7 | 3391 | 98.2 | 589 | 1.2 |
| 21E7 | 159 | 0.3 | 184 | 1.3 | 3105 | 98.5 | 603 | 1.1 |
| 20B9 | 157 | 0.3 | 189 | 1.8 | 3418 | 98.3 | 558 | 0.7 |
| 12B2 | 156 | 0.4 | 185 | 1.5 | 2749 | 97.9 | 571 | 0.8 |
| 11F10 | 155 | 0.5 | 187 | 1.6 | 3283 | 98.0 | 582 | 1.1 |
| 17G11 | 157 | 0.6 | 184 | 1.5 | 3357 | 98.1 | 556 | 0.7 |
| 29D5 | 155 | 0.3 | 185 | 1.3 | 2829 | 97.9 | 531 | 0.4 |
| 14C11 | 157 | 0.4 | 185 | 1.3 | 3213 | 98.2 | 580 | 0.8 |

TABLE 8B

| Antibody | F98 | | F98-EGFRwt | | F98-EGFRvIII | | A431 | |
|---|---|---|---|---|---|---|---|---|
| | MFI | % positive | MFI | % positive | MFI | % positive | MFI | % positive |
| 2nd Ab only | 235 | 0.2 | 252 | 0.2 | 322 | 1.3 | 185 | 0.7 |
| anti-EGFR(wt and vIII) | 245 | 0.3 | 6857 | 97.2 | 5827 | 99.4 | 44493 | 100.0 |
| 20E12 | 381 | 6.0 | 348 | 3.4 | 3976 | 97.9 | 302 | 2.6 |
| 20G5 | 1248 | 16.8 | 1070 | 12.6 | 4639 | 98.5 | 391 | 2.0 |
| 26B9 | 310 | 4.1 | 298 | 2.3 | 5405 | 98.6 | 276 | 1.7 |
| 30D8 | 296 | 4.0 | 280 | 1.7 | 5165 | 98.6 | 269 | 1.3 |
| 32G8 | 329 | 4.9 | 301 | 1.6 | 3734 | 98.6 | 271 | 1.2 |
| 34E7 | 485 | 6.9 | 371 | 4.0 | 4128 | 98.5 | 294 | 1.1 |

Example 4: Affinity Determination for Fully Human Anti-EGFRvIII Antibodies from Phage Library This example determines the affinity of various human anti-EGFRvIII antibodies at 25° C.

Human anti-EGFRvIII antibodies obtained from phage library screen were sequenced and subcloned into suitable vectors for expression as recombinant human IgG1 antibodies. The affinities of antibodies were measured at 25° C. (Table 9) on a surface plasmon resonance Biacore™ T200 biosensor equipped with an anti-human Fc coupled CM4 sensor chip (GE Healthcare Inc., Piscataway, N.J.). Anti-EGFRvIII antibodies were captured by anti-human Fc. Monomeric 8-histidine tagged human EGFRvIII extracellular domain was then injected as the analyte at 10-fold dilution series starting at 1000 nM. Among the two antibodies, only C6 showed very weak but detectable binding to 1000 nM 8-histidine tagged recombinant wild-type protein EGFRwt at 25° C.

TABLE 9

| | EGFRvIII binding at 25° C. | | |
|---|---|---|---|
| Antibody | $k_a$ (1/Ms) | $k_d$ (1/s) | $K_D$ (nM) |
| B5 | 2.08E+04 | 1.41E−02 | 677.9 |
| C6 | 1.68E+04 | 8.94E−03 | 532.1 |

Example 5: Generation and Characterization of GBM Cell Lines Expression EGFRvIII This example demonstrates the expression of wild-type EGFR and EGFRvIII in GBM cell lines.

Figure 2A:
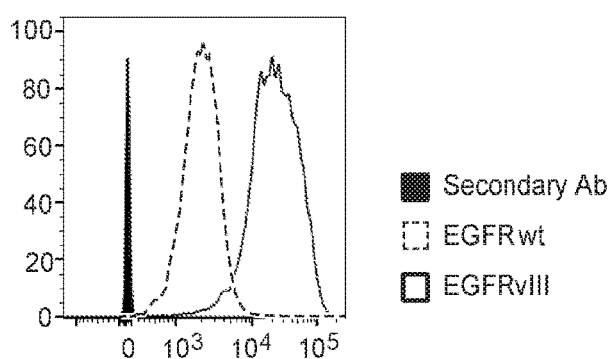
Figure 2B:
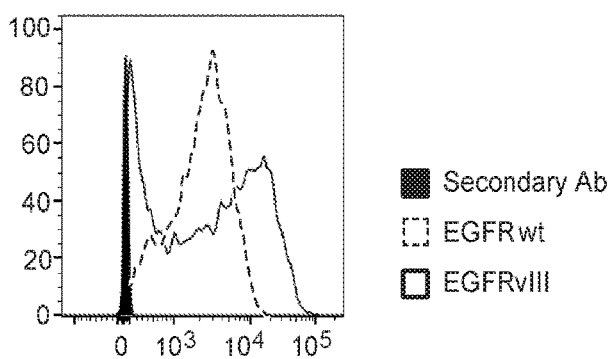
Figure 2C:
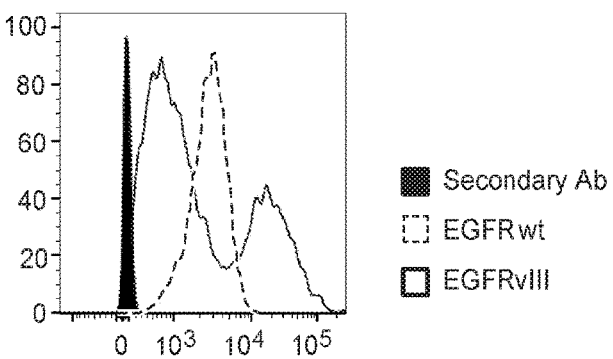

Five GFP (green fluorescent protein) and luciferase transduced human glioblastoma cell lines, DKMG, LN18, LN18-EGFRvIII, LN229 and LN229-EGFRvIII were used for functional characterization. DKMG, which expresses both endogenous wild-type EGFR and EGFRvIII, was obtained from DSMZ (Braunschweig, Germany). LN18 and LN229, which express only wild-type EGFR, were obtained from American Type Culture Collection (Manassas, Va.). To generate GFP-luciferase labeled cell lines, DKMG, LN18 and LN229 were transduced with lentivirus particles (Amsbio, Cambridge, Mass.) encoding both GFP (green fluorescent protein) and luciferase in a bicistronic system. LN18-EGFRvIII and LN229-EGFRvIII were then generated by transduction of the parental cell lines, with a lentivirus vector encoding the full length EGFRvIII gene (SEQ ID NO: 201). Wild-type EGFR and EGFRvIII expression in each cell line was then analysed using flow cytometer. For cell staining, 300,000 cells were incubated with 3 μg EGFR wild-type specific or EGFRvIII specific antibody in 100 μl binding buffer (PBS (Phosphate Buffered Saline)+2% FBS) for 45 min at 4° C., washed with binding buffer, followed by incubation with Alexa Fluor 647-conjugated goat anti-human Fc specific secondary antibody from Jackson ImmunoResearch Laboratories (West Grove, Pa.). FIGS. 2A-C show the expression profiles of wild-type EGFR and EGFRvIII in LN229-EGFRvIII, LN18-EGFRvIII and DKMG, respectively.

Example 6: In Vitro Cytotoxicity Assays with EGFRvIII-CD3 Bispecific Antibodies

This example demonstrates the cytotoxicity of EGFRvIII-CD3 bispecific antibodies towards EGFRvIII expressing GBM cell lines.

To generate EGFRvIII-CD3 bispecific antibodies, the heavy-chain variable domains of anti-EGFRvIII and anti-CD3 antibodies were subcloned into the appropriate human IgG2 based bispecific vectors and expressed with their corresponding light-chain in HEK293 cells. Purification of the EGFRvIII-CD3 bispecific antibodies was done according to published methods (J Mol Biol, 2012, 3, pp 204-219; US patent publication 2013/0115208). In these assays, the EGFRvIII-CD3 bispecific antibodies contain the anti-EGFRvIII sequence of anti-EGFRvIII clones h62G7-EQ/L6, 30D8, or 42G9.

Figure 4A:
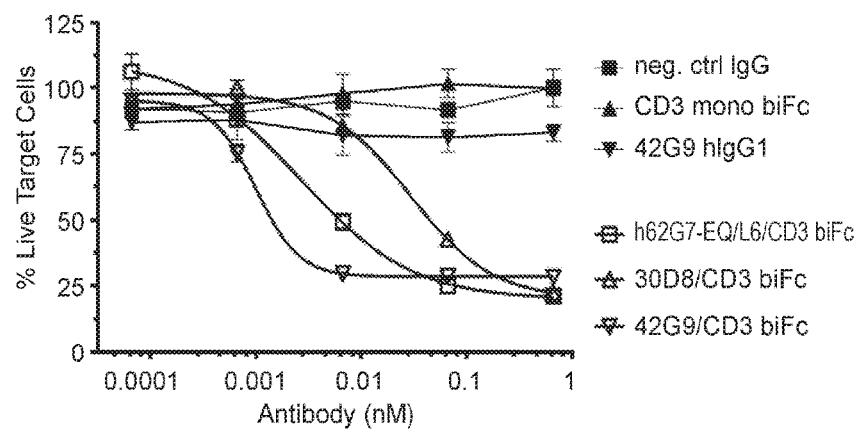
FIGS. 4A and 4B show graphs demonstrating the cytotoxicity of three EGFRvIII-CD3 bispecific antibodies in EGFRvIII transduced LN229-EGFRvIII (FIG. 4A) and parental LN229 (FIG. 4B) cells.
Figure 4B:
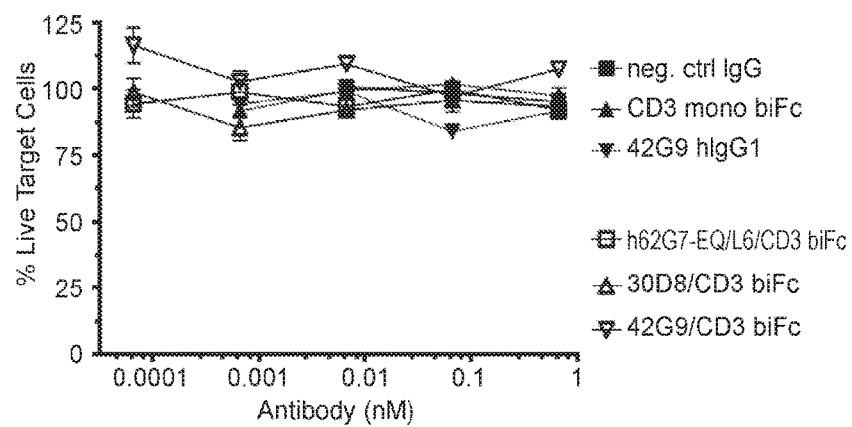
Figure 5:
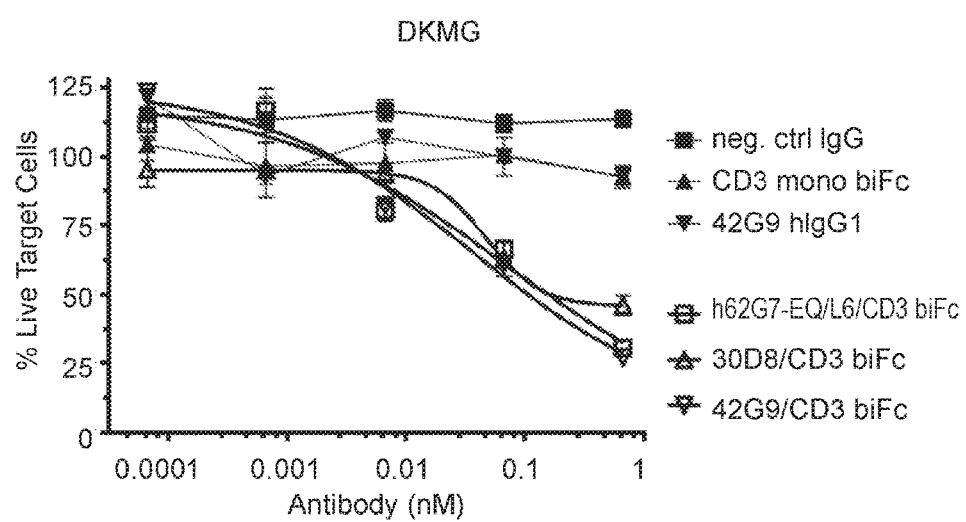
FIG. 5 shows a graph demonstrating the cytotoxicity of three EGFRvIII-CD3 bispecific antibodies in DKMG cells, which express endogenous EGFRvIII and EGFR wild-type proteins.

Target cells in this Example were: EGFRvIII transduced LN18-EGFRvIII cells (FIG. 3A) and parental LN18 (FIG. 3B) cells; EGFRvIII transduced LN229-EGFRvIII (FIG. 4A) and parental LN229 (FIG. 4B) cells; and DKMG cells (which express endogenous EGFRvIII and EGFR wild-type proteins) (FIG. 5).

For the cytotoxicity assays, luciferase transduced target cells were plated in white 96-well plates at 10,000 cells/well in PBMC media (RPMI, 10% FBS, 2 mM L-glutamine, 1% Pen/Strep, 20 uM β-mercaptoethanol, 10 mM HEPES, 1% non-essential amino acids, 1 mM sodium pyruvate) and incubated at 37° C. Twenty-four hours later, activated T cells at the desired T:E (target:effector) ratio (10,000 T cells for 1:1, for LN18 and LN229 cells; 50,000 T cells for 1:5, for DKMG cells) were added to target cells along with the EGFRvIII-CD3 bispecific antibodies, negative control human IgG, negative control CD3 monovalent antibody in bispecific Fc backbone, or negative control bivalent anti-EGFRvIII mAb 42G9 in wild-type human IgG. Cells were incubated for another 24 h at 37° C. To detect the amount of viable target cells at the end of assay, the media was discarded and 100 µl of 150 µg/ml luciferin was added to each well. Luminescence signal was acquired on SpectraMax M5 Plate Reader (Molecular Devices, Sunnyvale, Calif.). Percentage of live target cells was determined by normalizing the luminescence reading for each sample to that of control well containing only target cells.

The results are summarized in FIGS. 3A, 3B, 4A, 4B, and 5. In the graphs, the EGFRvIII-CD3 bispecific antibody data are represented by open symbols, and the negative control antibody data are represented by solid symbols Target cells that expressed EGFRvIII showed a dose-dependent response to treatment with EGFRvIII-CD3 bispecific antibodies h62G7-EQ/L6/CD3 biFc, 30D8/CD3 biFc, and 42G9/CD3 biFc. In contrast, target cells that expressed EGFR wild-type protein only were not killed, thus indicating the specificity of the EGFRvIII-CD3 bispecific antibodies for cells expressing EGFRvIII. In addition, target cells that expressed EGFRvIII did not show a response to treatment with negative control antibodies human IgG, CD3 monovalent biFc, or 42G1 hIgG1 (anti-EGFRvIII antibody).

Figure 3A:
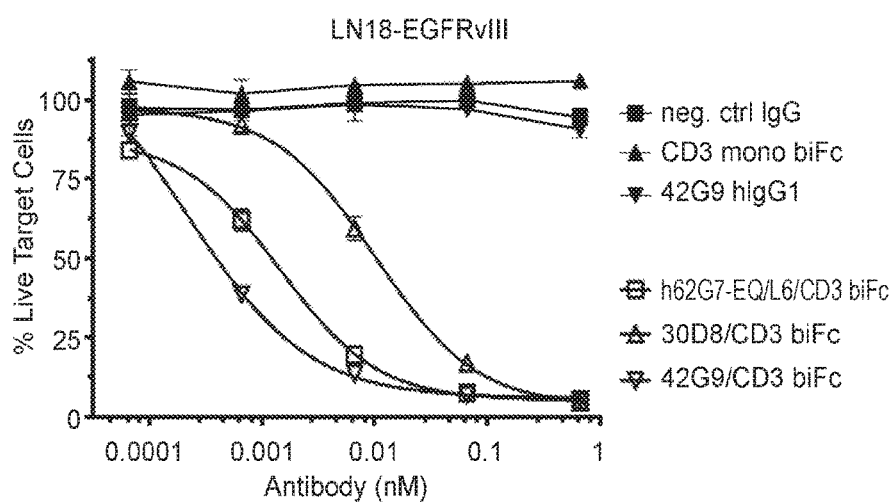
FIGS. 3A and 3B show graphs demonstrating the cytotoxicity of three EGFRvIII-CD3 bispecific antibodies in EGFRvIII transduced LN18-EGFRvIII (FIG. 3A) and parental LN18 (FIG. 3B) cells.
Figure 3B:
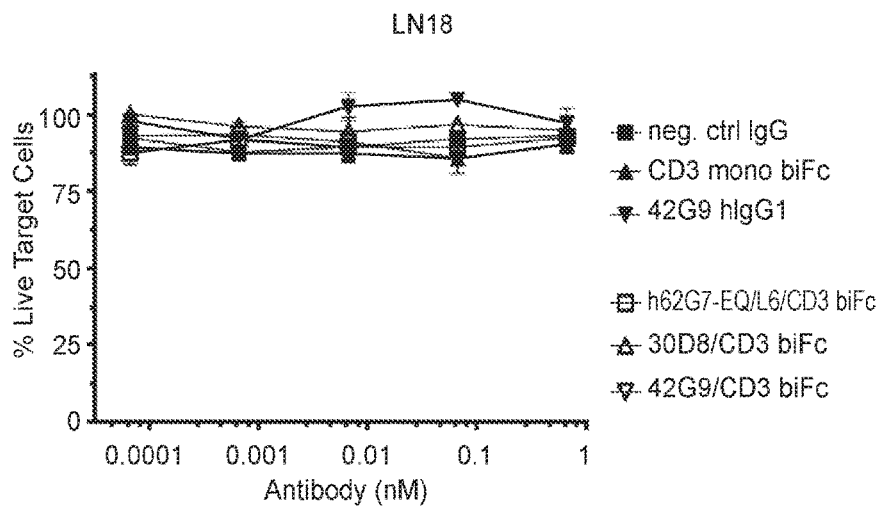

For example, LN18-EGFRvIII target cells treated with 0.01 nM h62G7-EQ/L6/CD3 biFc were only about 20% viable at the end of the assay. In contrast, LN18-EGFRvIII target cells treated with 0.1 nM control IgG, CD3 mono biFc, or 42G9 hIgG1 were about 100% viable at the end of the assay (FIG. 3A). In addition, parental cell line LN18 target cells treated with 0.01 nM h62G7-EQ/L6/CD3 biFc were about 100% viable at the end of the assay (FIG. 3B).

In another example, LN229-EGFRvIII target cells treated with 0.01 nM 42G9/CD3 biFc were only about 35% viable at the end of the assay. In contrast, LN229-EGFRvIII target cells treated with 0.1 nM control IgG, CD3 mono biFc, or 42G9 hIgG1 were about 90-100% viable at the end of the assay (FIG. 4A). In addition, parental cell line LN229 target cells treated with 0.01 nM 42G9/CD3 biFc were about 100% viable at the end of the assay (FIG. 4B).

In another example, DKMG target cells treated with 1 nM h62G7-EQ/L6/CD3 biFc were only about 35% viable at the end of the assay (FIG. 5). In contrast, DKMG target cells treated with 1 nM control IgG, CD3 mono biFc, or 42G9 hIgG1 were about 100% viable at the end of the assay (FIG. 5).

These data demonstrate that EGFRvIII-CD3 bispecific antibodies effectively mediate killing by T cells of EGFRvIII expressing cells.

Example 7: In Vivo Study of Anti-EGFRvIII-CD3 Bispecific Antibodies in a GBM Model LN229-EGFRvIII This example determines the in vivo anti-tumor activity of anti-EGFRvIII bispecific antibodies in a subcutaneous LN229-EGFRvIII GBM cell line model.

Three million LN229-EGFRvIII cells were implanted subcutaneously into 5-6 weeks old NSG mice (Jackson Laboratory, Sacramento, Calif.). Tumor volume was measured once a week by a caliper device and calculated with the following formula: Tumor volume=(length×width$^2$)/2. On day 18 post tumor implantation, animals were randomized by tumor sizes into five animals per group. A single dose of 20 million fresh pan T cells was administered intraperitoneally, followed by bolus tail vein injection of 0.5 mg/kg of EGFRvIII-CD3 bispecific antibodies (the antibodies contained the anti-EGFRvIII sequence of anti-EGFRvIII clones h62G7-EQ/L6, 30D8, or 42G9), or CD3 monovalent control in bispecific Fc backbone.

Figure 6:
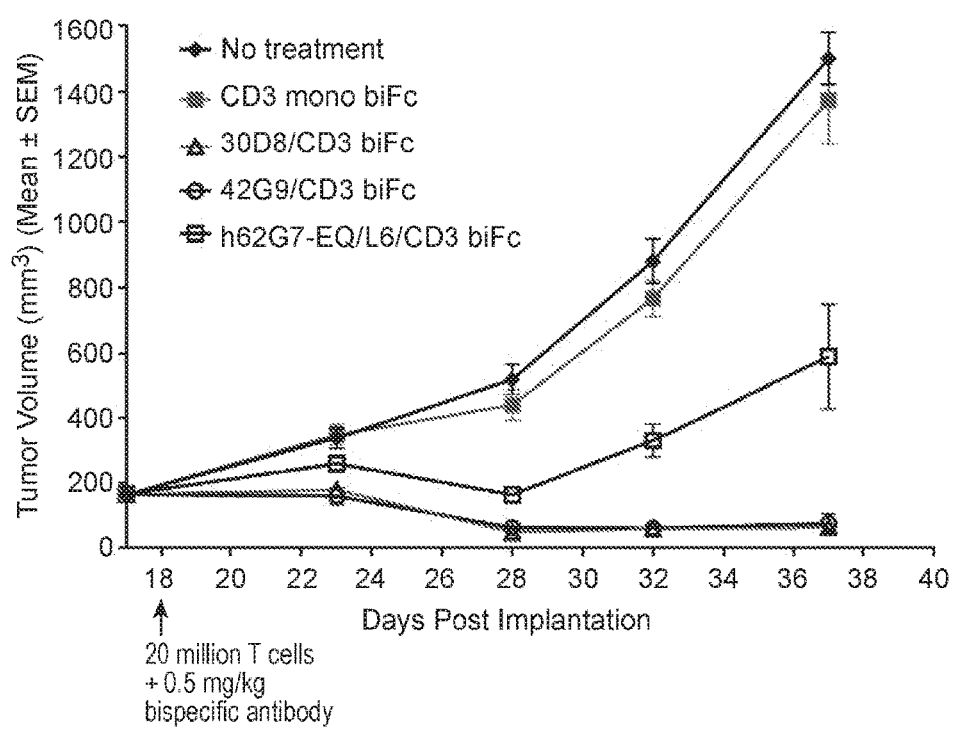
FIG. 6 shows a graph illustrating the in vivo anti-tumor activity of EGFRvIII-CD3 bispecific antibodies in a subcutaneous model of LN229-EGFRvIII GBM cell line.

The results are summarized in FIG. 6. In the graph, the EGFRvIII-CD3 bispecific antibody data are represented by open symbols, and the negative control antibody data are represented by solid symbols.

The EGFRvIII-CD3 bispecific antibodies h62G7-EQ/L6/CD3 biFc, 30D8/CD3 biFc, and 42G9/CD3 biFc inhibited the in vivo growth of the EGFRvIII-expressing LN229-EGFRvIII GBM cells. In contrast, the negative control antibody CD3 monovalent biFc and a no treatment control (i.e. the mouse was not dosed with T cells or antibody) did not inhibit the in vivo growth of the LN229-EGFRvIII GBM cells. For example, at day 37 post tumor implantation, the mean tumor volume for mice treated with the EGFRvIII-CD3 bispecific antibodies 30D8/CD3 biFc and 42G9/CD3 biFc was less than 100 mm$^3$, whereas the mean tumor volume for mice without treatment or treated with the CD3 monovalent biFc was greater than 1200 mm$^3$.

These data demonstrate the in vivo anti-tumor activities of EGFRvIII-CD3 bispecific antibodies against EGFRvIII expressing tumor cells.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated antibody, which specifically binds to Epidermal Growth Factor Receptor Variant III (EGFRvIII), wherein the antibody comprises:
   (a) a heavy chain variable (VH) region comprising (i) a VH complementarity determining region one (CDR1) comprising a sequence selected from the group consisting of SEQ ID NO: 62, 63, 64, 74, 75, 76, 80, 81, 82, 88, 89, 90, 93, 94, 95, 99, 100, 101, 109, 110, 111, 115, 116, 117, 121, 122, 123, 132, 133, 134, 137, 138, 139, 143, 144, and 145; (ii) a VH CDR2 comprising a sequence selected from the group consisting of SEQ ID NO: 65, 66, 68, 69, 70, 71, 77, 78, 83, 84, 86, 87, 91, 92, 96, 97, 98, 102, 103, 105, 106, 112, 113, 118, 119, 124, 125, 127, 128, 130, 131, 135, 136, 140, 141, 146, and 147; and (iii) a VH CDR3 comprising a sequence selected from the group consisting of SEQ ID NO: 67, 72, 73, 79, 85, 104, 107, 108, 114, 120, 126, 129, 142, and 148; and
   (b) a light chain variable (VL) region comprising (i) a VL CDR1 comprising a sequence selected from the group consisting of SEQ ID NO: 149, 154, 156, 159, 162, 165, 166, 168, 169, 170, 171, 173, 174, 176, 178, 181, 182, 185, 187, 190, 192, 195, and 198; (ii) a VL CDR2 comprising a sequence selected from the group consisting of SEQ ID NO: 150, 152, 155, 157, 160, 163, 172, 175, 179, 183, 186, 188, 191, 193, 196, and 199; and (iii) a VL CDR3 comprising a sequence selected from the group consisting of SEQ ID NO: 151, 153, 158, 161, 164, 167, 177, 180, 184, 189, 194, 197, and 200.

2. An isolated antibody which specifically binds to Epidermal Growth Factor Receptor Variant III (EGFRvIII), wherein the antibody comprises:
   a VH region comprising a VH sequence selected from the group consisting of SEQ ID NO: 1, 3, 5, 7, 9, 11, 13, 15, 17, 19, 21, 23, 25, 27, 30, 32, 34, 35, 37, 39, 41, 43, 44, 46, 48, 50, 52, 53, 54, 55, 56, 57, 58, 59, 60, 61, 202, 203, 204, 205, 206, 207, 208, 209, 210, 214, 216, 217, and 218; and
   a VL region comprising a VL sequence selected from the group consisting of SEQ ID NO: 2, 4, 6, 8, 10, 12, 14, 16, 18, 20, 22, 24, 26, 28, 29, 31, 33, 36, 38, 40, 42, 45, 47, 49, 51, 211, 212, 213, and 215.

3. The antibody of claim 1, wherein the antibody comprises an acyl donor glutamine-containing tag engineered at a specific site.

4. A nucleic acid encoding the antibody of claim 1.

5. A vector comprising the nucleic acid of claim 4.

6. A host cell comprising the nucleic acid of claim 4.

7. A conjugate of the antibody of claim 1, wherein the antibody is conjugated to an agent, wherein the agent is selected from the group consisting of a cytotoxic agent, an immunomodulating agent, an imaging agent, a therapeutic protein, a biopolymer, and an oligonucleotide.

8. A pharmaceutical composition comprising the antibody of claim 1.

9. A method of treating a condition associated with malignant cells expressing EGFRvIII in a subject comprising administering to a subject in need thereof an effective amount of the pharmaceutical composition of claim 8.

10. The method of claim 9, wherein the condition is a cancer.

11. The method of claim 10, wherein the cancer is an EGFRvIII related cancer selected from the group consisting of glioblastoma multiform, anaplastic astrocytoma, giant cell glioblastoma, gliosarcoma, anaplastic oligodendroglioma, anaplastic ependymoma, anaplastic oligoastrocytoma, choroid plexus carcinoma, anaplastic ganglioglioma, pineoblastoma, pineocytoma, meningioma, medulloepithelioma, ependymoblastoma, medulloblastoma, supraentorial primitive neuroectodermal tumor, atypical teratoid/rhabdoid tumor, mixed glioma, head and neck cancer, non-small cell lung cancer, breast cancer, ovarian cancer, prostate cancer, medullobastoma, colorectal cancer, anal cancer, cervical cancer, renal cancer, skin cancer, pancreatic cancer, liver cancer, bladder cancer, gastric cancer, thyroid cancer, mesothelioma, uterine cancer, lymphoma, and leukemia.

12. A method of inhibiting tumor growth or progression in a subject who has malignant cells expressing EGFRvIII, comprising administering to the subject in need thereof an effective amount of the pharmaceutical composition of claim 8 to the subject.

13. A method of inhibiting metastasis of malignant cells expressing EGFRvIII in a subject, comprising administering to the subject in need thereof an effective amount of the pharmaceutical composition of claim 8 to the subject.

14. A method of inducing tumor regression in a subject who has malignant cells expressing EGFRvIII, comprising administering to the subject in need thereof an effective amount of the pharmaceutical composition of claim 8 to the subject.

15. A method of producing an antibody, comprising culturing the host cell of claim 6 under conditions that result in production of the antibody, and isolating the antibody from the host cell or culture.

16. The isolated antibody of claim 1, wherein the antibody comprises:
(a) a heavy chain variable (VH) region comprising (i) a VH complementarity determining region one (CDR1) comprising a sequence selected from the group consisting of SEQ ID NO: 62, 63, and 64; (ii) a VH CDR2 comprising a sequence selected from the group consisting of SEQ ID NO: 65, 66, 68, 69, 70, and 71; and (iii) a VH CDR3 comprising a sequence selected from the group consisting of SEQ ID NO: 67, 72, and 73; and
(b) a light chain variable (VL) region comprising (i) a VL CDR1 comprising a sequence selected from the group consisting of SEQ ID NO: 149 and 154; (ii) a VL CDR2 comprising a sequence selected from the group consisting of SEQ ID NO: 150, 152, and 155; and (iii) a VL CDR3 comprising a sequence selected from the group consisting of SEQ ID NO: 151 and 153.

17. The isolated antibody of claim 1, wherein the antibody comprises:
(a) a heavy chain variable (VH) region comprising (i) a VH complementarity determining region one (CDR1) comprising a sequence selected from the group consisting of SEQ ID NO: 74, 75, 76, 80, 81, 82, 88, 89, 90, 93, 94, 95, 99, 100, and 101, and 145; (ii) a VH CDR2 comprising a sequence selected from the group consisting of SEQ ID NO: 77, 78, 83, 84, 86, 87, 91, 92, 96, 97, 98, 102, 103, 105, and 106; and (iii) a VH CDR3 comprising a sequence selected from the group consisting of SEQ ID NO: 79, 85, 104, 107, and 108; and
(b) a light chain variable (VL) region comprising (i) a VL CDR1 comprising a sequence selected from the group consisting of SEQ ID NO: 156, 159, 162, 165, 166, 168, 169, 170, 171, 173, 174, 176, 178, and 181; (ii) a VL CDR2 comprising a sequence selected from the group consisting of SEQ ID NO: 157, 160, 163, and 172; and (iii) a VL CDR3 comprising a sequence selected from the group consisting of SEQ ID NO: 158, 161, 164, 167, 177, and 180.

18. The isolated antibody of claim 1, wherein the antibody comprises:
(a) a heavy chain variable (VH) region comprising (i) a VH complementarity determining region one (CDR1) comprising a sequence selected from the group consisting of SEQ ID NO: 109, 110, 111, 115, 116, 117, 121, 122, 123, 132, 133, and 134; (ii) a VH CDR2 comprising a sequence selected from the group consisting of SEQ ID NO: 112, 113, 118, 119, 124, 125, 127, 128, 130, 131, 135, and 136; and (iii) a VH CDR3 comprising a sequence selected from the group consisting of SEQ ID NO: 114, 120, 126, and 129; and
(b) a light chain variable (VL) region comprising (i) a VL CDR1 comprising a sequence selected from the group consisting of SEQ ID NO: 182, 185, 187, 190, and 192; (ii) a VL CDR2 comprising a sequence selected from the group consisting of SEQ ID NO: 183, 186, 188, 191, and 193; and (iii) a VL CDR3 comprising a sequence selected from the group consisting of SEQ ID NO: 184, 189, and 194.

19. The isolated antibody of claim 1, wherein the antibody comprises:
(a) a heavy chain variable (VH) region comprising (i) a VH complementarity determining region one (CDR1) comprising a sequence selected from the group consisting of SEQ ID NO: 137, 138, 139, 143, 144, and 145; (ii) a VH CDR2 comprising a sequence selected from the group consisting of SEQ ID NO: 140, 141, 146, 147; and (iii) a VH CDR3 comprising a sequence selected from the group consisting of SEQ ID NO: 142 and 148; and
(b) a light chain variable (VL) region comprising (i) a VL CDR1 comprising a sequence selected from the group consisting of SEQ ID NO: 195 and 198; (ii) a VL CDR2 comprising a sequence selected from the group consisting of SEQ ID NO: 196 and 199; and (iii) a VL CDR3 comprising a sequence selected from the group consisting of SEQ ID NO: 197 and 200.

20. The isolated antibody of claim 1, wherein the antibody (14C11) comprises a VH region comprising the amino acid sequence of SEQ ID NO: 15 and a VL region comprising the amino acid sequence of SEQ ID NO: 16.

21. The isolated antibody of claim 1, wherein the antibody (26B9) comprises a VH region comprising the amino acid sequence of SEQ ID NO: 41 and a VL region comprising the amino acid sequence of SEQ ID NO: 42.

22. The isolated antibody of claim 1, wherein the antibody (32A10) comprises a VH region comprising the amino acid sequence of SEQ ID NO: 11 and a VL region comprising the amino acid sequence of SEQ ID NO: 12.

23. The isolated antibody of claim 1, wherein the antibody (30D8) comprises a VH region comprising the amino acid sequence of SEQ ID NO: 37 and a VL region comprising the amino acid sequence of SEQ ID NO: 38.

24. The isolated antibody of claim 1, wherein the antibody (12B2) comprises a VH region comprising the amino acid sequence of SEQ ID NO: 30 and a VL region comprising the amino acid sequence of SEQ ID NO: 31.

25. The isolated antibody of claim 2, wherein the antibody comprises:
a VH region comprising a selected from the group consisting of SEQ ID NO: 1, 3, 5, 7, 9, 11, 13, 15, 17, 19, 21, 23, 25, 27, 30, 32, 34, 35, 37, 39, 41, 43, 44, 46, 48, and 50; and
a VL region comprising selected from the group consisting of SEQ ID NO: 2, 4, 6, 8, 10, 12, 14, 16, 18, 20, 22, 24, 26, 28, 29, 31, 33, 36, 38, 40, 42, 45, 47, 49, and 51.

* * * * *

UNITED STATES PATENT AND TRADEMARK OFFICE
CERTIFICATE OF CORRECTION

PATENT NO. : 10,221,242 B2
APPLICATION NO. : 15/402807
DATED : March 5, 2019
INVENTOR(S) : Oi Kwan Wong et al.

Page 1 of 1

It is certified that error appears in the above-identified patent and that said Letters Patent is hereby corrected as shown below:

In the Claims

In Column 253, Line 7 (Claim 25, Line 3) after "comprising a" insert --sequence--.

In Column 253, Line 11 (Claim 25, Line 7) after "comprising" insert --a sequence--.

Signed and Sealed this
Twentieth Day of August, 2019

Andrei Iancu
*Director of the United States Patent and Trademark Office*